(12) United States Patent
Newberry

(10) Patent No.: US 10,194,871 B2
(45) Date of Patent: Feb. 5, 2019

(54) VEHICULAR HEALTH MONITORING SYSTEM AND METHOD

(71) Applicant: Sanmina Corporation, San Jose, CA (US)

(72) Inventor: Robert Steven Newberry, New Hope, AL (US)

(73) Assignee: SANMINA CORPORATION, San Jose, CA (US)

( * ) Notice: Subject to any disclaimer, the term of this patent is extended or adjusted under 35 U.S.C. 154(b) by 0 days.

(21) Appl. No.: 15/859,147

(22) Filed: Dec. 29, 2017

(65) Prior Publication Data

US 2018/0116605 A1 May 3, 2018

Related U.S. Application Data

(63) Continuation-in-part of application No. 15/811,479, filed on Nov. 13, 2017, and a continuation-in-part of application No. 15/804,581, filed on Nov. 6, 2017, and a continuation-in-part of application No. 15/718,721, filed on Sep. 28, 2017, and a
(Continued)

(51) Int. Cl.
*A61B 5/1455* (2006.01)
*A61B 5/00* (2006.01)
*A61B 5/024* (2006.01)
*A61B 5/145* (2006.01)

(52) U.S. Cl.
CPC .......... *A61B 5/7275* (2013.01); *A61B 5/0002* (2013.01); *A61B 5/0022* (2013.01); *A61B 5/02416* (2013.01); *A61B 5/1455* (2013.01); *A61B 5/14532* (2013.01); *A61B 5/14551* (2013.01); *A61B 5/6817* (2013.01);
(Continued)

(58) Field of Classification Search
None
See application file for complete search history.

(56) References Cited

U.S. PATENT DOCUMENTS 6,985,763 B2  1/2006  Boas et al.
9,149,216 B2  10/2015  Eisen et al.
(Continued)

OTHER PUBLICATIONS

KC Manhesh et al., Wearable Wireless Intelligent Multi-Parameter Health Monitoring Watch, 2013, Texas Instruments India Educators' Conference, IEEE, p. 61-64.
(Continued)

*Primary Examiner* — Eric Winakur
*Assistant Examiner* — Marjan Fardanesh
(74) *Attorney, Agent, or Firm* — Loza & Loza, LLP; Julio M. Loza; Jessica W. Smith

(57) ABSTRACT

A biosensor control module is integrated in a vehicle and includes a transceiver configured to communicate with a plurality of PPG circuits. The PPG circuits have different locations, including a control button of the vehicle, key fob or steering wheel. The biosensor control module receives first spectral data including PPG waveforms from a first PPG circuit at a first location. The biosensor control module also receives second spectral data including PPG waveforms from a second PPG circuit at a second location. The biosensor control module combines the PPG waveforms from the first spectral data and the second spectral data to obtain health information of a user.

28 Claims, 41 Drawing Sheets

Related U.S. Application Data continuation-in-part of application No. 15/680,991, filed on Aug. 18, 2017, now Pat. No. 9,968,289, said application No. 15/718,721 is a continuation of application No. 15/622,941, filed on Jun. 14, 2017, now Pat. No. 9,788,767, application No. 15/859,147, which is a continuation-in-part of application No. 15/490,813, filed on Apr. 18, 2017, now Pat. No. 9,980,676, and a continuation-in-part of application No. 15/489,391, filed on Apr. 17, 2017, now Pat. No. 9,974,451, and a continuation-in-part of application No. 15/485,816, filed on Apr. 12, 2017, and a continuation-in-part of application No. 15/462,700, filed on Mar. 17, 2017, said application No. 15/804,581 is a continuation of application No. 15/404,117, filed on Jan. 11, 2017, application No. 15/859,147, which is a continuation-in-part of application No. 15/400,916, filed on Jan. 6, 2017, said application No. 15/485,816 is a continuation of application No. 15/276,760, filed on Sep. 26, 2016, now Pat. No. 9,636,457, said application No. 15/489,391 is a continuation of application No. 15/275,444, filed on Sep. 25, 2016, now Pat. No. 9,642,538, said application No. 15/490,813 is a continuation of application No. 15/275,388, filed on Sep. 24, 2016, now Pat. No. 9,642,578, application No. 15/859,147, which is a continuation-in-part of application No. 14/866,500, filed on Sep. 25, 2015.

(60) Provisional application No. 62/463,104, filed on Feb. 24, 2017, provisional application No. 62/457,138, filed on Feb. 9, 2017.

(52) U.S. Cl.
CPC ............ *A61B 5/743* (2013.01); *A61B 5/6826* (2013.01); *A61B 5/7225* (2013.01); *A61B 2560/0223* (2013.01)

(56) References Cited

U.S. PATENT DOCUMENTS

| | | |
|---|---|---|
| 2008/0208019 A1 | 8/2008 | Nitzan |
| 2012/0330126 A1 | 12/2012 | Hope et al. |
| 2013/0060098 A1 | 3/2013 | Thomsen et al. |
| 2013/0110311 A1 | 5/2013 | Steeg et al. |
| 2013/0310669 A1 | 11/2013 | Meir Nitzan |
| 2014/0112940 A1 | 4/2014 | Lane |
| 2014/0243648 A1 | 8/2014 | Dubielczyk |
| 2015/0094914 A1 | 4/2015 | Abreu |
| 2015/0109617 A1 | 4/2015 | Gilbert et al. |
| 2015/0148622 A1 | 5/2015 | Moyer et al. |
| 2015/0150453 A1 | 6/2015 | Abreu |
| 2015/0182172 A1 | 7/2015 | Shelley et al. |
| 2015/0229341 A1* | 8/2015 | Fung .................. H04B 1/10 702/191 |
| 2015/0282747 A1 | 10/2015 | Thiele |
| 2015/0366471 A1 | 12/2015 | LeBoeuf et al. |
| 2016/0018257 A1 | 1/2016 | Mirov et al. |
| 2016/0058347 A1 | 3/2016 | Reichgott et al. |
| 2016/0066863 A1 | 3/2016 | Thaveeprungsriporn et al. |
| 2016/0100781 A1 | 4/2016 | Bechtel et al. |
| 2017/0091436 A1 | 3/2017 | Cao |
| 2017/0256110 A1 | 9/2017 | DiVincent et al. |

OTHER PUBLICATIONS

Abdallah et al., Design of a Compact Multi-Sensor System for Non-Invasive Glucose Monitoring Using Optical Spectroscopy, International Conference on Electronics, Biomedical Engineering and its Applications (ICEBEA'2012), Jan. 7-8, 2012, p. 310-317.

Forst et al., Cardiovascular Effects of Disturbed Insulin Activity in Metabolic Syndrome and in Type 2 Diabetic Patients, Insulin Secretion and Action, Horm Metab Res; 2009, 41; p. 123-131.

Mohamed Elgendi, On the Analysis of Fingertip Photoplethysmogram Signals, Current Cardiology Reviews, 2012, 3, p. 14-25, Bentham Science Publishers.

Wikipedia, Cytochrome P450, Dec. 31, 2015, p. 1-12.

Oliver Wieben, Light Absorbance in Pulse Oximetry, Taylor & Francis, 1997, IOP Publishing, p. 1-20.

Wikipedia, Photoplethysmogram, Jul. 25, 2015, p. 1-4.

PCT/US2016/053631 . Int'l search Report & Written Opinion (dated Dec. 8, 2016).

Babbage, "A cardiac biometric recognition system hopes to replace passwords and keys." Economist.com (May 9, 2013).

Elgendi, "On the analysis of fingertip photoplethysmogram signals." Current Cardiology Reviews 8:14-25 (2012).

* cited by examiner

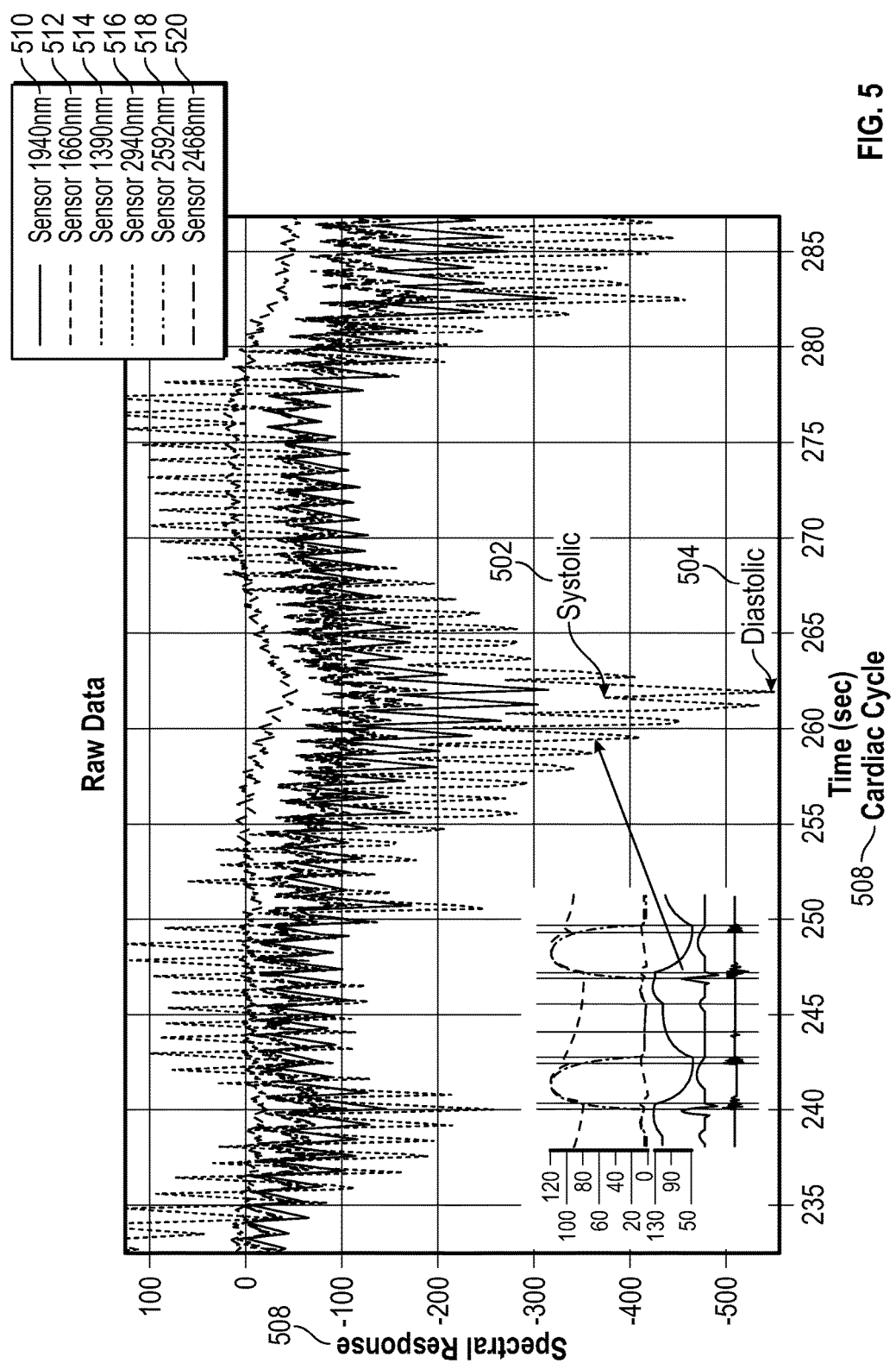

VEHICULAR HEALTH MONITORING SYSTEM AND METHOD

CROSS REFERENCE TO RELATED APPLICATIONS

The present application claims priority under 35 U.S.C. § 120 as a continuation in part application to U.S. patent application Ser. No. 15/811,479 entitled, "SYSTEM AND METHOD FOR A BIOSENSOR INTEGRATED IN A VEHICLE," filed Nov. 13, 2017 and hereby expressly incorporated by reference herein. [SAN-1113CIP]

The present application claims priority under 35 U.S.C. § 120 as a continuation in part application to U.S. patent application Ser. No. 15/490,813 entitled, "SYSTEM AND METHOD FOR HEALTH MONITORING USING A NON-INVASIVE, MULTI-BAND BIOSENSOR," filed Apr. 18, 2017 and hereby expressly incorporated by reference herein which claims priority under 35 U.S.C. § 120 as a continuation application to U.S. Utility application Ser. No. 15/275,388 entitled, "SYSTEM AND METHOD FOR HEALTH MONITORING USING A NON-INVASIVE, MULTI-BAND BIOSENSOR," filed Sep. 24, 2016, and hereby expressly incorporated by reference herein. [SAN-1113CON, SAN-1113]

The present application claims priority under 35 U.S.C. § 120 as a continuation in part application to U.S. patent application Ser. No. 15/489,391 entitled, "SYSTEM AND METHOD FOR A BIOSENSOR MONITORING AND TRACKING BAND," filed Apr. 17, 2017 and hereby expressly incorporated by reference herein, which claims priority under 35 U.S.C. § 120 as a continuation application to U.S. Utility application Ser. No. 15/275,444, entitled, "SYSTEM AND METHOD FOR A BIOSENSOR MONITORING AND TRACKING BAND," filed Sep. 25, 2016 and hereby expressly incorporated by reference herein. [SAN-1123CON, SAN-1123]

The present application claims priority under 35 U.S.C. § 120 as a continuation in part application to U.S. patent application Ser. No. 15/485,816 entitled, "SYSTEM AND METHOD FOR A DRUG DELIVERY AND BIOSENSOR PATCH," filed Apr. 12, 2017 and hereby expressly incorporated by reference herein, which claims priority under 35 U.S.C. § 120 as a continuation application to U.S. Utility application Ser. No. 15/276,760, entitled, "SYSTEM AND METHOD FOR A DRUG DELIVERY AND BIOSENSOR PATCH," filed Sep. 26, 2016, which is hereby expressly incorporated by reference herein. [SAN-1124CON, SAN-1124]

The present application claims priority under 35 U.S.C. § 120 as a continuation in part application to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017 and hereby expressly incorporated by reference herein, which claims priority as a continuation application to U.S. Utility application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, and hereby expressly incorporated by reference herein, which claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein. [SAN-1135CON, SAN-1135]

The present application claims priority under 35 U.S.C. § 120 as a continuation in part application to U.S. patent application Ser. No. 15/804,581 entitled, "SYSTEM AND METHOD FOR HEALTH MONITORING INCLUDING A USER DEVICE AND BIOSENSOR," filed Nov. 6, 2017 and hereby expressly incorporated by reference herein, which claims priority as a continuation application to U.S. patent application Ser. No. 15/404,117 entitled, "SYSTEM AND METHOD FOR HEALTH MONITORING INCLUDING A USER DEVICE AND BIOSENSOR," filed Jan. 11, 2017 and hereby expressly incorporated by reference herein. [SAN-1131CON, SAN-1131]

The present application claims priority under 35 U.S.C. § 120 as a continuation in part application to U.S. patent application Ser. No. 15/462,700 entitled, "SYSTEM AND METHOD FOR ATOMIZING AND MONITORING A DRUG CARTRIDGE DURING INHALATION TREATMENTS," filed Mar. 17, 2017 and hereby expressly incorporated by reference herein, which claims priority under 35 U.S.C. § 119(e) to U.S. Provisional Application No. 62/457,138 entitled, "SYSTEM AND METHOD FOR ATOMIZING AND MONITORING A DRUG CARTRIDGE DURING INHALATION TREATMENTS," filed Feb. 9, 2017, and hereby expressly incorporated by reference herein. [SAN-1134]

The present application claims priority under 35 U.S.C. § 120 as a continuation in part application to U.S. Utility application Ser. No. 15/680,991 entitled, "SYSTEM AND METHOD FOR DETECTING A SEPSIS CONDITION," filed Aug. 18, 2017, and hereby expressly incorporated by reference herein. [SAN-1142]

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein. [SAN-1110]

The present application claims priority under 35 U.S.C. § 120 as a continuation in part to U.S. patent application Ser. No. 14/866,500 entitled, "SYSTEM AND METHOD FOR GLUCOSE MONITORING," filed Sep. 25, 2015, and hereby expressly incorporated by reference herein. [SAN-1108]

FIELD

This application relates to a system and methods of non-invasive health monitoring integrated in a vehicle, and in particular a system and method for health monitoring using spectral data from a plurality of biosensors integrated in a vehicle.

BACKGROUND

A person's vitals, such as temperature, blood oxygen levels, respiration rate, relative blood pressure, etc., may need to be monitored periodically typically using one or more instruments. For example, instruments for obtaining vitals of a user include blood pressure cuffs, thermometers, $SpO_2$ measurement devices, glucose level meters, etc. Often, multiple instruments must be used to obtain vitals of a person. This monitoring process is time consuming, inconvenient and is not always continuous. This multitude of instruments is also not portable or readily available to operators of a vehicle.

In addition, detection of substances and measurement of concentration level or indicators of various substances in a user's blood stream is important in health monitoring. Currently, detection of concentration levels of blood substances is performed by drawing blood from a blood vessel using a needle and syringe. The blood sample is then transported to a lab for analysis. This type of monitoring is invasive, non-continuous and time consuming.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. Such PPG techniques are heretofore been limited to determining oxygen saturation.

As such, there is a need for a continuous and non-invasive health monitoring system and method that measures user vitals and monitors concentration levels or indicators of one or more substances in blood flow.

In addition, there is a need for a continuous and non-invasive health monitoring system and method integrated in a vehicle to measure and provide feedback on a driver's vitals and alertness.

SUMMARY

According to a first aspect, a biosensor control module integrated in a vehicle includes a transceiver configured to communicate with a plurality of biosensors and a processing circuit. The processing circuit receives first spectral data including photoplethysmography (PPG) waveforms from a first biosensor at a first location and receives second spectral data including PPG waveforms from a second biosensor at a second location. The processing circuit processes the first spectral data and the second spectral data to obtain health information of a user, wherein the health information includes one or more of: a heart rate, a respiration rate or blood oxygen level.

According to second aspect, a biosensor control module includes a transceiver that communicates with a plurality of PPG circuits and a processing circuit. The processing circuit receives first spectral data from a first PPG circuit at a first location and receives second spectral data from a second PPG circuit at a second location. The processing circuit combines the first spectral data and the second spectral data to obtain health information of a user, wherein the health information includes one or more of: a heart rate, a respiration rate or blood oxygen level.

According to a third aspect, a biosensor includes a transceiver configured to communicate with a vehicle and a PPG circuit configured to obtain spectral data including PPG waveforms. The biosensor further includes a processing circuit configured to process the spectral data to obtain health information of a user, wherein the health information includes one or more of: a heart rate, a respiration rate or blood oxygen level and generate a health message to the vehicle, wherein the health message includes a request for feedback from the vehicle in response to the health information.

In one or more of the above aspects, the processing circuit is further configured to combine the first spectral data and the second spectral data to obtain a set of PPG waveforms and process the set of PPG waveforms to obtain the health information of the user.

In one or more of the above aspects, the processing circuit is further configured to generate an alert to the vehicle in response to the health information for controlling one or more operations of the vehicle.

In one or more of the above aspects, the processing circuit is further configured to process the first spectral data and the second spectral data to obtain a biometric measurement of a user.

In one or more of the above aspects, the processing circuit is further configured to compare the biometric measurement of the user with one or more stored biometric measurements; determine the biometric measurement is within a predetermined threshold; and generate an authentication message to the vehicle.

In one or more of the above aspects, the biometric measurement of the user includes a blood group or a PPG waveform.

In one or more of the above aspects, the processing circuit is further configured to determine one or more characteristics of the PPG waveforms of the user and compare the one or more characteristics of the PPG waveforms to stored characteristics of PPG waveforms of authorized users.

In one or more of the above aspects, the processing circuit is further configured to determine the one or more characteristics of the PPG waveforms of the user are within predetermined thresholds of the stored characteristics of PPG waveforms of authorized users; and generate an authentication message to the vehicle.

BRIEF DESCRIPTION OF THE DRAWINGS

FIG. 5 illustrates a schematic diagram of a graph of actual clinical data obtained using an embodiment of the biosensor and PPG techniques at a plurality of wavelengths.

DETAILED DESCRIPTION

Figure 1:
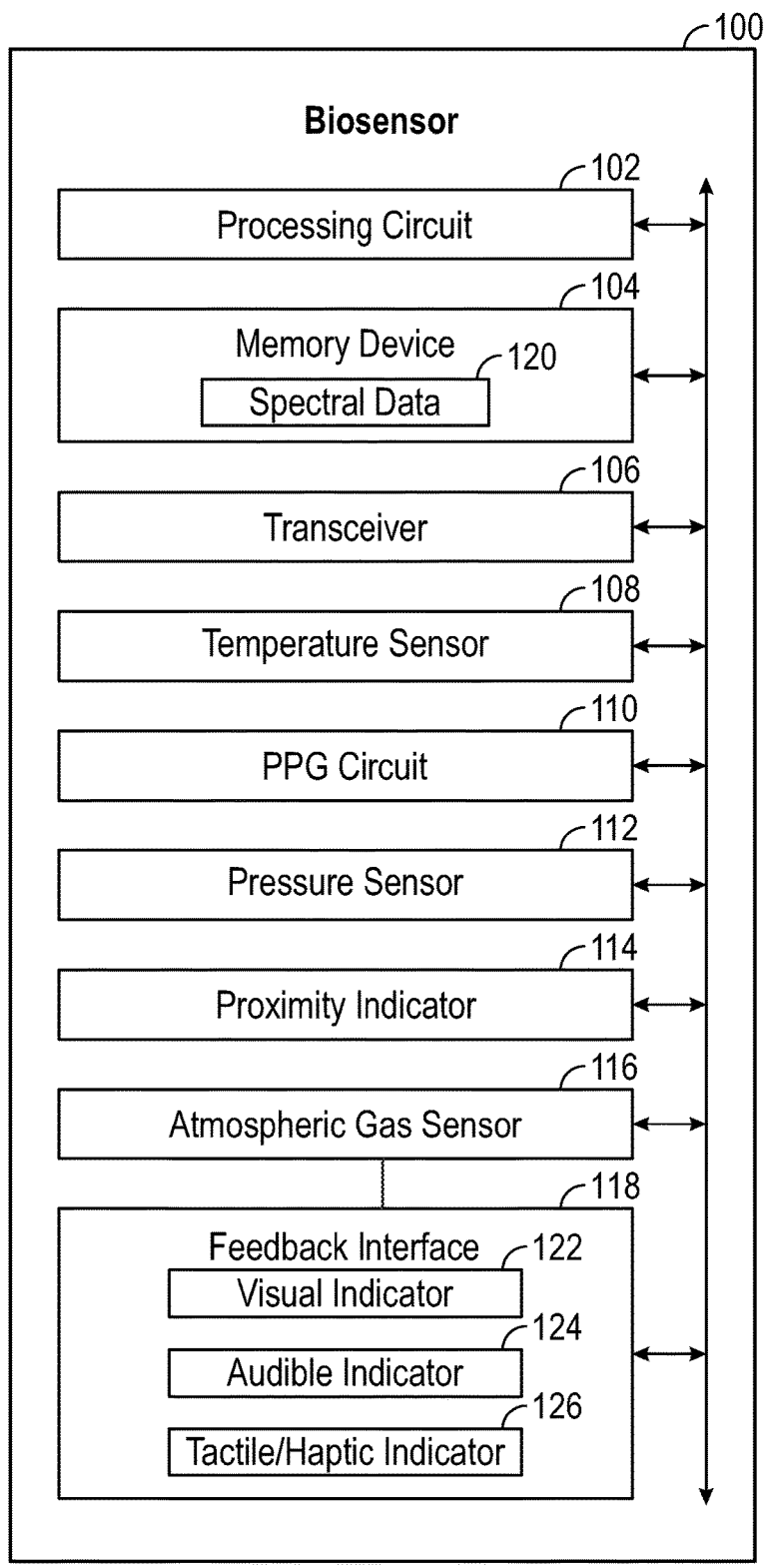
FIG. 1 illustrates a schematic block diagram of exemplary components in an embodiment of the biosensor.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview of a Vehicular Health Monitoring System and Method

In one or more embodiments herein, a plurality of biosensors are integrated in one or more of: a key fob, an ignition control, a steering wheel, a smart phone, etc. Each of the plurality of biosensors include an optical sensor or PPG circuit configured to detect spectral responses of light reflected from arteries, vessels and/or surrounding tissues of a user. The plurality of biosensors each include a transceiver for transmitting the spectral data to a central control module in a vehicle for processing. The central control module process the spectral data from the plurality of bio sensors to obtain a user's vitals and/or concentration levels of one or more substances in blood flow of the user. The vehicular health monitoring system may also provide a visible, audible or tactile indicator that signals one or more of the biosensors is operating or currently obtaining spectral data of a user. An indicator during the measurement period may be provided that indicates the detected spectral data is within tolerance limits. The vehicular health monitoring system may display the user vitals and other obtained health data. The vehicular health monitoring system thus provides noninvasive monitoring of a user's vitals and blood concentration levels of one or more substances.

Embodiment of the Biosensor

In an embodiment, a biosensor includes an optical sensor or photoplethysmography (PPG) circuit configured to transmit light at a plurality of wavelengths directed at skin tissue of a user. The user may include any living organism, human or non-human. The PPG circuit detects the light reflected from the skin tissue and generates one or more spectral responses at the plurality of wavelengths. A processing circuit integrated in the biosensor or in communication with the biosensor processes the spectral data to obtain a user's vitals and/or other health information.

FIG. 1 illustrates a schematic block diagram of exemplary components in an embodiment of the biosensor 100. The biosensor 100 includes a PPG circuit 110 as described in more detail herein. The PPG circuit 110 may be configured to detect oxygen saturation (SaO2 or SpO2) levels in blood flow, as well as heart rate and respiration rate. In addition, the PPG circuit 110 is configured to detect concentration levels of one or more substances in blood flow of a user, e.g., using one or more measurement techniques as described in more detail herein.

The biosensor 100 may include one or more processing circuits 202 communicatively coupled to a memory device 204. In one aspect, the memory device 204 may include one or more non-transitory processor readable memories that store instructions which when executed by the one or more processing circuits 102, causes the one or more processing circuits 102 to perform one or more functions described herein. The processing circuit 102 may be co-located with one or more of the other circuits of the biosensor 100 in a same physical circuit board or located separately in a different circuit board or encasement. The processing circuit may also be communicatively coupled to a central control module integrated in a vehicle as described further herein. The biosensor 100 may be battery operated and include a battery 210, such as a lithium ion battery. The memory device may store spectral data 120 or other health information or data obtained by the biosensor 100.

The biosensor 100 may include a temperature sensor 108 configured to detect a temperature of a user. For example, the temperature sensor 108 may include an array of sensors (e.g., 16×16 pixels) to detect a temperature of skin tissue of a user. The temperature sensor 108 may also be used to calibrate the PPG circuit 110.

The biosensor 100 may also include a touch pad or touch point with a proximity indicator 114 and pressure sensor 112. The proximity indicator 114 includes one or more LEDs, e.g. in the IR range, that emit pulses of light. When a finger or other body part is positioned near the touch point, a photodiode may then detect a reflectance of the IR light. The biosensor 100 may then activate the PPG circuit 110. A pressure sensor 112 may detect a pressure on the touch point by a finger or other body part and provide a feedback indicator. The feedback indicator provides a visible, audible or tactile indication that the pressure applied by the finger is within tolerance levels or needs to increase or decrease for proper detection of spectral data by the biosensor 100.

The biosensor 100 may also include an atmospheric gas sensor 116 configured to detect one or more types of gases in the interior of a vehicle. For example, the gas sensor 116 may detect carbon monoxide, carbon dioxide, nitrogen dioxide, sulfur dioxide, or other gases that may be harmful to a user and present in the air in an interior of a vehicle. The vehicular monitoring system may then provide a feedback or indicator when such harmful gases are detected over a predetermined threshold that may be harmful or affect a user.

The biosensor 100 also includes a feedback interface 118 configured to initiate a visual indicator 122, audible indicator 124 or tactile or haptic indicator 126.

The biosensor 100 further includes a transceiver 106. The transceiver 106 may include a wireless or wired transceiver configured to communicate with or with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 106 may also include a wired transceiver interface, e.g., a USB port or other type of wired connection, for communication with one or more other devices over a LAN, MAN and/or WAN. The transceiver 106 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol.

Embodiment—PPG Circuit

Figure 2:
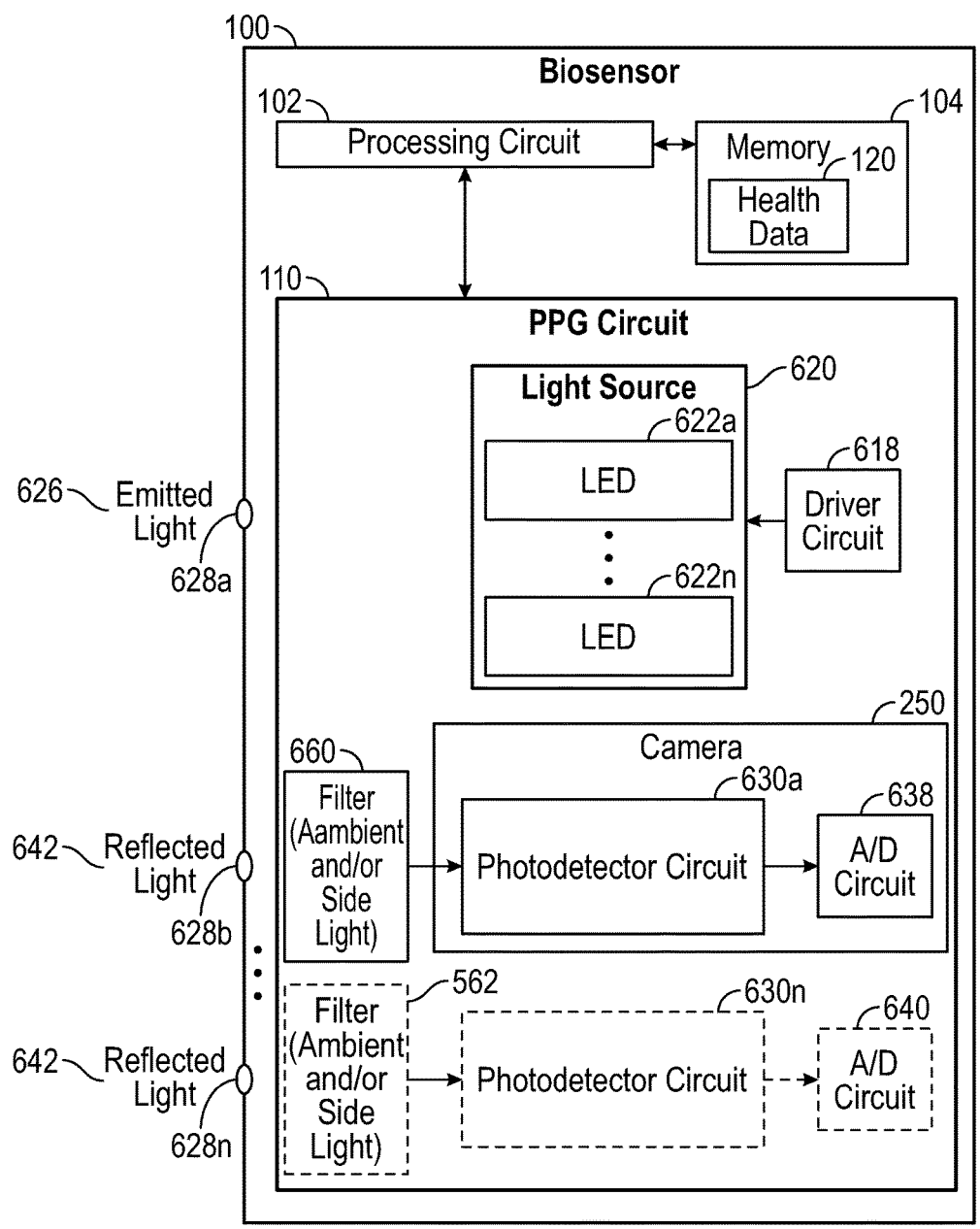
FIG. 2 illustrates a schematic block diagram of an embodiment of the PPG circuit in more detail.

FIG. 2 illustrates a schematic block diagram of an embodiment of the PPG circuit 110 in more detail. The PPG circuit 110 includes a light source 620 configured to emit a plurality of wavelengths of light across various spectrums. For example, the light source 620 mat include a plurality of LEDs 622a-n. The PPG circuit 110 is configured to direct the emitted light at an outer or epidermal layer of skin tissue of a user through at least one aperture 628a. The plurality of LEDs 622a-n are configured to emit light in one or more spectrums, including infrared (IR) light, ultraviolet (UV) light, near IR light or visible light, in response to driver circuit 618. For example, the biosensor 100 may include a first LED 622a that emits visible light and a second LED 622b that emits infrared light and a third LED 622c that emits UV light, etc. In another embodiment, one or more of the light sources 622a-n may include tunable LEDs or lasers operable to emit light over one or more frequencies or ranges of frequencies or spectrums in response to driver circuit 618.

In an embodiment, the driver circuit 618 is configured to control the one or more LEDs 622a-n to generate light at one or more frequencies for predetermined periods of time. The driver circuit 618 may control the LEDs 622a-n to operate concurrently or consecutively. The driver circuit 618 is configured to control a power level, emission period and frequency of emission of the LEDs 622*a-n*. The biosensor 100 is thus configured to emit one or more wavelengths of light in one or more spectrums that is directed at the surface or epidermal layer of the skin tissue of a user.

The PPG circuit 110 further includes one or more photodetector circuits 630*a-n*. The photodetector circuits 630 may be implemented as part of a camera 250. For example, a first photodetector circuit 630 may be configured to detect visible light and the second photodetector circuit 630 may be configured to detect IR light. Alternatively, one or more of the photodetectors 630*a-n* may be configured to detect light across multiple spectrums. When multiple photodetectors 630 are implemented, the detected signals obtained from each of the photodetectors may be added or averaged. The first photodetector circuit 630 and the second photodetector circuit 630 may also include a first filter 660 and a second filter 662 configured to filter ambient light and/or scattered light. For example, in some embodiments, only light reflected at an approximately perpendicular angle to the skin surface of the user is desired to pass through the filters. The first photodetector circuit 630 and the second photodetector circuit 632 are coupled to a first A/D circuit 638 and a second A/D circuit 640. Alternatively, a single A/D circuit may be coupled to each of the photodetector circuits 630*a-n*.

In another embodiment, a single photodetector circuit 630 may be implemented operable to detect light over multiple spectrums or frequency ranges. The one or more photodetector circuits 630 include one or more types of spectrometers or photodiodes or other type of circuit configured to detect an intensity of light as a function of wavelength to obtain a spectral response. In use, the one or more photodetector circuits 630 detect the intensity of light reflected from skin tissue of a user that enters one or more apertures 628*b-n* of the biosensor 100. In another example, the one or more photodetector circuits 630 detect the intensity of light due to transmissive absorption (e.g., light transmitted through tissues such as a fingertip or ear lobe). The one or more photodetector circuits 630*a-n* then obtain a spectral response of the reflected or transmissive light by measuring an intensity of the light at one or more wavelengths.

In another embodiment, the light source 620 may include a broad spectrum light source, such as a white light to infrared (IR) or near IR LED 622, that emits light with wavelengths across multiple spectrums, e.g. from 350 nm to 2500 nm. Broad spectrum light sources 620 with different ranges may be implemented. In an aspect, a broad spectrum light source 620 is implemented with a range across 100 nm wavelengths to 2000 nm range of wavelengths in the visible, IR and/or UV frequencies. For example, a broadband tungsten light source 620 for spectroscopy may be used. The spectral response of the reflected light is then measured across the wavelengths in the broad spectrum, e.g. from 350 nm to 2500 nm, concurrently. In an aspect, a charge coupled device (CCD) spectrometer may be configured in the photodetector circuit 630 to measure the spectral response of the detected light over the broad spectrum.

The PPG circuit 110 may also include a digital signal processing (DSP) circuit or filters or amplifiers to process the spectral data. The spectral data may then be processed by the processing circuit 102 to obtain health data of a user. The spectral data may alternatively or in additionally be transmitted by the biosensor 100 to a central control module in a vehicle for processing to obtain health data of a user.

One or more of the embodiments of the biosensor 100 described herein is configured to detect a concentration level of one or more substances within blood flow using photoplethysmography (PPG) techniques. For example, the biosensor 100 may detect nitric oxide (NO) concentration levels and correlate the NO concentration level to a blood glucose level. The biosensor 100 may also detect oxygen saturation (SaO2 or SpO2) levels in blood flow. The biosensor may also be configured to detect a liver enzyme cytochrome oxidase (P450) enzyme and correlate the P450 concentration level to a blood alcohol level. The biosensor 100 may also detect vitals, such as heart rate and respiration rate. Because blood flow to the skin can be modulated by multiple other physiological systems, the biosensor 100 may also be used to monitor hypovolemia and other circulatory conditions.

In use, the biosensor 100 performs PPG techniques using the PPG circuit 110 to detect the concentration levels of one or more substances in blood flow. In one aspect, the biosensor 100 receives reflected light from skin tissue to obtain a spectral response. The spectral response includes a spectral curve that illustrates an intensity or power or energy at a frequency or wavelength in a spectral region of the detected light. The ratio of the resonance absorption peaks from two different frequencies can be calculated and based on the Beer-Lambert law used to obtain the levels of substances in the blood flow.

First, the spectral response of a substance or substances in the arterial blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined. For example, the concentration Cg may be obtained from the following equations:

At the first wavelength $\lambda_1$, $I_1 = I_{in1} * 10^{-(\alpha_{g1} C_{gw} + \alpha_{w1} C_w) * l}$ At the second wavelength $\lambda_2$, $I_2 = I_{in2} * 10^{-(\alpha_{g2} C_{gw} + \alpha_{w2} C_w) * l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10 \left( \frac{I1}{Iin1} \right)}{\log 10 \left( \frac{I2}{Iin2} \right)}$$

The concentration of the substance Cg may then be equal to:

$$Cg = \frac{Cgw}{Cgw + Cw} = \frac{\alpha_{w2} R - \alpha_{w1}}{(\alpha_{w2} - \alpha_{g2}) * R - (\alpha_{w1} - \alpha_{g1})}$$

The biosensor 100 may thus determine the concentration of various substances in arterial blood flow from the Beer-Lambert principles using the spectral responses of at least two different wavelengths.

Figure 3:
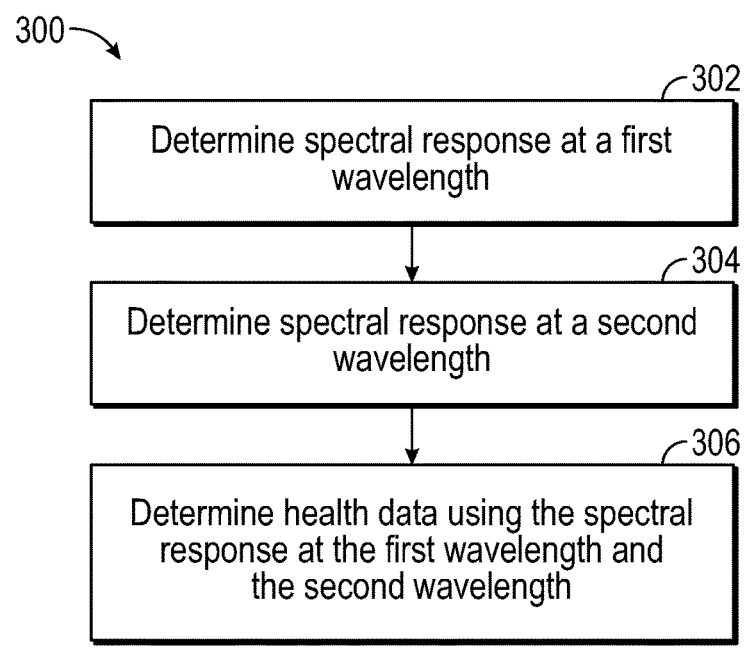
FIG. 3 illustrates a logical flow diagram of an embodiment of a method for determining concentration level of a substance in blood flow using Beer-Lambert principles.

FIG. 3 illustrates a logical flow diagram of an embodiment of a method 300 for determining concentration level of a substance in blood flow using Beer-Lambert principles. The biosensor 100 transmits light at a first predetermined wavelength and at a second predetermined wavelength. The biosensor 100 detects the light (reflected from the skin or transmitted through the skin) and determines the spectral response at the first wavelength at 302 and at the second wavelength at 304. The biosensor 100 then determines an indicator or concentration level of the substance using the spectral responses of the first and second wavelength at 306. In general, the first predetermined wavelength is selected that has a high absorption coefficient for the substance in blood flow while the second predetermined wavelength is selected that has a lower absorption coefficient for the substance in blood flow. Thus, it is generally desired that the spectral response for the first predetermined wavelength have a higher intensity level in response to the substance than the spectral response for the second predetermined wavelength.

In an embodiment, the biosensor 100 may detect a concentration level of NO in blood flow using a first predetermined wavelength in a range of 380-410 nm and in particular at 390 nm or 395 nm. In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 302 and 304. The biosensor 100 analyzes the first and second spectral responses to detect an indicator or concentration level of NO in the arterial blood flow at 306.

Figure 4A:
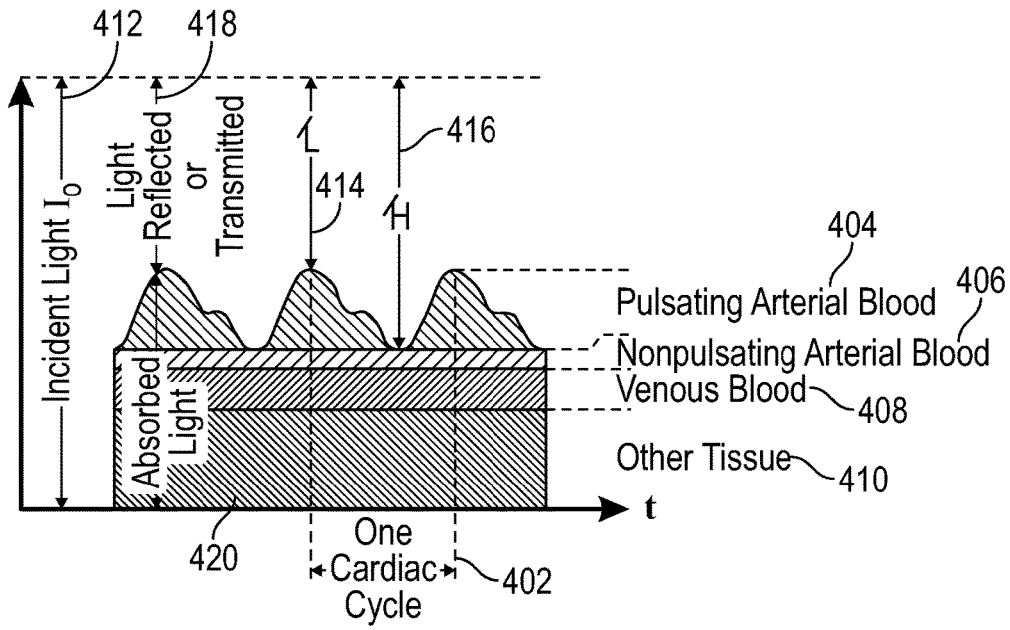
FIG. 4A illustrates a schematic block diagrams of an embodiment of a method for photoplethysmography (PPG) techniques in more detail.
Figure 4B:
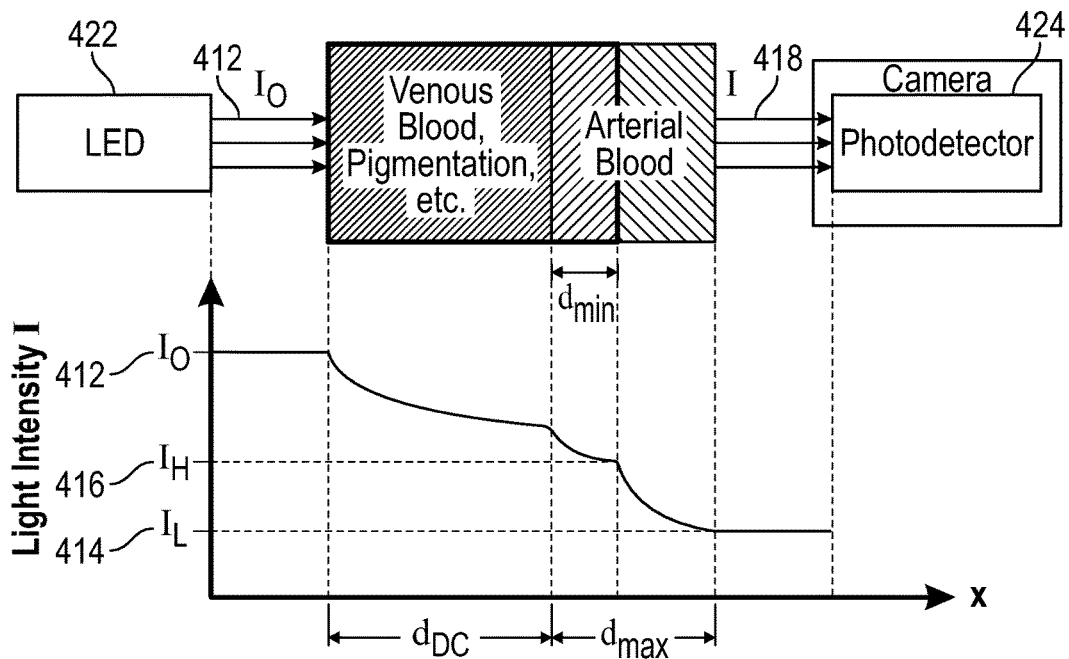
FIG. 4B illustrates another schematic block diagram of an embodiment of a method for photoplethysmography (PPG) techniques in more detail.

FIG. 4A and FIG. 4B illustrate schematic block diagrams of an embodiment of a method for photoplethysmography (PPG) techniques in more detail. Photoplethysmography (PPG) is used to measure time-dependent volumetric properties of blood in blood vessels due to the cardiac cycle. For example, the heartbeat affects the volume of arterial blood flow and the concentration or absorption levels of substances being measured in the arterial blood flow. As shown in FIG. 4A, over a cardiac cycle 402, pulsating arterial blood 404 changes the volume of blood flow in an artery.

Incident light $I_O$ 412 is directed at a tissue site and a certain amount of light is reflected or transmitted 418 and a certain amount of light is absorbed 420. At a peak of arterial blood flow or arterial volume, the reflected/transmitted light $I_L$ 414 is at a minimum due to absorption by the venous blood 408, nonpulsating arterial blood 406, pulsating arterial blood 404, other tissue 410, etc. At a minimum of arterial blood flow or arterial volume during the cardiac cycle, the transmitted/reflected light $I_H$ 416 is at a maximum due to lack of absorption from the pulsating arterial blood 404.

The biosensor 100 is configured to filter the reflected/transmitted light $I_L$ 414 of the pulsating arterial blood 404 from the transmitted/reflected light $I_H$ 416. This filtering isolates the light due to reflection/transmission of substances in the pulsating arterial blood 404 from the light due to reflection/transmission from venous (or capillary) blood 408, other tissues 410, etc. The biosensor 100 may then measure the concentration levels of one or more substances from the reflected/transmitted light $I_L$ 814 in the pulsating arterial blood flow 404.

For example, as shown in FIG. 4B, incident light $I_O$ 412 is directed at a tissue site by an LED 422 at one or more wavelengths. The reflected/transmitted light I 418 is detected by photodetector 424 or camera 250. At a peak of arterial blood flow or arterial volume, the reflected light $I_L$ 414 is at a minimum due to absorption by venous blood 808, non-pulsating arterial blood 406, pulsating arterial blood 404, other tissue 410, etc. At a minimum of arterial blood flow or arterial volume during the cardiac cycle, the Incident or reflected light $I_H$ 416 is at a maximum due to lack of absorption from the pulsating arterial blood 404. Since the light I 418 is reflected or traverses through a different volume of blood at the two measurement times, the measurement provided by a PPG sensor is said to be a 'volumetric measurement' descriptive of the differential volumes of blood present at a certain location within the user's arteriolar bed at different times. Though the above has been described with respect to arterial blood flow, the same principles described herein may be applied to venous blood flow.

In general, the relative magnitudes of the AC and DC contributions to the reflected/transmitted light signal I 418 may be used to substantially determine the differences between the diastolic points and the systolic points. In this case, the difference between the reflected light $I_L$ 414 and reflected light $I_H$ 416 corresponds to the AC contribution of the reflected light 418 (e.g. due to the pulsating arterial blood flow). A difference function may thus be computed to determine the relative magnitudes of the AC and DC components of the reflected light I 418 to determine the magnitude of the reflected light $I_L$ 414 due to the pulsating arterial blood 404. The described techniques herein for determining the relative magnitudes of the AC and DC contributions is not intended as limiting. It will be appreciated that other methods may be employed to isolate or otherwise determine the relative magnitude of the light $I_L$ 414 due to pulsating arterial blood flow.

FIG. 5 illustrates a schematic diagram of a graph of actual clinical data obtained using an embodiment of the biosensor 100 and PPG techniques at a plurality of wavelengths. In one aspect, the biosensor 100 is configured to emit light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral responses 508 for the plurality of wavelengths obtained using an embodiment of the biosensor in clinical trials is shown in FIG. 5. In this clinical trial, two biosensors 100 attached to two separate fingertips of a user were used to obtain the spectral responses 508. The first biosensor 100 obtained the spectral response for a wavelength at 940 nm 510, a wavelength at 660 nm 512 and a wavelength at 390 nm 514. The second biosensor 100 obtained the spectral response for a wavelength at 940 nm 516, a wavelength at 592 nm 518 and a wavelength at 468 nm 520.

In one aspect, the spectral response obtained at each wavelength may be aligned based on the systolic 502 and diastolic 504 points in their respective spectral responses. This alignment is useful to associate each spectral response with a particular stage or phase of the pulse-induced local pressure wave within the blood vessel (which may mimic the cardiac cycle 506 and thus include systolic and diastolic stages and sub-stages thereof). This temporal alignment helps to determine the absorption measurements acquired near a systolic point in time of the cardiac cycle and near the diastolic point in time of the cardiac cycle 506 associated with the local pressure wave within the user's blood vessels. This measured local pulse timing information may be useful for properly interpreting the absorption measurements in order to determine the relative contributions of the AC and DC components measured by the biosensor 100. So for one or more wavelengths, the systolic points 502 and diastolic points 504 in the spectral response are determined. These systolic points 502 and diastolic points 504 for the one or more wavelengths may then be aligned as a method to discern concurrent responses across the one or more wavelengths.

In another embodiment, the systolic points 502 and diastolic points 504 in the absorbance measurements are temporally correlated to the pulse-driven pressure wave within the arterial blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 5 illustrates the spectral response obtained at the plurality of wavelengths with the systolic points 502 and diastolic points 504 aligned.

Figure 6:
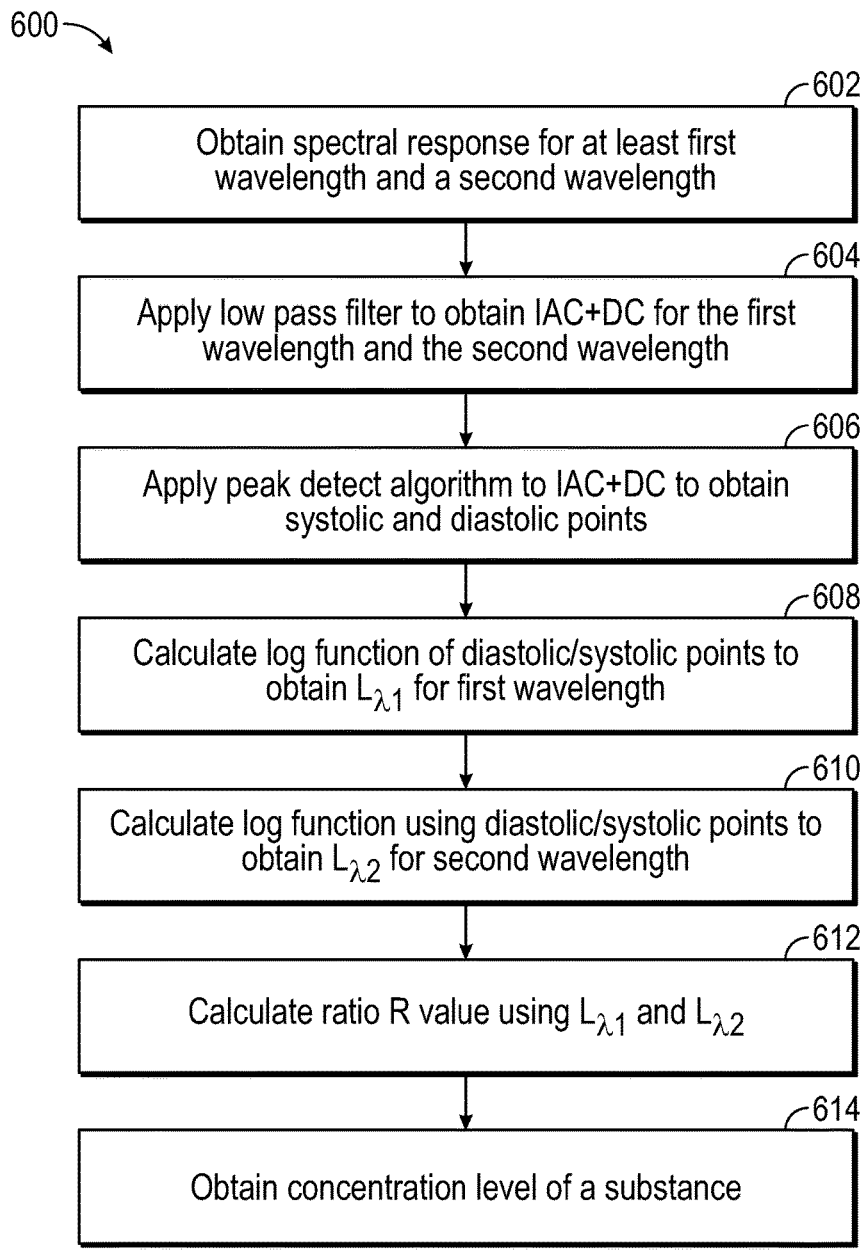
FIG. 6 illustrates a logical flow diagram of an embodiment of a method of the biosensor.

FIG. 6 illustrates a logical flow diagram of an embodiment of a method 600 of the biosensor 100. In one aspect, the biosensor 100 emits and detects light at a plurality of predetermined frequencies or wavelengths, such as approximately 940 nm, 660 nm, 390 nm, 592 nm, and 468 nm or in ranges thereof. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the user in a range of 360 nm to 410 nm including the predetermined wavelength 390 nm. For the predetermined wavelength of 940 nm, the biosensor 100 may transmit light directed at the skin tissue of the user in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 602. The spectral responses may be measured over a predetermined period (such as 300 usec.). This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The spectral responses are measured over one or more cardiac cycles. The spectral data obtained by the PPG circuit 110, such as the digital or analog spectral responses over the one or more cardiac cycles, may be processed locally by the biosensor 100 or transmitted to a central control module of a vehicle for processing.

The systolic and diastolic points of the spectral response are then determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined.

A low pass filter (such as a 5 Hz low pass filter) is applied to the spectral response signal at 604. The relative contributions of the AC and DC components are obtained $I_{AC+DC}$ and $I_{AC}$. A peak detection algorithm is applied to determine the systolic and diastolic points at 606. The systolic and diastolic points of the spectral response for each of the wavelengths may be aligned and may also be aligned with systolic and diastolic points of an arterial pulse waveform or cardiac cycle.

Beer Lambert equations are then applied as described herein. For example, the $L_\lambda$ values are then calculated for the first wavelength $\lambda_1$ at 608 and the second wavelength $\lambda_2$ at 610, wherein the $L_\lambda$ values for a wavelength equals:

$$L_\lambda = \text{Log}10\left(\frac{I\text{AC} + \text{DC}}{I\text{DC}}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response.

A ratio R of the $L_\lambda$ values at two wavelengths may then be determined at 612. For example, the ratio R may be obtained from the following:

$$\text{Ratio } R = \frac{L\lambda 1}{L\lambda 2}$$

The spectral responses may be measured and the $L_\lambda$ values and Ratio R determined continuously, e.g. every 1-2 seconds, and the obtained $L_\lambda$ values and/or Ratio R averaged over a predetermined time period, such as over 1-2 minutes. The concentration level of a substance may then be obtained from the R value and a calibration database at 614. The biosensor 100 may continuously monitor a user over 2-3 hours or continuously over days or weeks.

In one embodiment, the $R_{390,940}$ value with $L_{\lambda 1=390\,nm}$ and $L_{\lambda 2=940}$ may be non-invasively and quickly and easily obtained using the biosensor 100 to determine a concentration level of NO in blood flow of a user. In particular, in unexpected results, it is believed that the nitric oxide NO levels in the arterial blood flow is being measured at least in part by the biosensor 100 at wavelengths in the range of 380-410 and in particular at $\lambda_1=390$ nm. Thus, the biosensor 100 measurements to determine the $L_{390\,nm}$ values are the first time NO concentration levels in arterial blood flow have been measured directly in vivo. These and other aspects of the biosensor 100 are described in more detail herein with clinical trial results.

Figure 7:
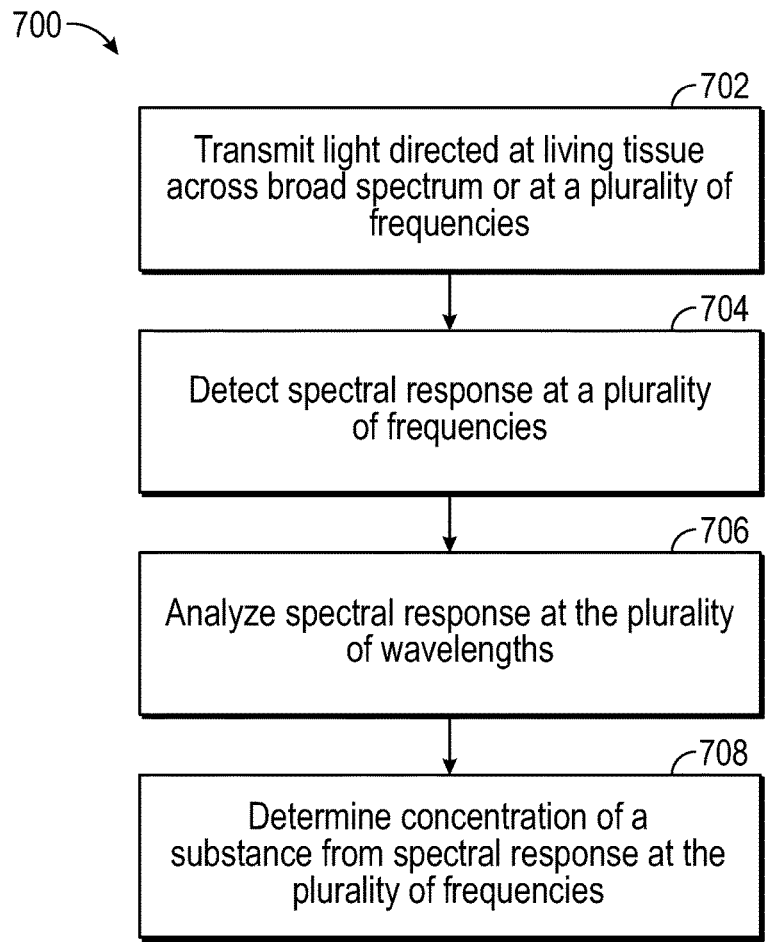
FIG. 7 illustrates a logical flow diagram of an exemplary method to determine levels of a substance in blood flow using the spectral responses at a plurality of wavelengths.

Embodiment—Determination of Concentration Level of a Substance Using Spectral Responses at a Plurality of Wavelengths FIG. 7 illustrates a logical flow diagram of an exemplary method 700 to determine levels of a substance in blood flow using the spectral responses at a plurality of wavelengths. The absorption coefficient of a substance may be sufficiently higher at a plurality of wavelengths, e.g. due to isoforms or derivative compounds. For example, the increased intensity of light at a plurality of wavelengths may be due to reflectance by isoforms or other compounds in the arterial blood flow. Another method for determining the concentration levels may then be used by measuring the spectral responses and determining L and R values at a plurality of different wavelengths of light. In this example then, the concentration level of the substance is determined using spectral responses at multiple wavelengths. An example for calculating the concentration of a substance over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ of a substance, its isoforms or other compounds including the substance are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of the substance may be isolated from the isoforms or other compounds by compensating for the concentration of the compounds. Thus, using the spectral responses at multiple frequencies provides a more robust determination of the concentration level of a substance.

In use, the biosensor 100 transmits light directed at skin tissue at a plurality of wavelengths or over a broad spectrum at 702. The spectral response of light from the skin tissue is detected at 704, and the spectral responses are analyzed at a plurality of wavelengths (and in one aspect including a range of +/−10 to 50 nm around each of the wavelengths) at 706. Then, the concentration level C of the substance may be determined using the spectral responses at the plurality of wavelengths at 708. The concentration level of the substance may be isolated from isoforms or other compounds by compensating for the concentration of the compounds.

Figure 8:
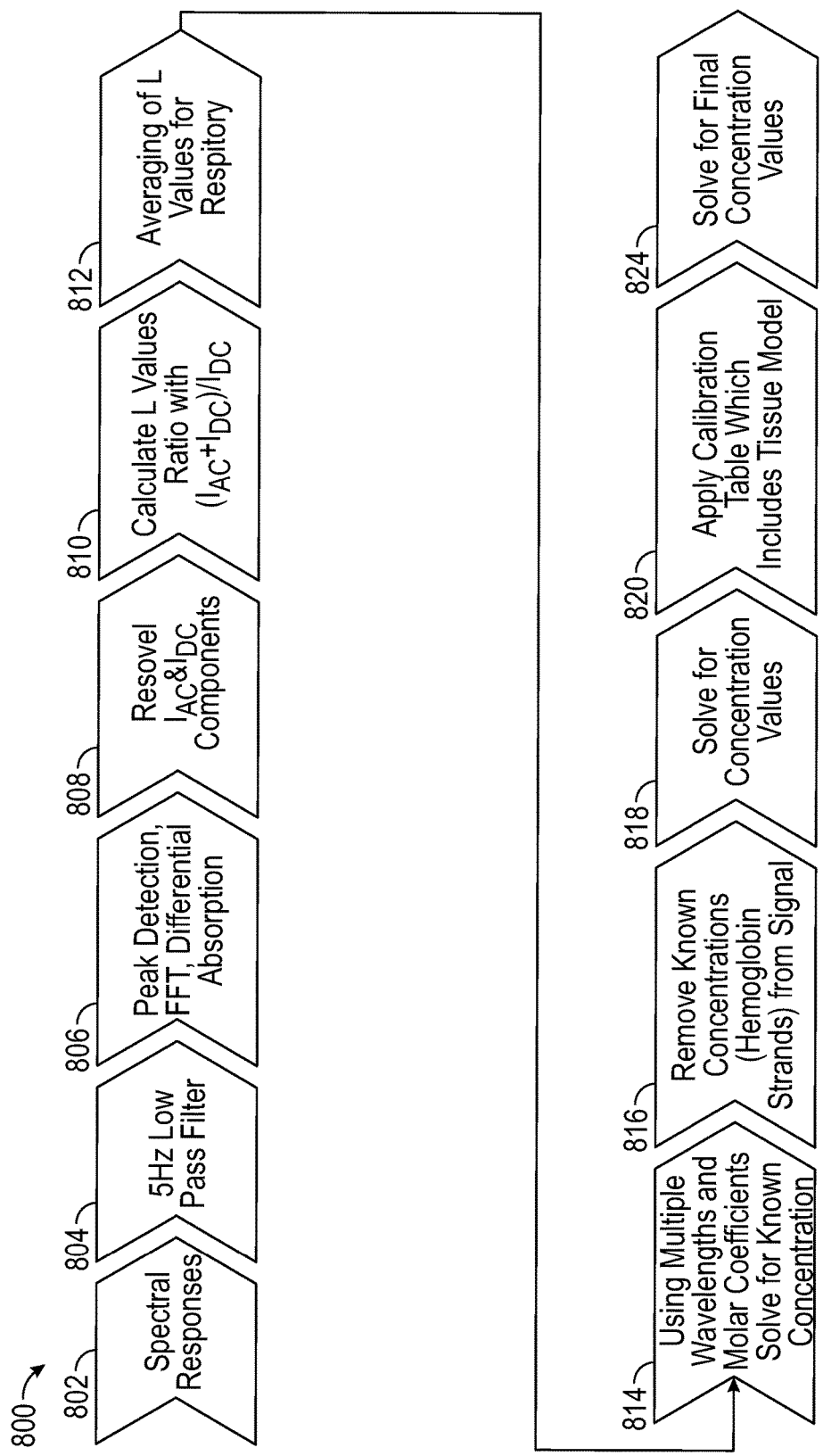
FIG. 8 illustrates a logical flow diagram of an exemplary method to determine levels of a substance using the spectral responses at a plurality of wavelengths in more detail.

FIG. 8 illustrates a logical flow diagram of an exemplary method 800 to determine levels of a substance using the spectral responses at a plurality of wavelengths in more detail. The spectral responses are obtained at 802. The spectral response signals include AC and DC components $I_{AC+DC}$. A low pass filter (such as a 5 Hz low pass filter) is applied to each of the spectral response signals $I_{AC+DC}$ to isolate the DC component of each of the spectral response signals $I_{DC}$ at 804. The AC fluctuation is due to the pulsatile expansion of the arteriolar bed due to the volume increase in arterial blood. In order to measure the AC fluctuation, measurements are taken at different times and a peak detection algorithm is used to determine the diastolic point and the systolic point of the spectral responses at 806. A Fast Fourier transform (FFT) algorithm may also be used to isolate the DC component $I_{DC}$ of each spectral response signal at 806. A differential absorption technique may also be used as described in more detail herein. The $I_{DC}$ component is thus isolated from the spectral signal at 808.

The $I_{AC+DC}$ and $I_{DC}$ components are then used to compute the L values at 810. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period) or over a plurality of cardiac cycles at 812.

In an embodiment, isoforms of a substance may be attached in the blood stream to one or more types of hemoglobin compounds. The concentration level of the hemoglobin compounds may then need to be accounted for to isolate the concentration level of the substance from the hemoglobin compounds. For example, nitric oxide (NO) is found in the blood stream in a gaseous form and also attached to hemoglobin compounds. Thus, the spectral responses obtained around 390 nm may include a concentration level of the hemoglobin compounds as well as nitric oxide. The hemoglobin compound concentration levels must thus be compensated for to isolate the nitric oxide NO concentration levels. Multiple wavelengths and absorption coefficients for hemoglobin are used to determine a concentration of the hemoglobin compounds at 614. Other methods may also be used to obtain a concentration level of hemoglobin in the arterial blood flow as well. The concentration of the hemoglobin compounds is then adjusted from the measurements at 816. The concentration values of the substance may then be obtained at 818. For example, the R values are then determined at 818.

To determine a concentration level of the substance, a calibration table or database is used that associates the obtained R value to a concentration level of the substance at 820. The calibration database correlates the R value with a concentration level. The calibration database may be generated for a specific user or may be generated from clinical data of a large sample population. For example, it is determined that the R values should correlate to similar NO concentration levels across a large sample population. Thus, the calibration database may be generated from testing of a large sample of a general population to associate R values and NO concentration levels.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and concentration levels of a substance depending on the underlying skin tissue characteristics that were measured.

The concentration level of the substance in blood flow is then obtained at 824. The concentration level may be expressed as mmol/liter, as a saturation level percentage, as a relative level on a scale, etc.

In another embodiment, in order to remove the hemoglobin concentration(s) from the original PPG signals, a mapping function may be created which is constructed through clinical data and tissue modeling. For example, known $SpO_2$ values in the infrared region and the same signals at the UV side of the spectrum are obtained. Then a linear inversion map can be constructed where the R values are input into a function and the desired concentration(s) can be determined. For example, a curve that correlates R values to concentration levels may be tabulated. A polynomial equation with multiple factors can also be used to account for different R values to represent the linear inversion map. This correlation may be derived from validated clinical data.

For example, a regression curve that correlates R values and NO concentration levels may be generated based on clinical data from a large general population. A polynomial may be derived from the curve and used to solve for an NO concentration level from the R value. The polynomial is stored in the calibration database and may be used rather than using a calibration look-up table or curve.

Embodiment—Determination of a Concentration of Hemoglobin Compounds

The Beer-Lambert theory may be generalized for a multi-wavelength system to determine a concentration of known hemoglobin species using the following matrix notation:

$$\begin{bmatrix} dA_{\lambda 1}^{LB} \\ \vdots \\ dA_{\lambda n}^{LB} \end{bmatrix} = \begin{bmatrix} \Delta l_{\lambda 1} & \cdots & 0 \\ \vdots & \ddots & \vdots \\ 0 & \cdots & \Delta l_{\lambda n} \end{bmatrix} \begin{bmatrix} \varepsilon_{\lambda 1, HbX_1} & \cdots & \varepsilon_{\lambda 1, HbX_m} \\ \vdots & \ddots & \vdots \\ \varepsilon_{\lambda n, HbX_1} & \cdots & \varepsilon_{\lambda n, HbX_m} \end{bmatrix} \cdot \begin{bmatrix} HbX_1 \\ \vdots \\ HbX_m \end{bmatrix} \cdot c(Hb),$$

wherein
$dA_\lambda^{LB}$ is a differential absorption within the Beer-Lambert model
$\varepsilon_{\lambda n, HbX1}$ is an extinction coefficient
HbX are hemoglobin fractions
$\Delta l\lambda$ is the optical path-length for wavelength $\lambda$
c(Hb) is the hemoglobin concentration This Beer-Lambert matrix equation for determining hemoglobin concentration levels may be solved when m is equal or greater than n, e.g., which means that at least four wavelengths are needed to solve for four hemoglobin species. The spectral responses at these four wavelengths may be analyzed to determine the concentration of the plurality of hemoglobin species.

Figure 9:
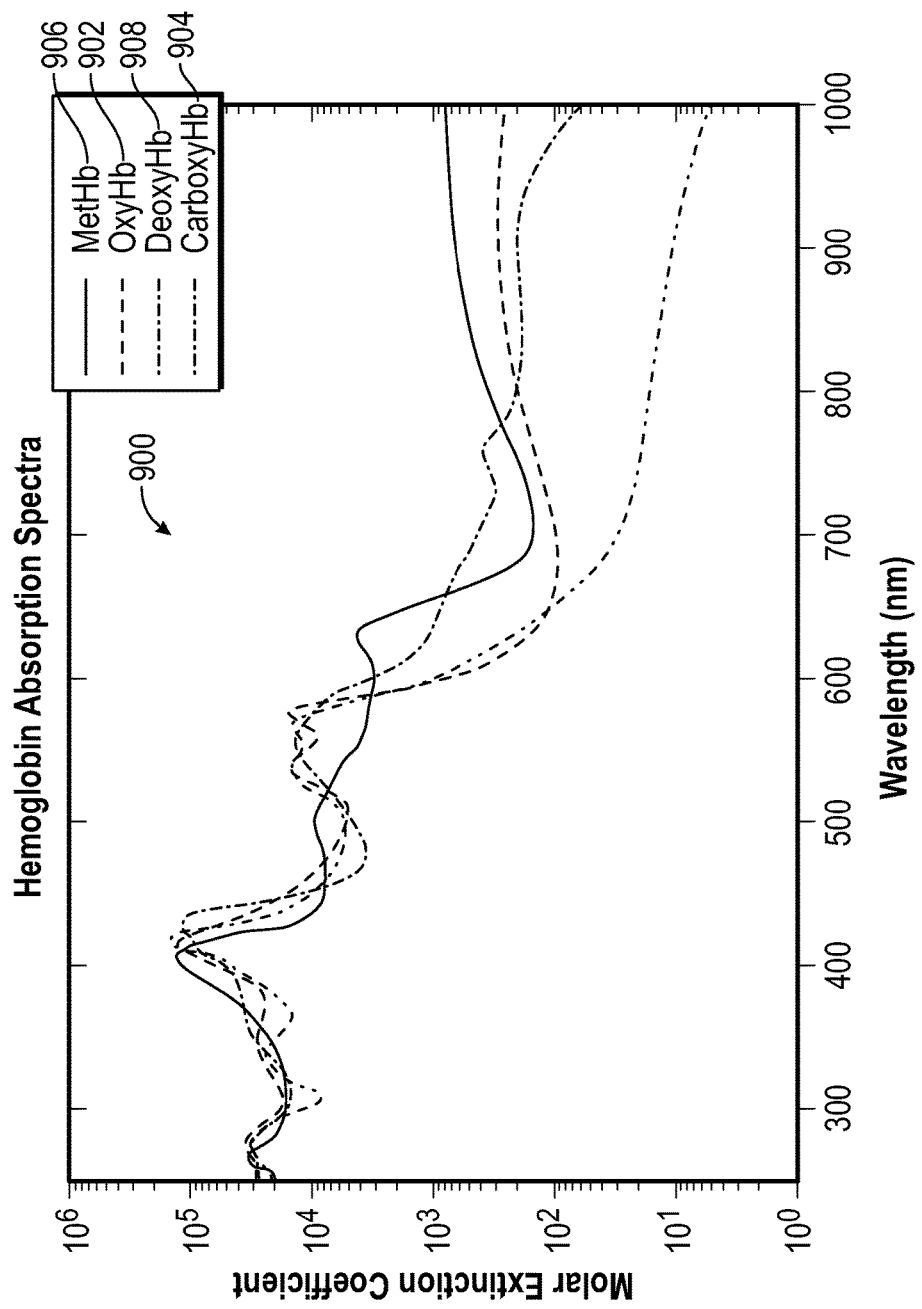
FIG. 9 illustrates a schematic block diagram of an exemplary embodiment of a graph illustrating the extinction coefficients over a range of frequencies for a plurality of hemoglobin species.

FIG. 9 illustrates a schematic block diagram of an exemplary embodiment of a graph 900 illustrating the extinction coefficients over a range of frequencies for a plurality of hemoglobin species. The hemoglobin species include, e.g., Oxyhemoglobin [HbO₂ or OxyHb] 902, Carboxyhemoglobin [HbCO or CarboxyHb] 904, Methemoglobin [HbMet or MetHb] 906, and deoxygenated hemoglobin (DeoxyHb or RHb) 908. A method for determining the relative concentration or composition of hemoglobin species included in blood is described in more detail in U.S. Pat. No. 6,104,938 issued on Aug. 15, 2000, which is hereby incorporated by reference herein.

A direct calibration method for calculating hemoglobin species may be implemented by the biosensor 100. Using four wavelengths and applying a direct model for four hemoglobin species in the blood, the following equation results:

$$HbX = \frac{a_1 * dA_1 + a_2 * dA_2 + a_3 * dA_3 + a_4 * dA_4}{b_1 * dA_1 + b_2 * dA_2 + b_3 * dA_3 + b_4 * dA_4}$$

wherein
$dA_\lambda$ is the differential absorption signal
$a_n$ and $b_n$ are calibration coefficients The calibration coefficients $a_n$ and $b_n$ may be experimentally determined over a large population average. The biosensor 100 may include a calibration database to account for variances in the calibration coefficients $a_1$ and $b_1$ (or extinction coefficients) for the hemoglobin species for various underlying tissue characteristics.

A two-stage statistical calibration and measurement method for performing PPG measurement of blood analyte concentrations may also be implemented by the biosensor 100. Concentrations of MetHb, HbO₂, RHb and HbCO are estimated by first estimating a concentration of MetHb (in a first stage) and subsequently, if the concentration of MetHb is within a predetermined range, then the estimated concentration of MetHb is assumed to be accurate and this estimated concentration of MetHb is utilized as a "known value" in determining the concentrations of the remaining analytes HbO₂, RHb and HbCO (in a second stage). This method for determining a concentration of hemoglobin species using a two stage calibration and analyte measurement method is described in more detail in U.S. Pat. No. 5,891,024 issued on Apr. 6, 1999, which is hereby incorporated by reference herein.

The concentration of the hemoglobin compounds may thus be determined. The biosensor 100 compensates for the hemoglobin concentration in determinations to obtain the concentration level of NO by the biosensor 100. Though several methods are described herein for obtaining a concentration of hemoglobin analytes, other methods or processes may be used by the biosensor 100 to determine the concentration of hemoglobin analytes or otherwise adjusting or compensating the obtained measurements to account for a hemoglobin concentration when determining the concentration levels of NO in a blood stream.

Embodiment—Determination of Concentration Levels of a Substance Using Shifts in Absorbance Peaks In another embodiment, a concentration level of a substance may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

Figure 10:
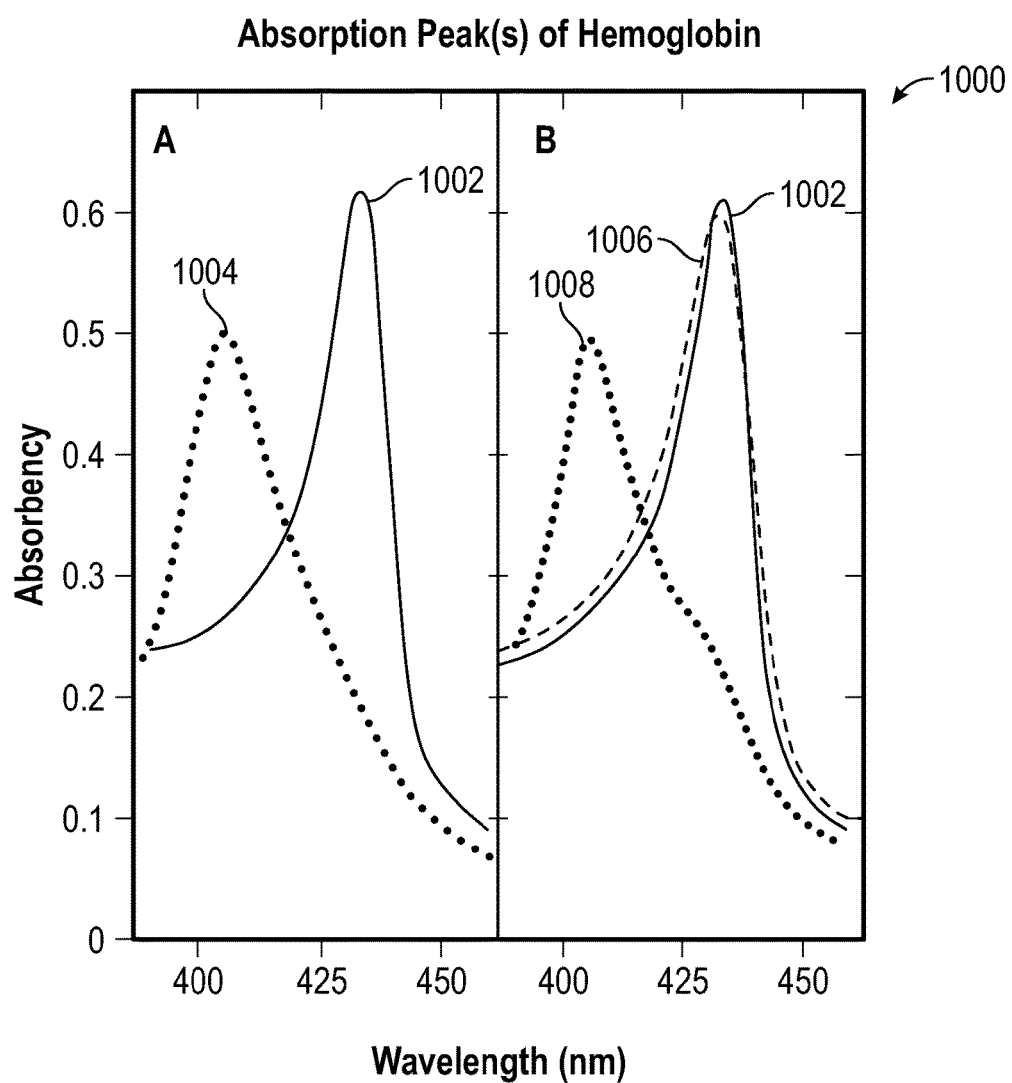
FIG. 10 illustrates a schematic block diagram of an exemplary embodiment of a graph illustrating a shift in absorbance peaks of hemoglobin in the presence of nitric oxide (NO).

FIG. 10 illustrates a schematic block diagram of an exemplary embodiment of a graph 1000 illustrating a shift in absorbance peaks of hemoglobin in the presence of NO. In graph A, the curve 1002 illustrates the absorbance spectra of reduced hemoglobin. The addition of nitric oxide (NO) shifts the absorbance spectra curve 1002 to a lower wavelength curve 1004 due to the production of methemoglobin. In graph B, the absorbance spectra curve 1002 of reduced hemoglobin is again illustrated. Endothelial cells are then added and the absorbance spectra measured again. The curve 1006 illustrates that little change occurs in the absorbance spectra curve 1002 of reduced hemoglobin in the presence of unstimulated endothelial cells. The curve 1008 illustrates the production of methemoglobin when the same dose of endothelial cells was given after stimulation of EDRF synthesis by the ionophore.

Though the absorbance spectrums shown in the graph 1000 were measured using in vitro assays, the biosensor 100 may detect nitric oxide in vivo using PPG techniques by measuring the shift in the absorbance spectra curve of reduced hemoglobin 1002 in tissue and/or arterial blood flow. The absorbance spectra curve 1002 shifts with a peak from around 430 nm to a peak around 411 nm depending on the production of methemoglobin. The greater the degree of the shift of the peak of the curve 1002, the higher the production of methemoglobin and NO concentration level. Correlations may be determined between the degree of the measured shift in the absorbance spectra curve 1002 of reduced hemoglobin to an NO concentration level. The correlations may be determined from a large sample population or for a particular user and stored in a calibration database. The biosensor 100 may thus obtain an NO concentration level by measuring the shift of the absorbance spectra curve 1002 of reduced hemoglobin. A similar method of determining shifts in an absorbance spectra may be implemented to determine a blood concentration level of other substances.

Figure 11:
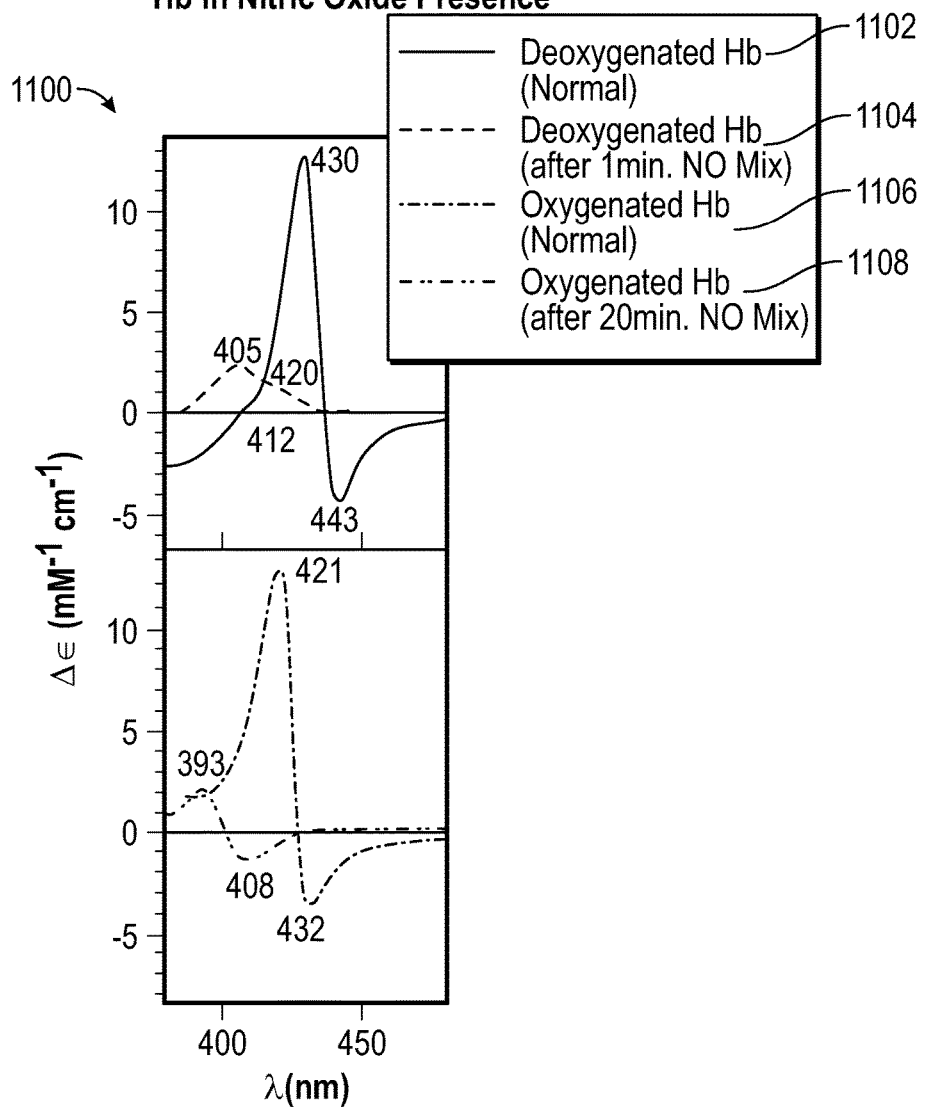
FIG. 11 illustrates a schematic block diagram of an exemplary embodiment of a graph illustrating a shift in absorbance peaks of oxygenated and deoxygenated hemoglobin (HB) in the presence of nitric oxide (NO).

FIG. 11 illustrates a schematic block diagram of an exemplary embodiment of a graph 1100 illustrating a shift in absorbance peaks of oxygenated and deoxygenated hemoglobin (HB) in the presence of nitric oxide NO. The absorbance spectra curve 1102 of deoxygenated HB has a peak of around 430 nm. After a one minute time period of exposure to a nitric oxide mixture, the absorbance spectra curve 1104 of deoxygenated HB shifted to a peak of around 405 nm. In addition, the absorbance spectra curve 1106 of oxygenated HB has a peak around 421 nm. After a twenty minute time period of exposure to a nitric oxide mixture, the absorbance spectra curve 1508 of oxygenated HB shifted to a peak of around 393 nm. The Deoxygenated Hb has an absorption peak at 430 nm (curve 1502) and in the presence of NO has a peak shift to 405 nm (curve 1504). The Oxygenated Hb has absorption peak at 421 nm (curve 1506) in presence of NO has peak shift to 393 nm (curve 1508).

Though the absorbance spectrums shown in the graph 1100 were measured using in vitro assays, the biosensor 100 may obtain an NO concentration level by measuring the shift of the absorbance spectra curve 1102 of deoxygenated hemoglobin and/or by measuring the shift of the absorbance spectra curve 1106 of oxygenated hemoglobin in vivo. The biosensor 100 may then access a calibration database that correlates the measured shift in the absorbance spectra curve 1102 of deoxygenated hemoglobin to an NO concentration level. Similarly, the biosensor may access a calibration database that correlates the measured shift in the absorbance spectra curve 1106 of oxygenated hemoglobin to an NO concentration level.

Figure 12:
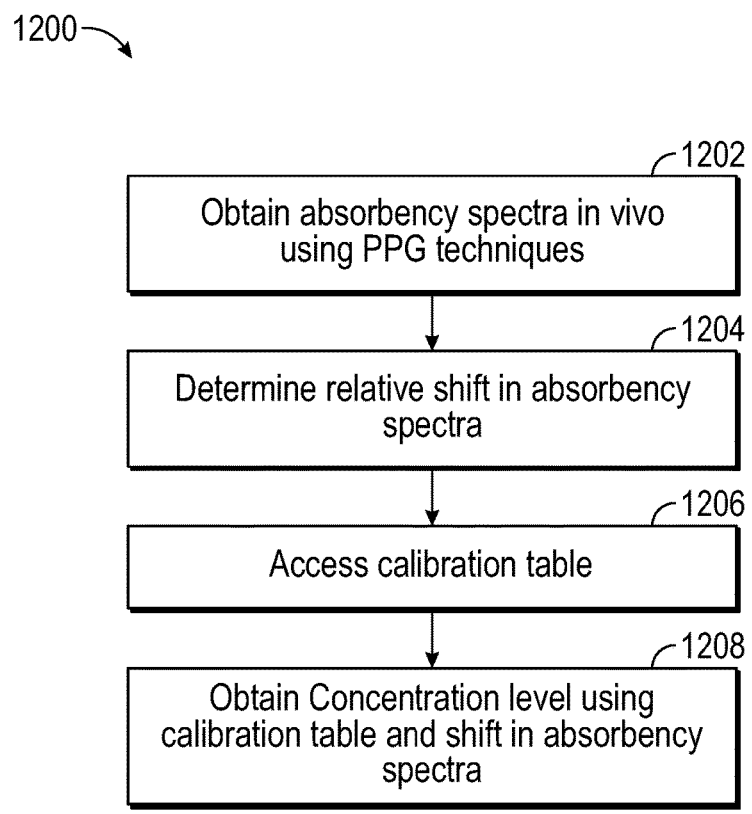
FIG. 12 illustrates a logical flow diagram of an exemplary embodiment of a method for measuring a concentration level of a substance in vivo using shifts in absorbance spectra

FIG. 12 illustrates a logical flow diagram of an exemplary embodiment of a method 1200 for measuring a concentration level of a substance in vivo using shifts in absorbance spectra. The biosensor 100 may obtain a concentration of the substance by measuring shifts in absorbance spectra of one or more substances that interact with the substance. For example, the one or more substances may include oxygenated and deoxygenated hemoglobin (HB). The PPG circuit 110 detects a spectral response at a plurality of wavelengths of the one or more substances that interact with the substance at 1202. The biosensor 100 determines the relative shift in the absorbance spectra for the substance at 1204. For example, the biosensor 100 may measure the absorbance spectra curve 1202 of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of the substance at 1206. The biosensor 100 may thus obtain a concentration level of the substance in blood flow using a calibration database and the measured relative shift in absorbance spectra at 1208.

The various methods thus include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies.

Figure 13:
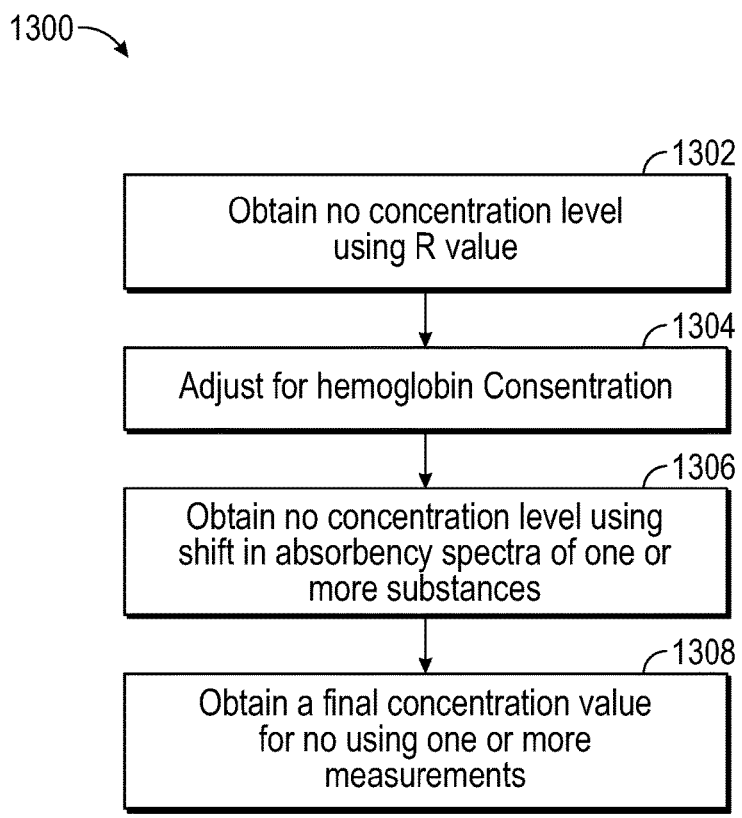
FIG. 13 illustrates a logical flow diagram of an exemplary embodiment of a method for measuring a concentration level of a substance in blood flow using one or more measurement techniques.

FIG. 13 illustrates a logical flow diagram of an exemplary embodiment of a method 1300 for measuring a concentration level of a substance in blood flow using one or more measurement techniques. In an embodiment, the biosensor 100 is configured to determine a concentration level of the substance in vivo using PPG technology and one or more measurement techniques described herein. For example, the biosensor 100 may determine an R value from L values obtained from a plurality of spectral responses at 1302. In another example, the biosensor may determine concentration level using absorption coefficients for the substance and associated isotopes and compounds over a plurality of wavelengths and adjusting or compensating for the compound concentrations (such as hemoglobin concentrations) at 1304. In another example, the biosensor 100 may determine the relative shift in the absorbance spectra for a substance (such as hemoglobin) and access a calibration database that correlates the relative shift in the absorbance spectra of the substance with a concentration level of the substance at 1306.

The biosensor 100 may use a plurality of these methods to determine a plurality of values for the concentration level of the substance at 1308. The biosensor 100 may determine a final concentration value using the plurality of values. For example, the biosensor 100 may average the values, obtain a mean of the values, etc.

The biosensor 100 may be configured for measurement on a fingertip or palm, wrist, an arm, forehead, chest, abdominal area, ear lobe, or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue. The PPG circuit 110 may adjust a power of the LEDs or a frequency or wavelength of the LEDs based on the underlying tissue. The biosensor 100 may adjust processing of the data. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor. For example, the calibration database may include different table or other correlations between R values and concentration level of a substance depending on position of the biosensor. Due to the different density of tissue and vessels, the R value obtained from measurements over an abdominal area may be different than measurements over a wrist or forehead or fingertip. The calibration database may thus include different correlations of the R value and concentration level depending on the underlying tissue. Other adjustments may also be implemented in the biosensor 100 depending on predetermined or measured characteristics of the underlying tissue of the body part.

Embodiment—Clinical Data

Figure 14:
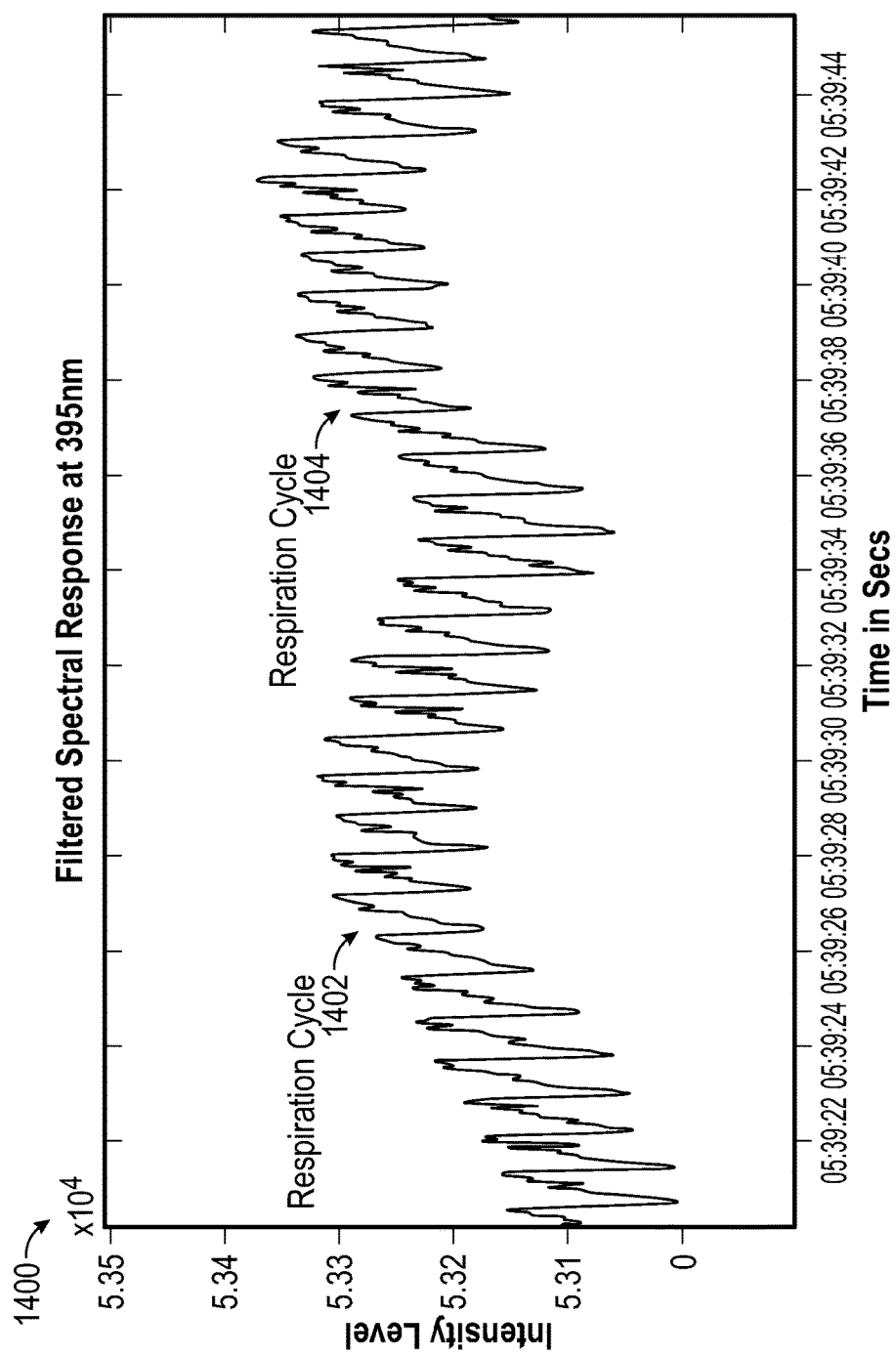
FIG. 14 illustrates a schematic drawing of an exemplary embodiment of results of a spectral response obtained using an embodiment of the biosensor from a user.

FIG. 14 illustrates a schematic drawing of an exemplary embodiment of results of a spectral response 1400 obtained using an embodiment of the biosensor 100 from a user. The spectral response 1400 was obtained at a wavelength of around 395 nm and is illustrated for a time period of about 40 seconds. The spectral response 1400 was filtered using digital signal processing techniques to eliminate noise and background interference to obtain the filtered spectral response 1400. A first respiration cycle 1402 and a second respiration cycle 1404 may be obtained by measuring the low frequency fluctuation of the filtered spectral response 1400. Due to this low frequency fluctuation, the biosensor 100 may obtain a respiratory rate of a user from the spectral response 1400. A heart rate may also be determined from the spectral response 1400 as well. For example, the biosensor 100 may determine the time between diastolic points or between systolic points to determine a time period of a cardiac cycle.

Figure 15:
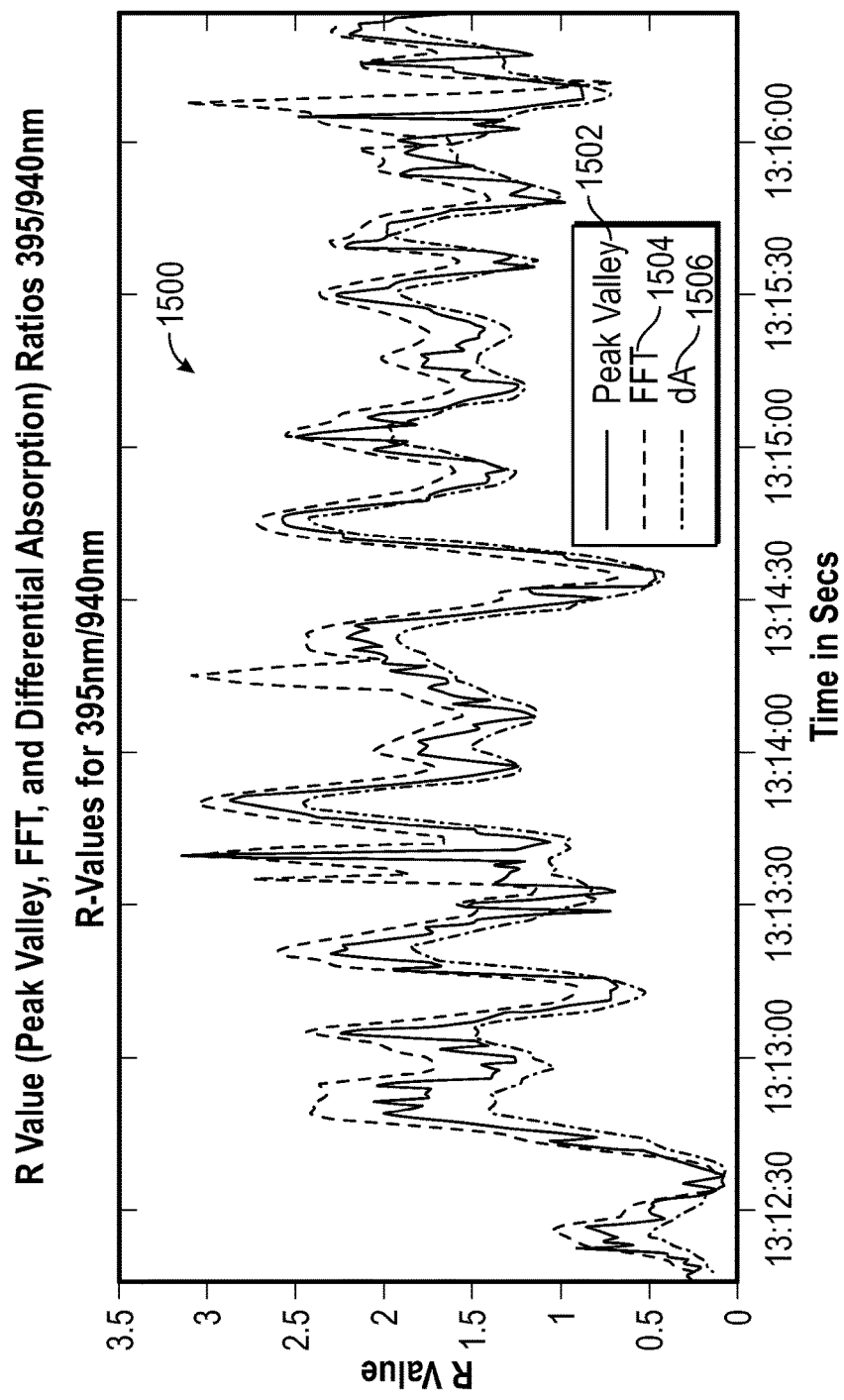
FIG. 15 illustrates a schematic drawing of an exemplary embodiment of results of R values determined using a plurality of methods.

FIG. 15 illustrates a schematic drawing of an exemplary embodiment of results of R values 1500 determined using a plurality of methods. The R values 1500 corresponding to the wavelengths of 395 nm/940 nm is determined using three methods. The R Peak Valley curve 1502 is determined using the Ratio $$R = \frac{L395}{L940}$$

as described hereinabove. The R FFT curve 1504 is obtained using FFT techniques to determine the $I_{DC}$ values of the spectral responses. The R differential absorption curve 1506 is determined using the shift in absorbance spectra as described hereinabove. As seen in FIG. 15, the determination of the R values using the three methods provides similar results, especially when averaged over a period of time. A mean or average of the R values 1502, 1504 and 1506 may be calculated to obtain a final R value or one of the methods may be preferred depending on the positioning of the biosensor or underlying tissue characteristics.

Figure 16:
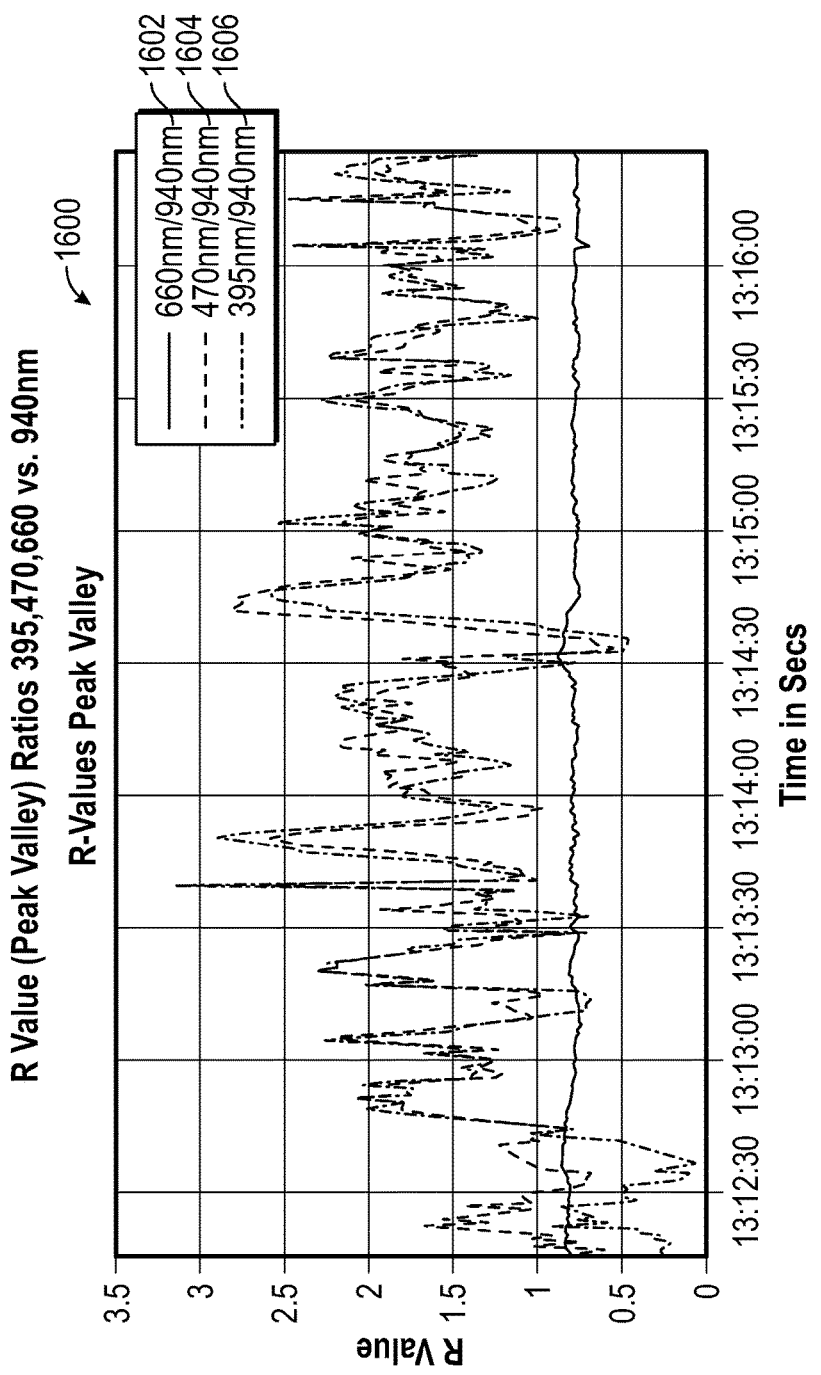
FIG. 16 illustrates a schematic drawing of an exemplary embodiment of results of R values for a plurality of wavelength ratios.

FIG. 16 illustrates a schematic drawing of an exemplary embodiment of results of R values 1600 for a plurality of wavelength ratios. The R values for 395 nm/940 nm 1606, the R values for 470 nm/940 nm 1604 and the R values for 660 nm/940 nm 1606 are shown over a time period of about 4 seconds.

Figure 17A:
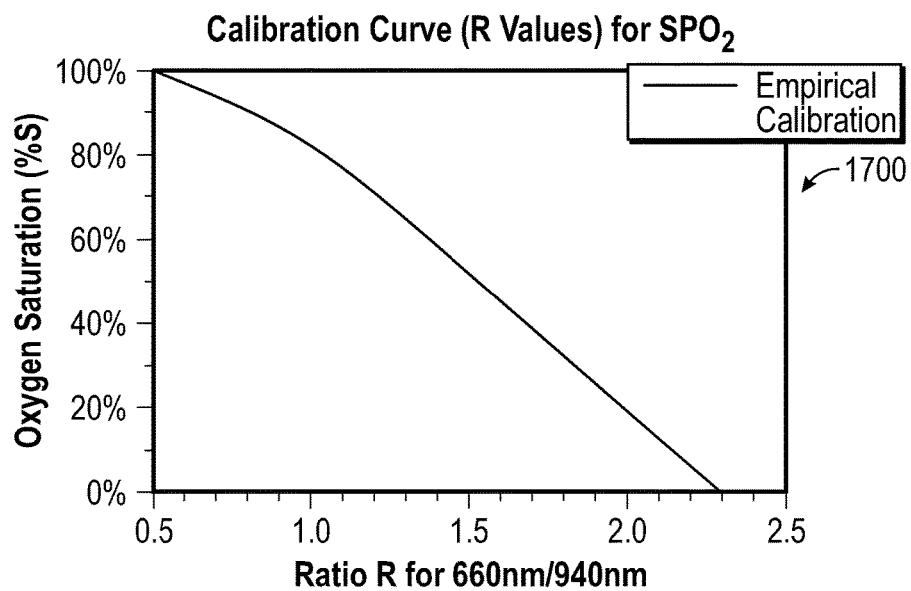
FIG. 17A illustrates a schematic drawing of an exemplary embodiment of an empirical calibration curve for correlating oxygen saturation levels ($SpO_2$) with R values.

FIG. 17A illustrates a schematic drawing of an exemplary embodiment of an empirical calibration curve 1700 for correlating oxygen saturation levels (SpO$_2$) with R values. The calibration curve 1700 may be included as part of the calibration database for the biosensor 100. For example, the R values may be obtained for $L_{660\ nm}/L_{940\ nm}$. In one embodiment, the biosensor 100 may use a light source in the 660 nm wavelength or in a range of +/−50 nm to determine SpO$_2$ levels, e.g. rather than a light source in the IR wavelength range. The 660 nm wavelength has been determined in unexpected results to have good results in measuring oxygenated hemoglobin, especially in skin tissue with fatty deposits, such as around the abdominal area.

Figure 17B:
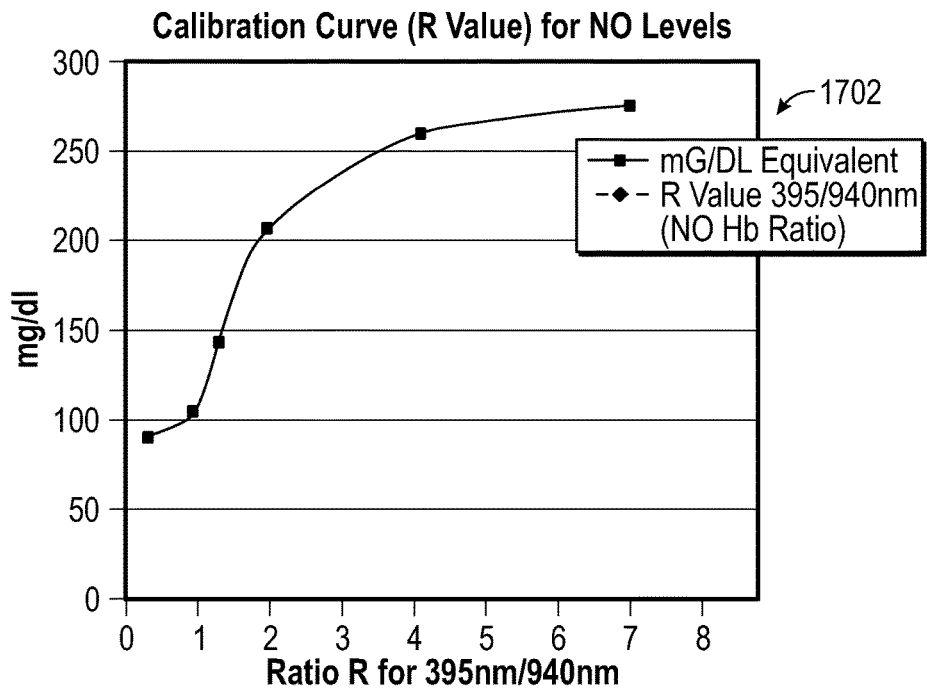
FIG. 17B illustrates a schematic drawing of an exemplary embodiment of an empirical calibration curve for correlating NO levels (mg/dl) with R values.

FIG. 17B illustrates a schematic drawing of an exemplary embodiment of an empirical calibration curve 1702 for correlating NO levels (mg/dl) with R values. The calibration curve 1702 may be included as part of the calibration database for the biosensor 100. For example, the R values may be obtained in clinical trials from measurements of $L_{395\ nm}/L_{940\ nm}$ and the NO levels of a general sample population. The NO levels may be measured using one or more other techniques for verification to generate such a calibration curve 1702. This embodiment of the calibration curve 1702 is based on limited clinical data and is for example only. Additional or alternative calibration curves 1702 may also be derived from measurements of a general population of users at one or more different positions of the biosensor 100. For example, a first calibration curve may be obtained at a forehead, another for an abdominal area, another for a fingertip, etc.

From the clinical trials, the L values obtained at wavelengths around 390 nm (e.g. 380-410) are measuring NO levels in the arterial blood flow. The R value for $L_{390}/L_{940\ nm}$ may thus be used to obtain NO levels in the pulsating arterial blood flow. From the clinical trials, it seems that the NO levels are reflected in the R values obtained from $L_{390\ nm}/L_{940\ nm}$ and wavelengths around 390 nm such as $L_{395\ nm}/L_{940\ nm}$. The NO levels may thus be obtained from the R values and a calibration database that correlates the R value with known concentration level of NO for the user or for a large general population.

In other embodiments, rather than $L_{\lambda1}$=390 nm, the L value may be measured at wavelengths in a range from 410 nm to 380 nm, e.g., as seen in the graphs wherein $L_{\lambda1}$=395 nm is used to obtain a concentration level of NO. In addition, $L_{\lambda2}$ may be obtained at any wavelength at approximately 660 nm or above. Thus, R obtained at approximately L$\lambda$1=380 nm-400 nm and L$\lambda$2≥660 nm may also be obtained to determine concentration levels of NO.

The concentration level of NO may be correlated to a diabetic risk or to blood glucose levels using a calibration database.

Embodiment—Measurements of Other Substances

Using similar principles described herein, the biosensor 100 may measure concentration levels or indicators of other substances in pulsating blood flow. For example, absorption coefficients for one or more frequencies that have an intensity level responsive to concentration level of substance may be determined. The biosensor 100 may then detect the substance at the determined one or more frequencies as described herein and determine the concentration levels using the Beer-Lambert principles and the absorption coefficients. The L values and R values may be calculated based on the obtained spectral response. In one aspect, the biosensor 100 may detect various electrolyte concentration levels or blood analyte levels, such as bilirubin and sodium and potassium. In another aspect, the biosensor 100 may detect sodium NACL concentration levels in the arterial blood flow to determine dehydration. In yet another aspect, the biosensor 100 may be configured to detect proteins or abnormal cells or other elements or compounds associated with cancer. In another aspect, the PPG sensor may detect white blood cell counts. In another aspect, the biosensor may detect blood alcohol levels.

For example, the biosensor 100 may also determine alcohol levels in the blood using wavelengths at approximately 390 nm and/or 468 nm. For example, an $R_{468,940}$ value for at least L468 nm/L940 nm may be used as a liver enzyme indicator, e.g. P450 enzyme indicator. The P450 liver enzyme is generated in response to alcohol levels. Thus, the measurement of the spectral response for the wavelength at approximately 468 nm may be used to obtain blood alcohol levels from the concentration levels of P450 and a calibration database.

In another embodiment, an R592,940 value for at least L592 nm/L940 nm may be used as a digestive indicator to measure digestive responses, such as phase 1 and phase 2 digestive stages. In another aspect, the biosensor 100 may detect white blood cell counts or concentration levels in arterial blood flow using similar PPG techniques. The presence of white blood cell counts may indicate the presence of infection.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100. Since the biosensor 100 may operate in multiple frequencies, various health monitoring tests may be performed concurrently.

Figure 18:
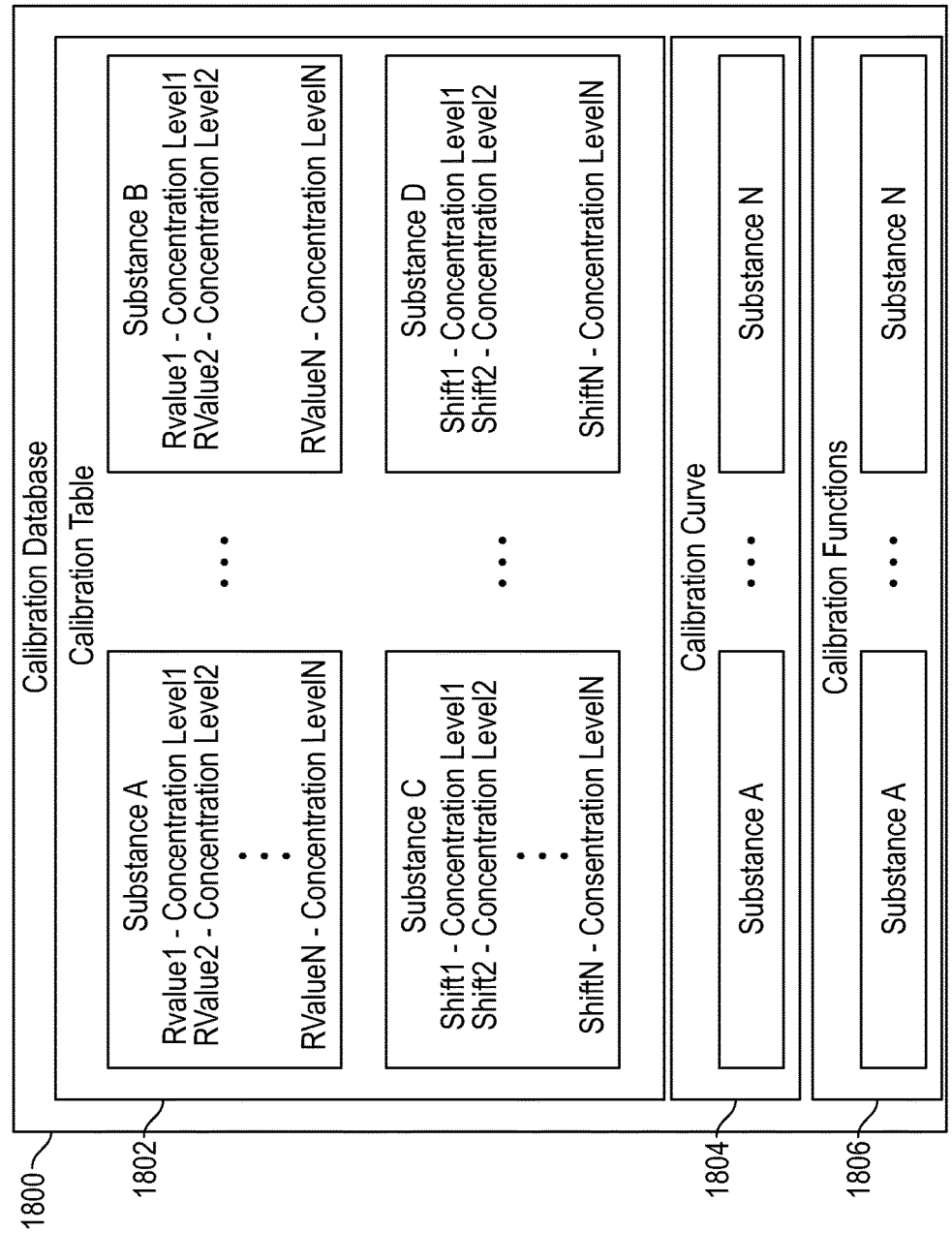
FIG. 18 illustrates a schematic block diagram of an embodiment of a calibration database.

FIG. 18 illustrates a schematic block diagram of an embodiment of a calibration database 1800. The calibration database 1800 includes one or more calibration tables 1802, calibration curves 1804 or calibration functions 1806 for correlating obtained values to concentration levels of one or more substances A-N. The concentration level of the substances may be expressed in the calibration tables 1802 as units of mmol/liter, as a saturation level percentage (SpNO %), as a relative level on a scale (e.g., 0-10), etc.

The calibration database 1800 may also include one or more calibration tables for one or more underlying skin tissue types. In one aspect, the calibration database 1800 may correlate an R value to a concentration level of a substance for a plurality of underlying skin tissue types.

In another aspect, a set of calibration tables 1802 may correlate an absorption spectra shift to a concentration level of one or more substances A-N. For example, a first table may correlate a degree of absorption spectra shift of oxygenated hemoglobin to NO concentration levels. The degree of shift may be for the peak of the absorbance spectra curve of oxygenated hemoglobin from around 421 nm. In another example, the set of table 1802 may correlate a degree of absorption spectra shift of deoxygenated hemoglobin to NO concentration levels. The degree of shift may be for the peak of the absorbance spectra curve of deoxygenated hemoglobin from around 430 nm.

The calibration database 1800 may also include a set of calibration curves 1804 for a plurality of substances A-N. The calibration curves may correlate L values or R values or degree of shifts to concentration levels of the substances A-N.

The calibration database 1800 may also include calibration functions 1806. The calibration functions 1806 may be derived (e.g., using regressive functions) from the correlation data from the calibration curves 1804 or the calibration tables 1802. The calibration functions 1806 may correlate L values or R values or degree of shifts to concentration levels of the substances A-N for one or more underlying skin tissue types.

Figure 19:
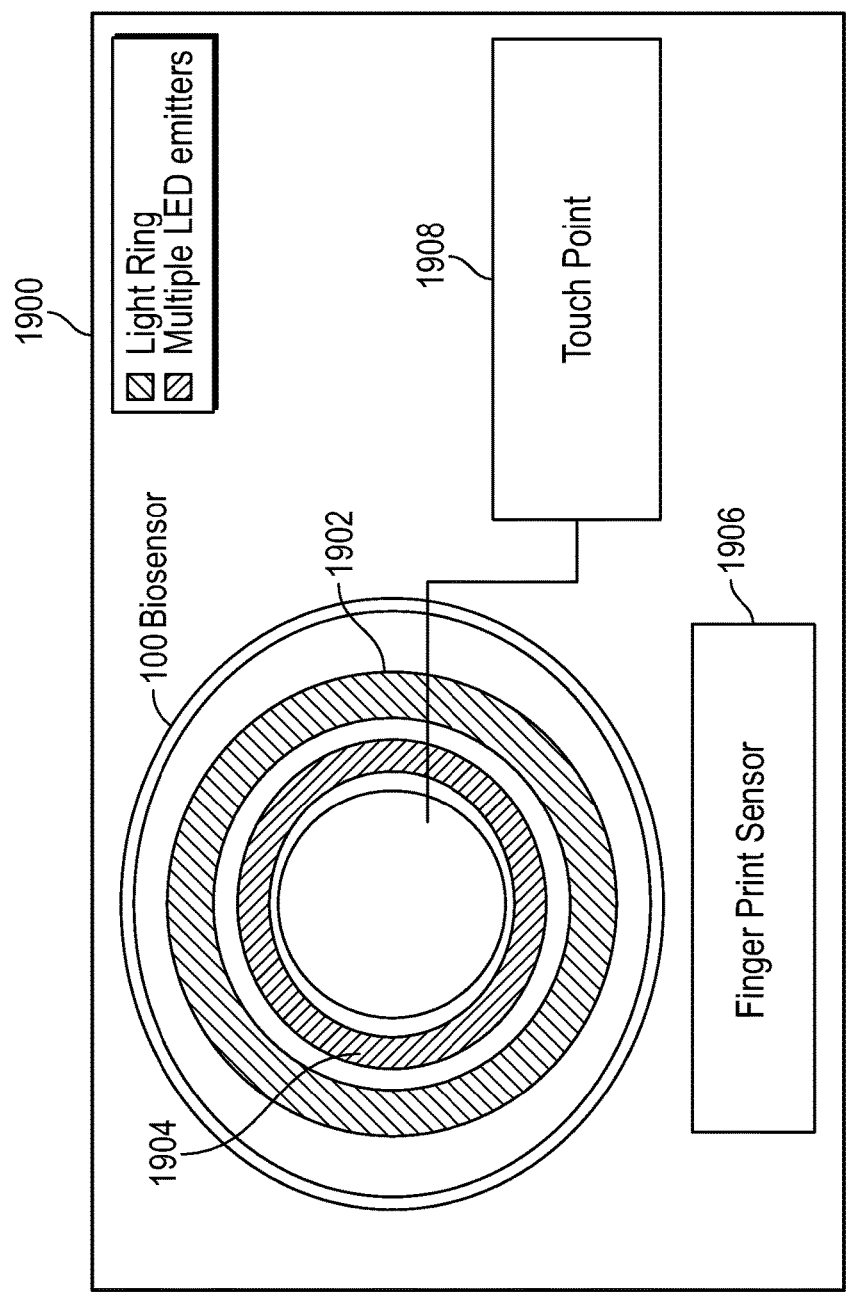
FIG. 19 illustrates a schematic block diagram of an embodiment of control button including a biosensor.

FIG. 19 illustrates a schematic block diagram of an embodiment of control button 1900 including a biosensor 100. The control button 1900 may be integrated in a key fob or as part of controls in a vehicle or on a steering wheel, parking brake, key pad, or other part of a vehicle. The biosensor 100 includes a PPG circuit 110 with a first set of LEDs 1904. The first set of LEDs 1904 may be used to emit light that is reflected from skin of a user and detected to obtain spectral responses at one or more wavelengths. The first set of LEDs 1904 may also be used as a visible indicator of one or more modes of operation of the biosensor 100 or as a feedback signal.

The control button 1900 may alternatively or additionally include a second set of one or more LEDs 1902, e.g. positioned in another light ring 1902. The second set of LEDs 1902 may also be used as a visible indicator of one or more modes of operation or as a feedback signal. For example, the light ring 1902 may flash to indicate pressure on the touch point 1908 may need to increase or decrease. The LEDs 1902 may also generate an indicator of detected heart beats. For example, the light ring 1902 may flash to indicate each detected cardiac cycle or heart beat when measurement is in progress.

The control button 1900 further includes a touch point 1908. The touch point 1908 is a pressure sensitive pad for receiving a fingertip (including a thumb tip or other fingertip). The PPG circuit 110 is configured to measure spectral responses of light reflected from a fingertip positioned on the touch point 1908. The touch point 1908 may determine a pressure applied to the touch point 1908 and provide feedback to a user to increase or decrease the applied pressure.

The control button 1900 may also include a fingerprint sensor 1906 configured to obtain a fingerprint for authentication of a user. The fingerprint sensor 1906 may be implemented using the same set of LEDs 1904 and photodetectors as the bio sensor 100.

Figure 20:
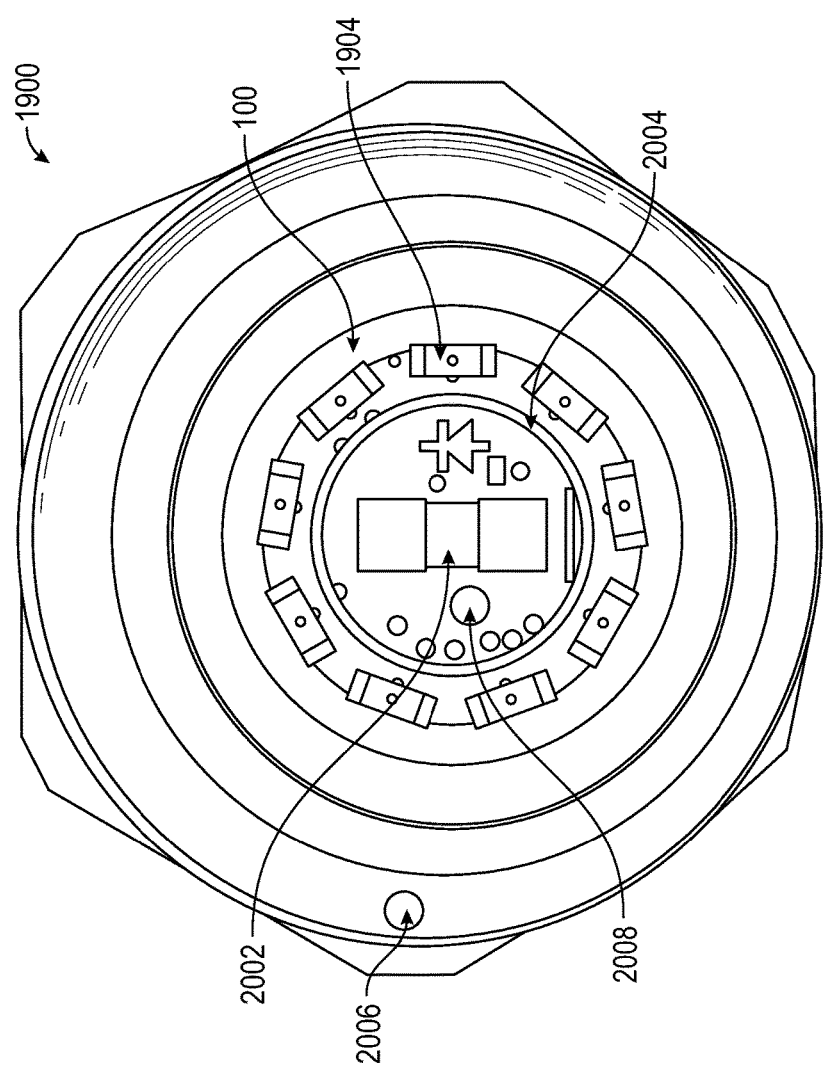
FIG. 20 illustrates a cross-sectional view of a biosensor integrated in a control button of a vehicle.

FIG. 20 illustrates a cross-sectional view of a biosensor 100 integrated in a control button 1900 of a vehicle. In this example, the control button 2000 includes an ignition button though it may be included in other types of controls of the vehicle. The control button 2000 includes the PPG circuit 110 with a plurality of LEDs 1904 positioned in a circular ring. A light gasket 2004 may illuminate the touch point 1908 positioned over the photodetector 2002. The control button 2000 may further include an air intake portal 2008 and outtake portal 2006 of an atmospheric gas sensor 116.

Figure 21A:
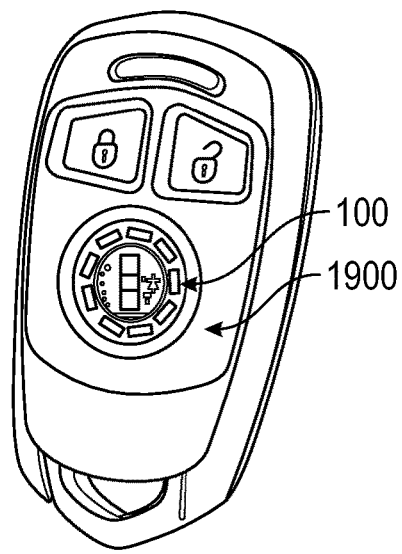
FIG. 21A illustrates a cross-sectional view of a biosensor integrated in a control button of key fob.
Figure 21B:
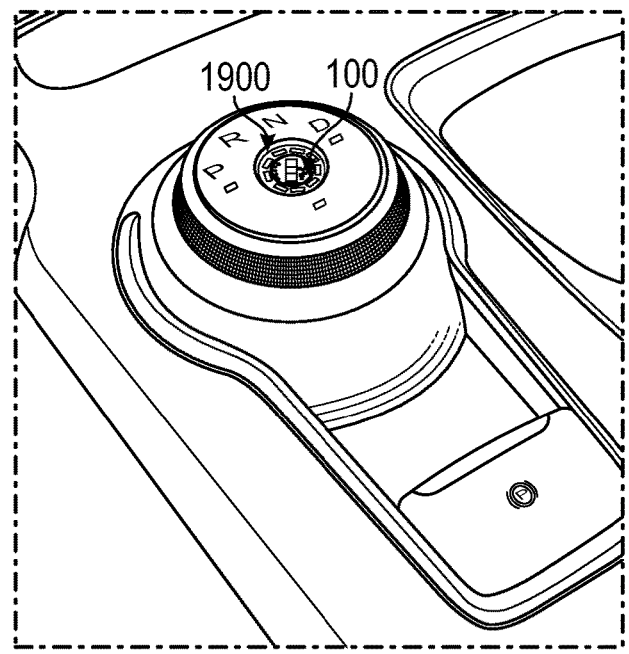
FIG. 21B illustrates a cross-sectional view of a biosensor integrated in a control button for shifting gears of a vehicle.

FIG. 21A illustrates a cross-sectional view of a biosensor 100 integrated in a control button 1900 of key fob. FIG. 21B illustrates a cross-sectional view of a biosensor 100 integrated in a control button 1900 for shifting gears of a vehicle. The control button 1900 may be integrated on a steering wheel, audio/visual controls, climate controls, gear shift, or other surfaces or controls of a vehicle.

Figure 22:
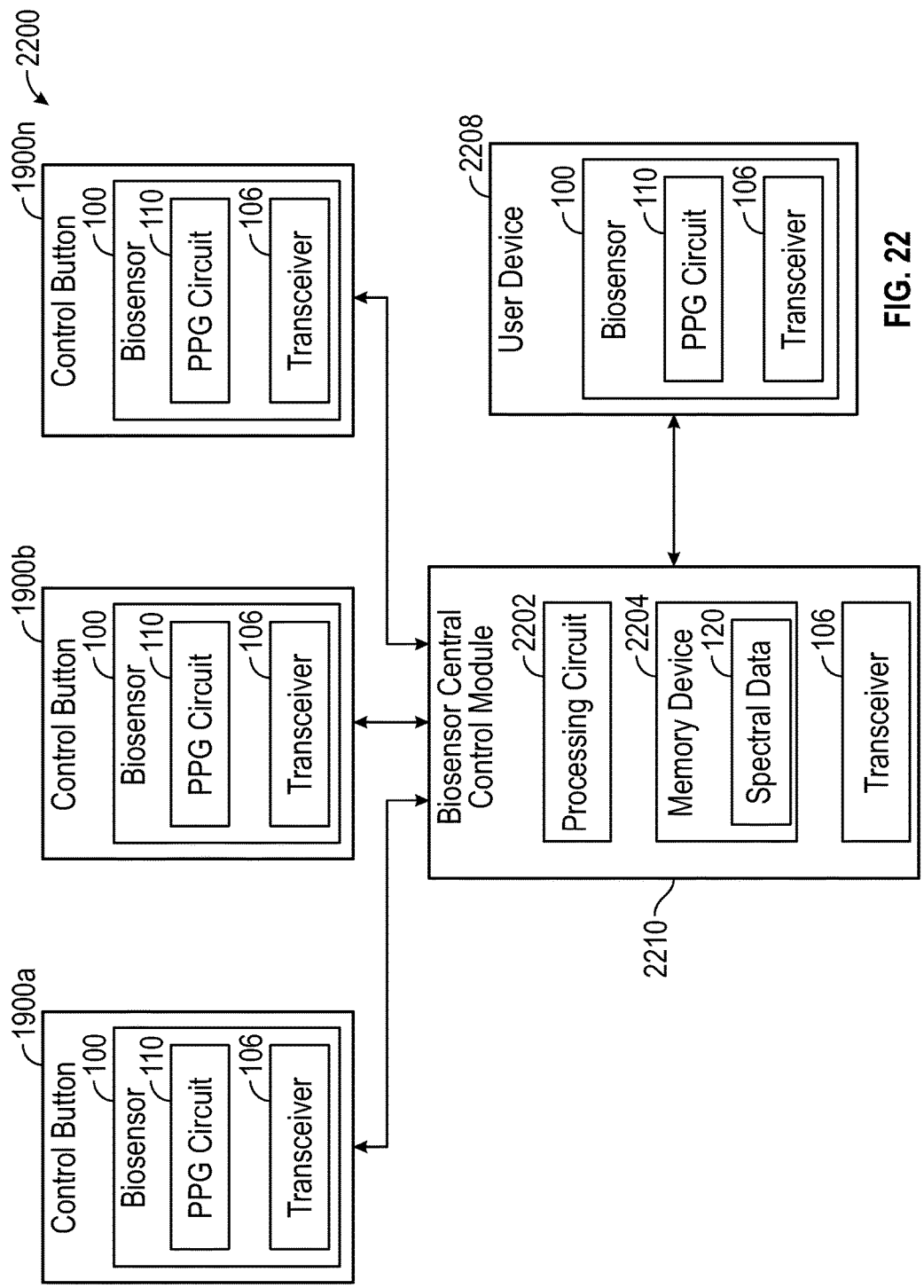
FIG. 22 illustrates a schematic block diagram of an embodiment of a vehicle health monitoring system.

FIG. 22 illustrates a schematic block diagram of an embodiment of a vehicle health monitoring system 2200. The vehicle health monitoring system 2200 includes a biosensor central control module 2210 integrated in a vehicle. The biosensor central control module 2210 includes a processing circuit 2202 and memory device 2204. In one aspect, the memory device 2204 may include one or more non-transitory processor readable memories that store instructions which when executed by the one or more processing circuits 2202, causes the one or more processing circuits 2202 to perform one or more functions described herein. The processing circuit 2202 may be co-located with one or more of the other circuits of the biosensor central control module 2210 in a same physical circuit board or located separately in a different circuit board or encasement.

The biosensor central control module 2210 includes a transceiver 106. The transceiver 106 may include a wireless or wired transceiver configured to communicate with a vehicle or one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 106 may also include a wired transceiver interface, e.g., a USB port or other type of wired connection, for communication with one or more other devices over a LAN, MAN and/or WAN. The transceiver 106 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol.

The biosensor central control module 2210 is configured to communicate with a plurality of biosensors 100. The biosensors 100 may be integrated in a plurality of control buttons 1900*a-n* of vehicle. For example, the control buttons 1900*a-n* may be integrated in a key fob, key pad on an exterior door, a gear shift, a steering wheel, an ignition control, parking brake, audio/visual control, or other surface of a vehicle. In addition, one of the biosensors 100 may be integrated in a user device 2208. A user device includes a smart phone, smart watch, laptop, smart pad or other portable user device.

The plurality of biosensors 100 obtain spectral data 120, e.g. filtered or processed digital spectral responses over one or more cardiac cycles of a user. The plurality of biosensors 100 communicate the spectral data 120 to the biosensor central control module 2210. The biosensor central control module 2210 processes the spectral data 120 to obtain health data, such as vitals of the user, including heart rate, respiration rate and oxygen saturation levels. The biosensor central control module 2210 may also obtain other health data such as concentration levels of one or more substances in blood flow of the user or alertness of the user.

The biosensor central control module 2210 may use spectral data from a plurality of the biosensors obtained from a user within a predetermined measurement period. For example, the spectral data may need to be obtained within a one minute, five minute or ten minute measurement period to be combined with other spectral data. By combining the spectral data from the plurality of biosensors, the biosensor central control module 2210 is able to obtain spectral data of a user over additional cardiac cycles or respiration cycles. For example, a first biosensor 100 may obtain spectral data of a user over a single cardiac cycle. A second biosensor 100 may obtain spectral data of the user over two cardiac cycles. A third biosensor 100 may obtain spectral data over two additional cardiac cycles. The spectral data of any one of the biosensors 100 over a single cardia cycle or two cardiac cycles is insufficient to obtain the health information of the user, such as heart rate, respiration rate or SpO$_2$ within acceptable tolerance limits.

In an embodiment, the biosensor central control module 2210 may receive the spectral data of the biosensors and then combine the spectral data from the plurality of biosensors. The biosensor central control module 2210 is then able to process the spectral data over a combined five cardiac cycles. The combined spectral data may then be sufficient to obtain a heart rate or respiration rate or oxygen saturation level within acceptable tolerance limits.

Figure 23:
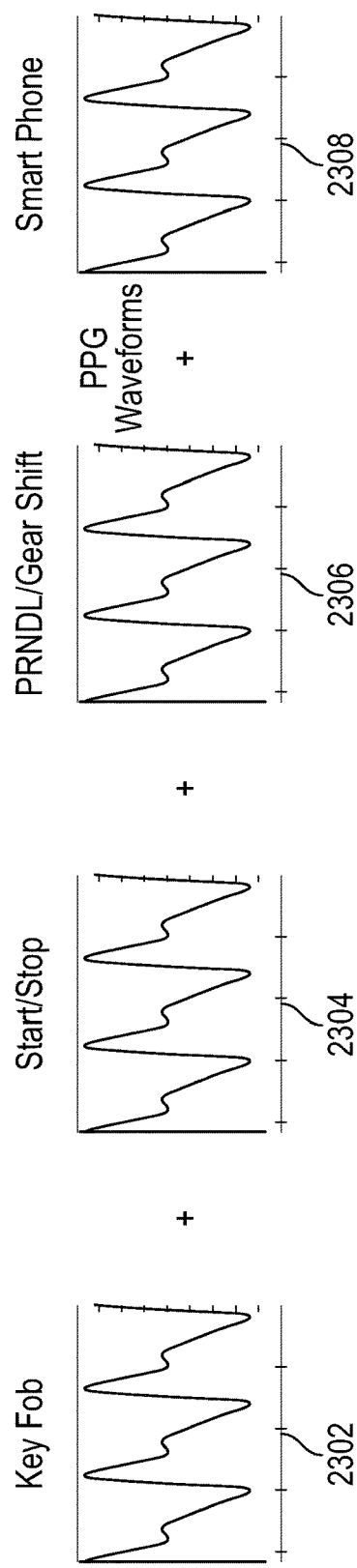
FIG. 23 illustrates a schematic block diagram of an embodiment of spectral data from a plurality of biosensors.

FIG. 23 illustrates a schematic block diagram of an embodiment of spectral data from a plurality of biosensors 100. The spectral data is for illustrative purposes only. In this illustration, spectral data including PPG waveforms is obtained from a plurality of biosensors 100 at different physical locations. For example, spectral data 2302 including PPG waveforms is obtained from a biosensor 100 integrated on a key fob. Spectral data 2304 including PPG waveforms is obtained from a biosensor 100 integrated on an ignition control. Spectral data 2306 including PPG waveforms is obtained from a biosensor 100 integrated on a gear shift. Spectral data 2308 including PPG waveforms is obtained from a biosensor 100 integrated in a user device 2208, such as a smart phone.

The PPG waveforms from the plurality of biosensors may be obtained at a same wavelength and be combined to generate a spectral response at that wavelength. In addition or alternatively, the PPG waveforms may be obtained at different wavelengths and combined to determine an R ratio.

For example, the PPG waveforms from the plurality of biosensors may be combined to determine vitals of a user, such as the heart rate or respiration rate of the user. For example, the PPG waveforms obtained at a same wavelength are combined to determine a time period between cardiac cycles and obtain a heart rate. In another example, the low frequency fluctuation of cardiac cycles measured in the combined PPG waveforms is used to determine a respiration rate. In another example, the PPG waveforms from plurality of biosensors may be combined to determine an average R value over a measurement period and a concentration level of a substance in blood flow.

The spectral data from a plurality of biosensors 100 may thus be combined to obtain health information of a user. A user may only touch a control button 1900 for a short time period such that the biosensor 100 may only obtain a spectral response at one or more wavelengths over a short measurement period. For example, a user may touch a key fob for a couple of seconds to open a vehicle and then touch the ignition control for a couple of seconds to start the vehicle and then touch a gear shift for another couple of seconds to shift from park. Each of the biosensors 100 may thus only obtain spectral data of the user for one or two seconds. The spectral data of any of the individual biosensors alone may not be sufficient to obtain health information of a user, such as heart rate or respiration rate or blood oxygen levels. However, the combined spectral data from the plurality of biosensors 100 may be sufficient to obtain the health information. The user is thus not inconvenienced by having to press and hold a single biosensor 100 for 5-10 seconds to obtain health information. In addition, the spectral data may continue to be collected as the user touches control buttons 1900 in the vehicle.

In addition, the quality of the PPG waveforms may vary in the spectral data received from the plurality of biosensors. For example, spectral data from a first biosensor may include a first set of PPG waveforms with only one or two waveforms of sufficient quality for processing. In addition, spectral data from a second biosensor may include a second set of PPG waveforms with only three or four waveforms of sufficient quality for processing. The PPG waveforms of sufficient quality may be combined from the first and second biosensor. The combined PPG waveforms may thus be of sufficient quality and number to obtain a heart rate, respiration rate, oxygen saturation level or other health information.

Figure 24:
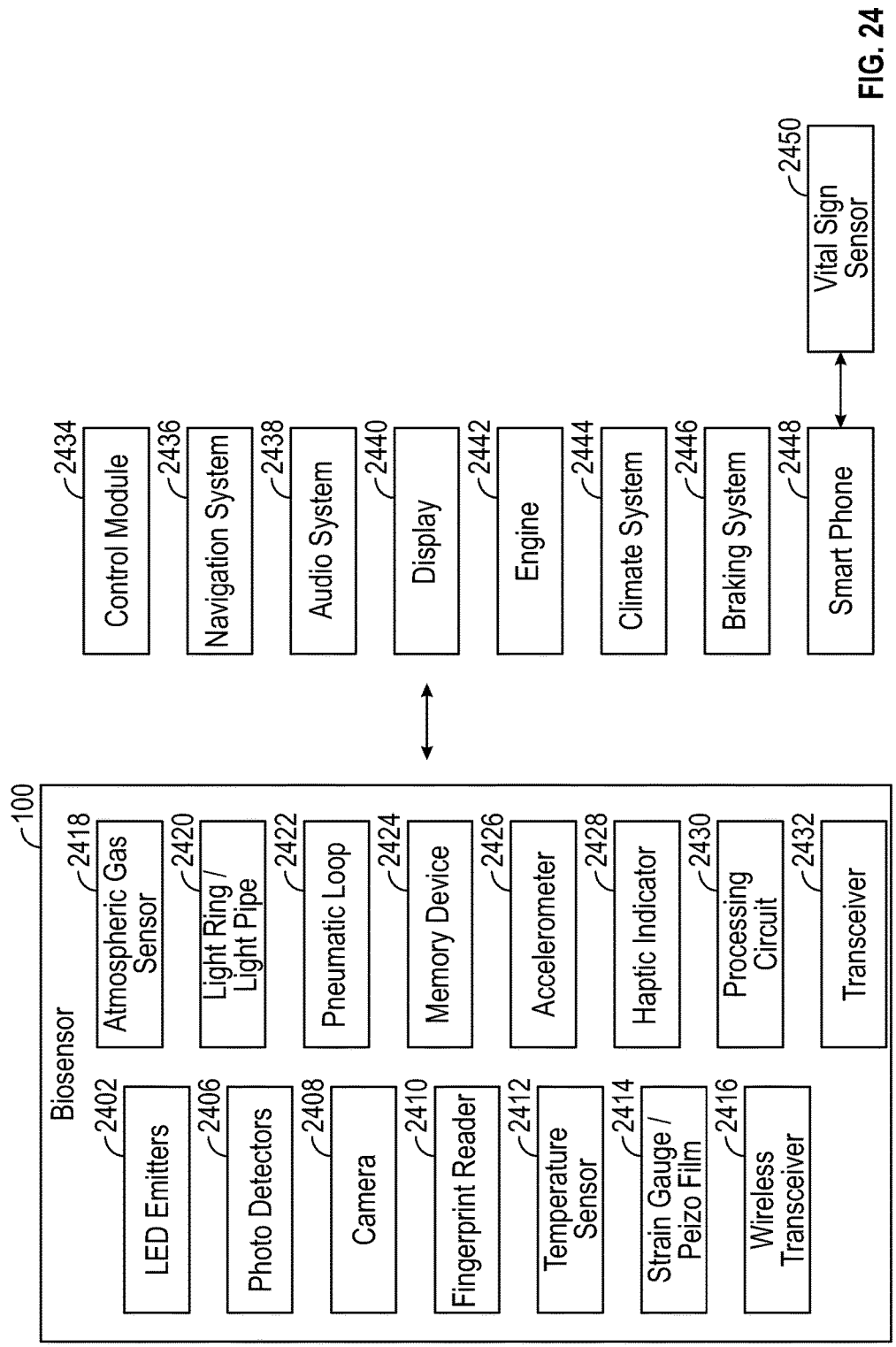
FIG. 24 illustrates a schematic block diagram of exemplary components in another embodiment of the biosensor.

FIG. 24 illustrates a schematic block diagram of exemplary components in another embodiment of the biosensor 100. The biosensor 100 includes the LED emitters 2402 and photodetectors 2406 in the PPG circuit 110. Alternatively, a camera 2408 may be implemented to detect the spectral responses. A fingerprint reader 2410 may be implemented to obtain a 2D or 3D fingerprint of a user. A temperature sensor 2412 may be included to obtain a skin temperature of a user. A strain gauge or piezo film 2414 may be included to measure a pressure applied to the touchpoint 1908. Alternatively or in addition, a pneumatic loop 2422 may be included to detect the pressure applied to the touch point 1908. A wireless transceiver 2416 or wired transceiver 2432 may also be implemented. An atmospheric gas sensor 2418 may be included as described in more detail herein.

A light ring or pipe 2420 may be included to provide a visual indicator. For example, the light ring 2420 may indicate to increase or decrease pressure applied to the touch point 1908 by a fingertip. The light ring 2420 may generate a visual feedback during a measurement period, e.g. by flashing at each detected heart beat or providing a green illumination for good signal detected. A haptic indicator 2428 may also be included to provide a tactile feedback.

The biosensor 100 may include an accelerometer to determine position of the biosensor 100 or an activity level of a user. The biosensor 100 also includes a processing circuit 2430 and memory device 2424.

The biosensor 100 may communicate with one or more components of a vehicle, including a control module 2434, navigation system 2438, engine 2442 and braking system 2446. The biosensor 100 may generate one or more feedback indicators to provide feedback to a user using the audio system 2436 or display 2440 of the vehicle. In addition, the climate system 2444 may be controlled to lower or increase a temperature of the vehicle in response to biosensor data. The climate system 2444 may also provide a feedback to a user, such as a quick puff of air to alert a drowsy driver, etc. A smart phone 2448 or other user device may include or be coupled to another biosensor 100 or other vital sign sensor 2450. The user device may communicate any detected vital signs to the biosensor 100 or to the vehicle. The biosensor 100 may communicate health information to the user device for storage or display. The biosensor 100 may thus generate a feedback, such as a visual, auditory or tactile feedback, in response to the health information.

Figure 25:
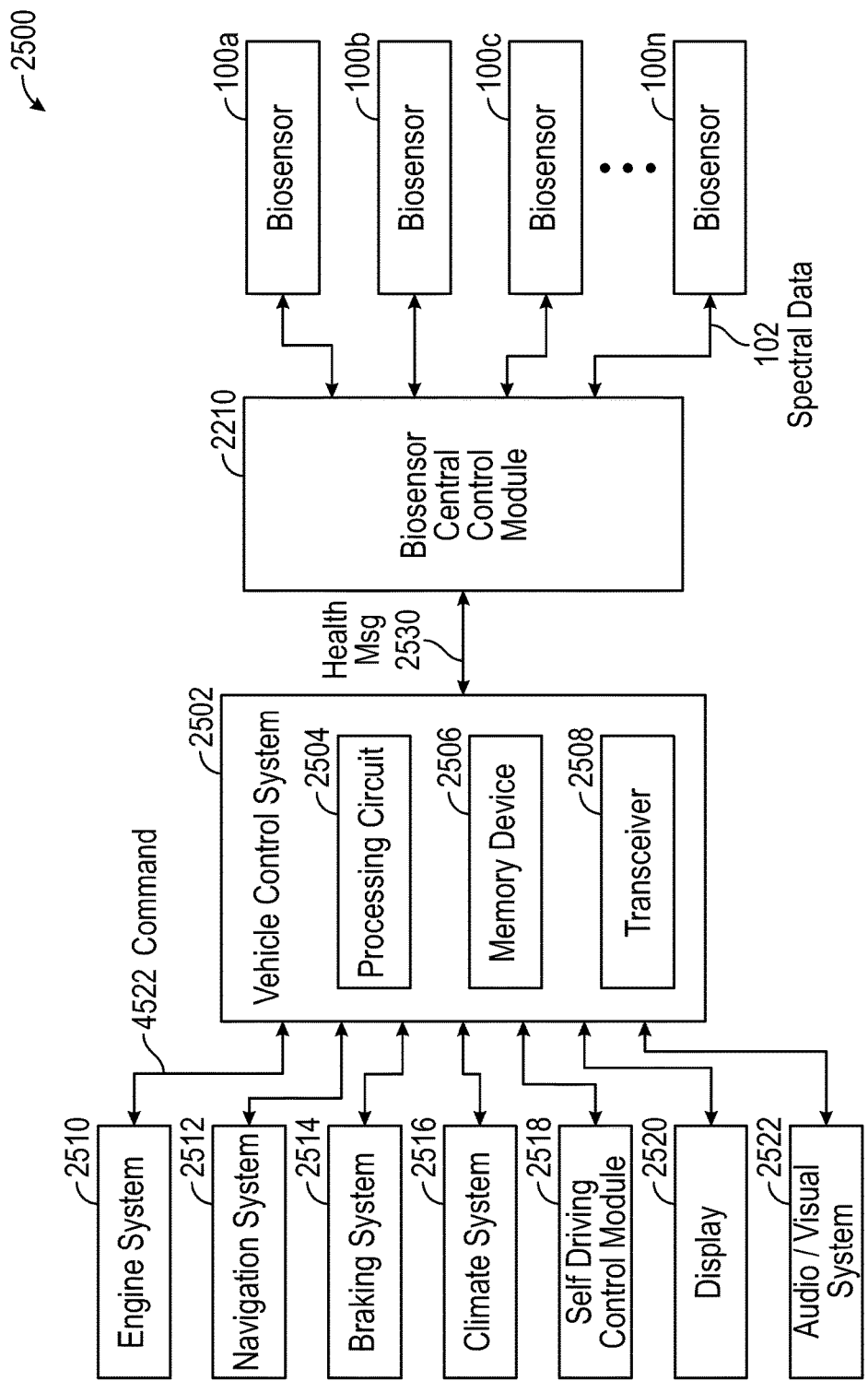
FIG. 25 illustrates a schematic block diagram of an embodiment of a vehicle with an integrated biosensor central control module.

FIG. 25 illustrates a schematic block diagram of an embodiment of a vehicle 2500 with an integrated biosensor central control module 2210. The vehicle 4500 includes a vehicle control system 2502 having a processing circuit 2504 and memory device 2506. In one aspect, the memory device 2506 may include one or more non-transitory processor readable memories that store instructions which when executed by the processing circuit 2504, causes the processing circuit 2504 to perform one or more functions described herein. The vehicle control system 2502 further includes a transceiver 2508 operable to communicate with the biosensor central control module 2210 and other internal components of the vehicle 4500. The transceiver 4508 includes a wireless or wired transceiver configured to communicate with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the transceiver 4508 may operate using RFID, short range radio frequency, infrared link, or other short range wireless communication protocol. In another aspect, the wireless transceiver may also include or alternatively include an interface for communicating over a cellular network, WiMAX or other wide area wireless network.

The plurality of biosensors 100*a-n* may be integrated into components of the vehicle 2500, such as a key fob or control buttons 1900. One or more the biosensors 100*a-n* may be integrated in a user device 2208. The biosensors 100*a-n* may include a PPG circuit 110 and temperature sensor 108 or other sensors described herein and employ the processing circuit of the biosensor central control module 2210 to perform one or more functions described herein with respect to the biosensor 100. In other embodiments, the biosensors 100*a-n* may employ one or more separate processing circuits.

The vehicle control system 2502 is configured to control or generate commands or requests to one or more systems of the vehicle 2500 including the engine 2510, navigation system 2512, braking system 2514, climate system 2516, self-driving control module 2518, display 2520 or audio/visual system 2522. Though shown as a separate system, the vehicle control system 2502 may be incorporated within one or more of the other systems of the vehicle 2500. In addition to or alternatively, the biosensor central control module 2210 may be incorporated in the vehicle control system 2502, or the biosensors 100*a-n* may transmit spectral data directly to the vehicle control system 2502.

During operation, the biosensor central control module 2210 generates health information of an occupant and generates a health message 2530 for transmission to the vehicle control system 2502. The health message 2530 includes health information of the occupant or other alerts. For example, the health message 2530 includes a request or command to the vehicle to provide feedback in response to the health information, such as audio alert, visible display of the health information or tactile response.

In response to the health message 2530, the vehicle 2500 may be configured to perform one or more feedback operations. For example, the vehicle control system 2502 may generate one or more GUIs to present the health information on the display 2520 as well as present user commands to control the biosensors 100*a-n*. For example, the display 2520 may include a touch screen or pad to select commands on the display 2520 to control operation of the biosensors 100*a-n*.

The vehicle control system 2502 may also issue warnings, on the display and/or via audio alerts or tactile alerts, in response to the health message 2530. For example, when a driver's heart rate or a glucose level exceeds a normal range, the vehicle control system 2502 may control the display to generate a warning and the audio/visual system 2522 to emit an audible alarm. In another example, when a heart rate of a driver falls below a normal range, the vehicle control system 2502 may determine that the driver is drowsy. The vehicle control system 2502 may flash the headlights, blow cold puffs of air, or otherwise provide an audible, visual or tactile alert to the drive. The heart rate information may be combined with other information, such as from a camera or driver reaction time to determine drowsiness or other impairment of the driver.

The vehicle 2500 may transmit the health information using the transceiver 2508 over a wide area network, such as a cellular network, to a third party service provider, such as a health care provider or emergency service provider. The vehicle may also transmit the health information, e.g. via a Bluetooth or WLAN interface, to a user device 2208.

Figure 26:
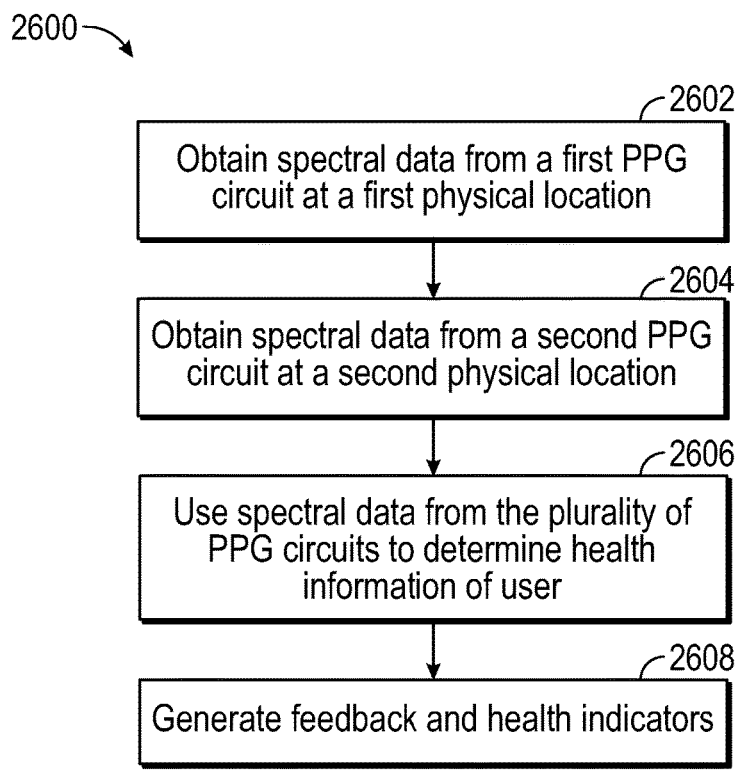
FIG. 26 illustrates a logical flow diagram of an embodiment of a method for a health monitoring system.

FIG. 26 illustrates a logical flow diagram of an embodiment of a method 2600 for a health monitoring system. A plurality of biosensors 100 (including PPG circuits 110) obtain spectral data 120, e.g. filtered or processed digital spectral responses including PPG waveforms over one or more cardiac cycles of a user. The plurality of biosensors 100 are physically located in different locations, e.g. in different control buttons 1900 of the vehicle 2500, in a key fob, in a steering wheel or in a user device. The plurality of biosensors communicate the spectral data 120 including the PPG waveforms to the biosensor central control module 2210. The biosensor central control module 2210 thus obtains spectral data from a first PPG circuit at a first physical location at 2602 and from a second PPG circuit at a second physical location at 2604.

The biosensor central control module 2210 may combine the spectral data 120 to obtain a set of PPG waveforms for processing. For example, PPG waveforms from spectral data from a first biosensor are combined with PPG waveforms from spectral data from a second biosensor to obtain a set of PPG waveforms for processing. The combined set of PPG waveforms may thus be of sufficient quality and number to obtain a heart rate, respiration rate, oxygen saturation level or other vital sign.

The biosensor central control module 2210 processes the spectral data 120 from the plurality of PPG circuits 110 to obtain health information of a user, such as vitals of the user, including heart rate, respiration rate and oxygen saturation levels at 2606. The biosensor central control module 2210 may also obtain other health data such as concentration levels of one or more substances in blood flow of the user or alertness of the user.

The biosensor central control module 2210 may only combine spectral data obtained from a user within a predetermined measurement period. For example, the spectral data may only be combined when obtained within a one minute, five minute or ten minute measurement period. By combining the spectral data from the plurality of biosensors, the biosensor central control module 2210 obtains spectral data of a user over additional cardiac cycles or respiration cycles.

The biosensor central control module 2210 may generate feedback and health indicators in response to the health information at 2608. For example, the biosensor central control module 2210 may generate a health message 2530 including the health information to the vehicle control system 2502 for display or to alert a user to a potential health risk. The health message 2530 may include a request for feedback in response to the health information, including an auditory, tactile or visible alert. The health vehicle 2500 may then generate one or more of: visible feedback, audible feedback or tactile feedback in response to the health message 2530.

Figure 27:
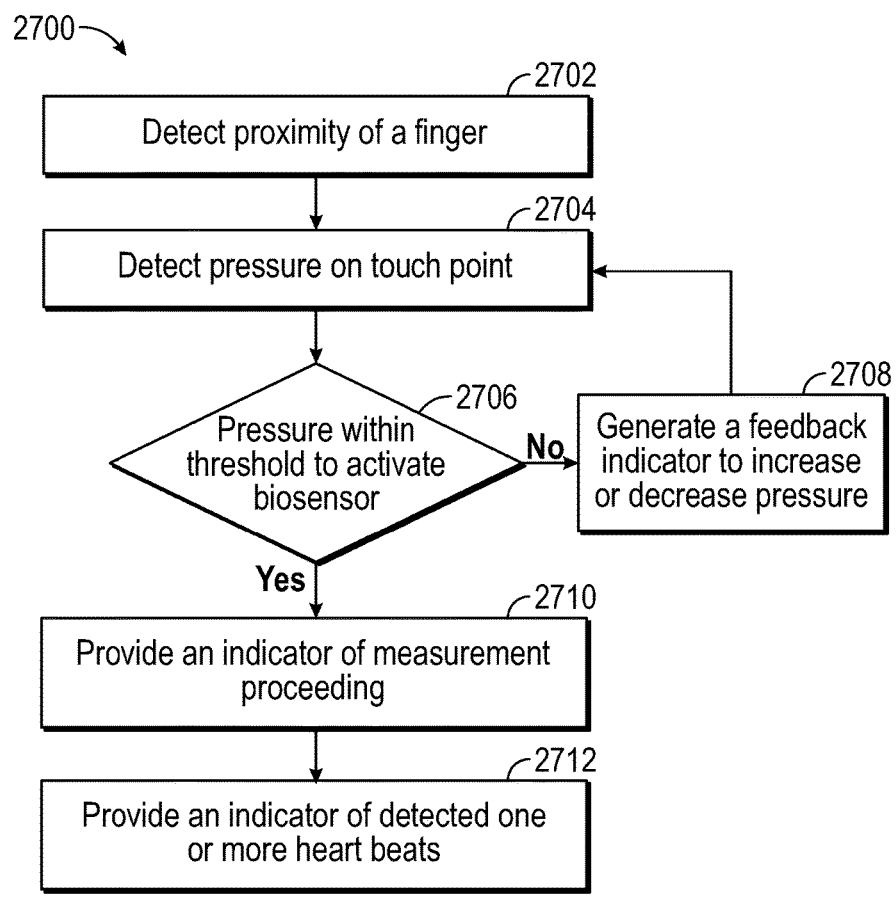
FIG. 27 illustrates a logical flow diagram of an embodiment of a method for operation of a control button including a biosensor.

FIG. 27 illustrates a logical flow diagram of an embodiment of a method 2700 for operation of a control button 1900 including a biosensor 100. In an embodiment, the control button 1900 includes a touch pad or touch point 1908 with a proximity indicator 114 and pressure sensor 112. The proximity indicator 114 includes one or more LEDs, e.g. in the IR range, that emit pulses of light. When a finger or other body part is positioned near the touch point, a photodiode or other photodetector may then detect a reflectance of the IR light. The control button 1900 may thus detect proximity of a finger at 2702 and activate the PPG circuit 110.

The touch point 1908 may also be pressure sensitive. For example, a pressure sensor 112 may detect a pressure on the touch point 1908 by a finger or other body part at 2704. The biosensor 100 determines whether the detected pressure is within a threshold to active the PPG circuit 110 at 2706. When the pressure is not within the threshold, the biosensor 100 may generate a feedback indicator at 2708. The feedback indicator provides a visible, audible or tactile indication that the pressure applied by the finger on the touch point 1908 needs to increase or decrease for activation of the biosensor 100.

The control button 1900 may further provide an indicator that the biosensor has been activated, and measurement is proceeding at 2710. The control button 1900 may further provide a haptic indicator or an audible or visual indicator of detected cardiac cycles, e.g. heart beats at 2712. For example, the control button may generate a flashing LED for each cardiac cycle.

Figure 28:
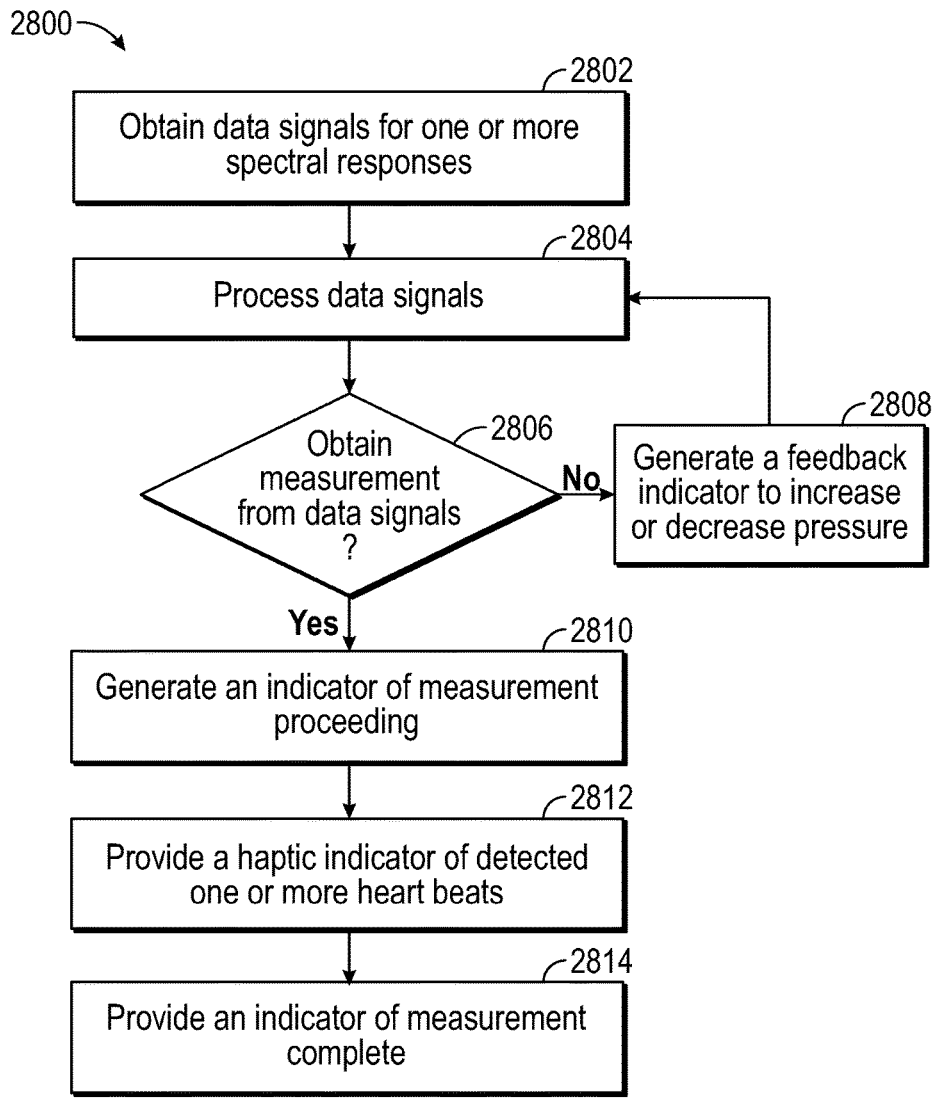
FIG. 28 illustrates a logical flow diagram of an embodiment of a method for operation of a control button including a biosensor.

FIG. 28 illustrates a logical flow diagram of an embodiment of a method 2800 for operation of a control button 1900 including a biosensor 100. The biosensor 100 obtains data signals generated from one or more spectral responses at 2802 and processes the data signals at 2804. The biosensor 100 may then determine a quality of the data signals, such as background noise, interference, signal to noise ratio. The biosensor 100 may also determine whether the quality of the data signals is within predetermined tolerance limits, e.g. sufficient to obtain measurements of the spectral responses over one or more the cardiac cycles. When not sufficient at 2806, the biosensor 100 may generate a feedback indicator to a user to increase or decrease pressure applied to the touch point 1908.

When the data signals are within predetermined tolerance limits, the biosensor 100 may generate an indicator that measurements are proceeding at 2810. The indicator may be a visual green ring of light on the control button 1900 or other visible or audible indicator. The biosensor 100 may also provide a haptic indicator of detected one or more heart beats or cardiac cycles or other visible or audible indicator at 2812. The biosensor 100 may also provide an indicator that a measurement is complete at 2814. For example, the biosensor 100 may determine that spectral responses over at least a 5-10 cardiac cycle time period are needed to obtain a desired vital or concentration level. The biosensor 100 may thus indicate when it has detected data signals within predetermined tolerance limits, e.g. sufficient to obtain measurements of the spectral responses, over the needed 5-10 cardiac cycles.

Figure 29:
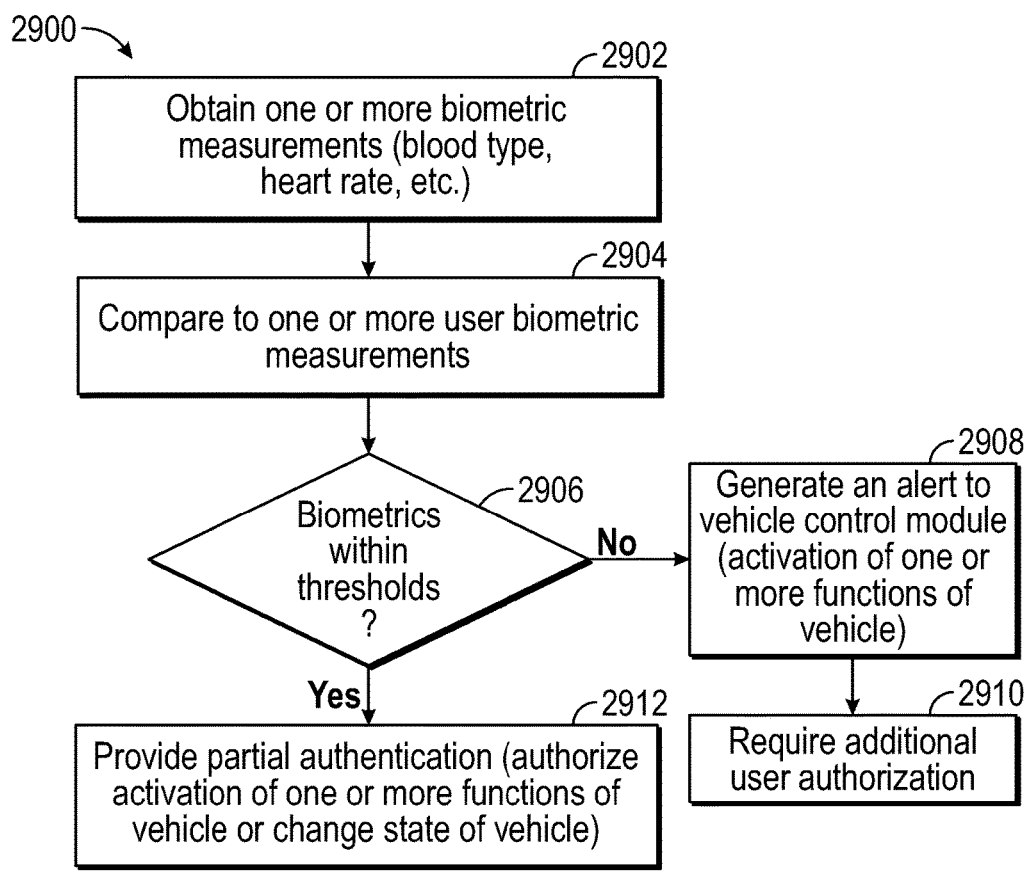
FIG. 29 illustrates a logical flow diagram of an embodiment of a method for partial authorization of a user using one or more biometric measurements.

FIG. 29 illustrates a logical flow diagram of an embodiment of a method 2900 for partial authorization of a user using one or more biometric measurements. The one or more biometric measurements may include blood type, heart rate, PPG wave form, etc. For example, the one or more biometric measurements may be obtained using PPG techniques as described herein at 2902. The obtained biometric measurements are then compared to stored biometric measurements of an authorized user at 2904. It is then determined whether the obtained biometric measurements are within predetermined thresholds at 2906.

When not, an alert may be generated to the vehicle control system 2502 at 2908. The vehicle control system 2502 may prevent activation of one or more functions of the vehicle or prevent a change of a state of the vehicle. For example, the vehicle control module may prevent shifting out of park or start of the ignition or opening of a door for entry. The vehicle control system 2502 may require additional user authorization at 2910 prior to activation of the one or more functions of the vehicle. For example, a unique code may need to entered or fingerprint verification or other type of authorization.

When the obtained biometric measurements are within predetermined thresholds, full or partial authorization may be provided to activate one or more functions of the vehicle or change a state of the vehicle at 2912. For example, an authentication message may be generated to the vehicle. The vehicle may then provide a full or partial authentication to the user in response to the authentication message. A full authentication would authorize the user to perform all functions of the vehicle. A partial authentication would authorize the user to perform a limited set of functions of the vehicle.

For example, a partial authentication may allow a door to be unlocked or start of an ignition but not to shift the vehicle into drive.

Though the example described herein is with respect to a vehicle, the biosensor 100 may be used for authentication in other applications. For example, the biosensor 100 may be used to generate biometric measurements for authentication for entry to a building, authentication to a computing device, identification to a governmental authority or other applications.

Figure 30:
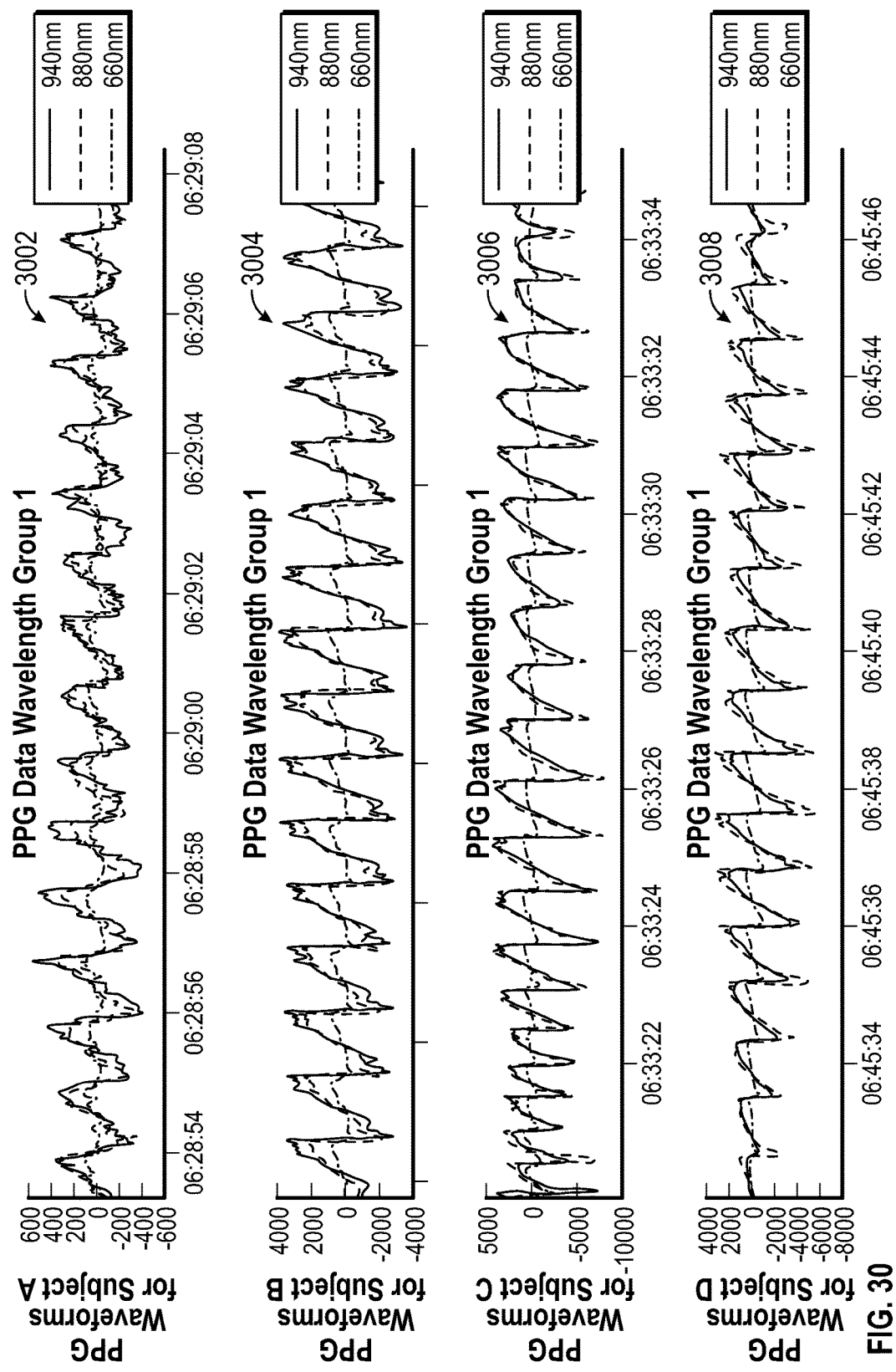
FIG. 30 illustrates a graphical representation obtained from a biosensor of the PPG waveform of various subjects.

FIG. 30 illustrates a graphical representation obtained from a biosensor 100 of the PPG waveform of various subjects. In one embodiment, the shape of the PPG waveforms are measured and used as a unique biometric measurement to identify a user. A first graph 3002 illustrates PPG waveforms of a first subject A, and a second graph 3004 illustrates PPG waveforms of a second subject B. The third graph 3006 illustrates PPG waveforms of a third subject C, and a fourth graph 3008 illustrates PPG waveforms of a third subject D. As seen in the graphs, the PPG waveforms of the subjects are unique, e.g. the PPG waveforms of a subject are different from the PPG waveforms of other subjects. In the article, "On the Analysis of Fingertip Photoplethysmogram Signals," by Mohamed Elgendi, Current Cardiology Reviews, Volume 8, pages 14-25 (2012), which is hereby incorporated by reference herein, the different characteristic features of the PPG waveform are discussed. For example, a typical PPG waveform includes a systolic peak, a diastolic peak, dicrotic notch, and pulse width. Other characteristics include pulse area, pulse interval, peak to peak interval, augmentation index, crest time, etc. These or other characteristics may be determined from a first or second derivative of the PPG waveform. For example, various ratios may be derived from a second derivate of the PPG waveform, e.g., such as the early systolic negative wave to the early systolic positive wave (Ratio b/a). These and other characteristics may be measured in a PPG waveform (including its derivatives) and compared with one or more stored characteristics of PPG waveforms for biometric identification of a user. Since PPG waveforms for a subject may vary over time, the stored PPG waveform and its characteristics for a user need to be updated periodically.

In use, a biosensor 100 obtains a spectral response including PPG waveforms for a user over one or more cardiac cycles. Various patterns or points of the PPG waveform (including its derivatives) are determined and compared with stored patterns or parameters of one or more PPG waveforms. Based on the comparison, an authentication of the user may be determined.

Figure 31:
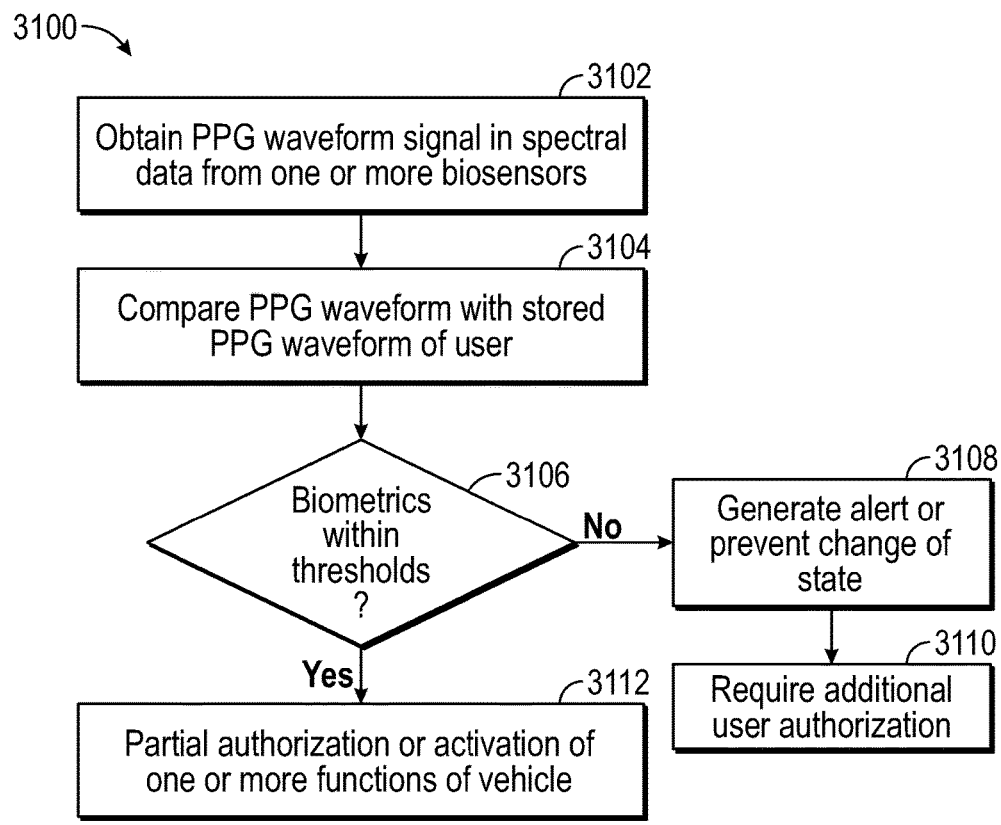
FIG. 31 illustrates a logical flow diagram of a method for authentication using a PPG waveform as a biometric measurement.

FIG. 31 illustrates a logical flow diagram of a method 3100 for authentication using a PPG waveform as a biometric measurement. The PPG waveform signal is obtained over one or more cardiac cycles at 3102. For example, the PPG waveform may be obtained from spectral data received from one or more biosensors 100. Various characteristics of the PPG waveform are determined and compared with stored characteristics of one or more authorized users. Alternatively, a pattern recognition process may be performed to compare the PPG waveform with a stored PPG waveform of a user at 3104. It is then determined whether the PPG waveform is authenticated, e.g., whether the characteristics of the measured PPG waveform is within predetermined thresholds of stored characteristics of PPG waveforms of authorized users at 3106.

If not, an alert may be generated to the vehicle control system 2502 at 3108. The vehicle control system 2502 may prevent activation of one or more functions of the vehicle or prevent a change of a state of the vehicle. For example, the vehicle control system 2502 may prevent shifting out of park or start of the ignition or opening of a door for entry. The vehicle control system 2502 may require additional user authorization at 3110 prior to activation of the one or more functions of the vehicle. For example, a unique code may need to be entered or fingerprint verification performed or other type of authorization completed.

When the obtained biometric measurements are within predetermined thresholds, full or partial authorization may be provided to activate one or more functions of the vehicle or change a state of the vehicle at 3112. For example, an authentication message may be generated to the vehicle. The vehicle may then authorize unlocking of the vehicle or ignition in response to the authentication message.

The biosensor 100 described herein may be configured to assess the blood group of a patient using the PPG circuit 110. In an embodiment, the PPG circuit 110 emits a series of pulses at a patient's tissue to obtain a series of R values. The series or average of the series of R values is used to identify a blood grouping or antigen group. The PPG circuit 110 uses a series of pulses firing LED's at a rate of between 100-200 Hz to obtain a good heart rate signal. One or more of the following R values for 550/940 nm, 660/940 nm, and 880 nm/940 nm frequencies may be obtained over an integration of a series of heartbeats. Due to the division of the L values, the R value eliminates the input from the skin tissue and non-pulsating blood flow to isolate the input from the pulsating blood flow (venous or arterial). To determine a blood group, the R values may be obtained over a sample window, such as over a plurality of heartbeats. A blood group indicator may be derived from the values of the R ratio over the sample window. For example, an integration of the R values over the sample window may be determined and then the integrated R values used as the blood group indicator. The blood group indicator is then used to identify a blood group from one or more blood group reference tables.

For example, in order to enhance the data signal of a spectral response, the data signal in a spectral response over a series of heart beats is used for the sample window. The R value may be obtained over the sample window using spectral responses around a plurality of frequencies. The frequencies may include, e.g., 550, 660 and 880 nm frequencies or in ranges of wavelengths around such frequencies. In one embodiment, the frequencies include 530 and 590 nm and values for the ratio $R=L_{530}/L_{940}$ and $R=L_{590}/L_{940}$ are determined over the sample window. The values for the first $R_{530/940}$ ratio are then integrated across the sample window to determine an integrated R value as a first blood group indicator. The values for the second $R_{590/940}$ ratio are then integrated across the sample window to determine an integrated R value as a second blood group indicator. A simple integration algorithm for each individual frequency may be implemented to obtain the blood group indicators. In another embodiment, the values for the R ratios are averaged over the sample window. Other functions using the values of the R ratios over the sample window may be implemented to obtain one or more blood group indicators.

The obtained one or more blood group indicators are then used with a calibration table to identify a blood group of the patient, human or animal. For example, the calibration table includes a correlation of values or ranges of the one or more blood group indicators to blood group or blood type. The calibration table may be determined by obtaining the blood group indicator for a sample general population for each known blood type.

Figure 32:
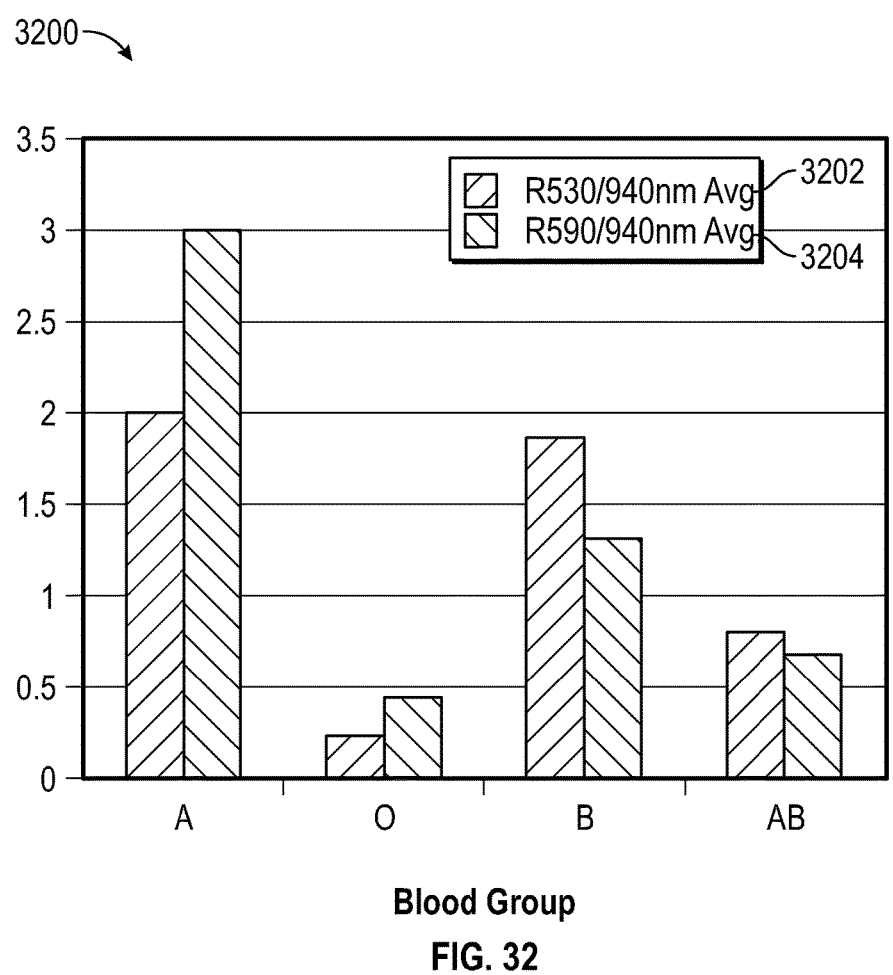
FIG. 32 illustrates a schematic drawing of an embodiment of a calibration table for blood groups.

FIG. 32 illustrates a schematic drawing of an embodiment of a calibration table 3200 for blood groups. The calibration table 3200 or blood group reference table includes an expected or know range of average values for R ratios for a plurality of the blood groups. The blood group reference table 3200 illustrates expected values for a plurality of blood group indicators for each blood group A, O, B, and AB. In this embodiment, the blood type indicators for the patient include an average $R_{530/940}$ value 3202 and an average $R_{530/940}$ value 3204. The expected average values for the blood group indicators of $R_{530/940}$ ratio 3202 and $R_{590/940}$ ratio 3204 are shown for each of the blood groups A, O, B and AB.

The measured average $R_{530/940}$ value and $R_{590/940}$ value may be compared to the blood group reference table 3200. Though the RH+ and RH− types are not shown in this blood group reference table 3200, a calibration graph or table may be used to determine the RH+ and RH− types of each Blood Groups A, B, AB and O. For example, the blood group A, B, AB and O may first be determined and then the RH+ and RH− types determined using the same or different blood type indicators. In another embodiment, the blood group A, B, AB and O and RH+ and RH− type may be determined using a same calibration table and blood type indicators. For example, values of the R ratio at 535 nm/940 nm may be used to detect either Rh+ or Rh−.

In another embodiment, though two blood type indicators are illustrated herein, three or more blood type indicators may be used to determine the blood type or a single blood type indicator may be used to determine the blood type. For example, a first blood type indicator may be determined and compared with the blood group reference table 3200. If the first blood type indicator fails to correlate with an expected value for a blood type, one or more additional blood type indicators may be obtained and compared with the blood group reference table 3200. In addition, though the blood group reference table 3700 illustrates a single expected value for each blood type indicator, the blood group reference table 3200 may indicate a range of expected values for one or more blood type indicators. The various R values indicate a presence of an antigen to identify a blood group of A, B, O or AB using the plurality of spectral responses. The biosensor 100 may use the same R values or different R values to determine a presence of another antigen within a blood group to identify an RH factor using the plurality of spectral responses.

Figure 33:
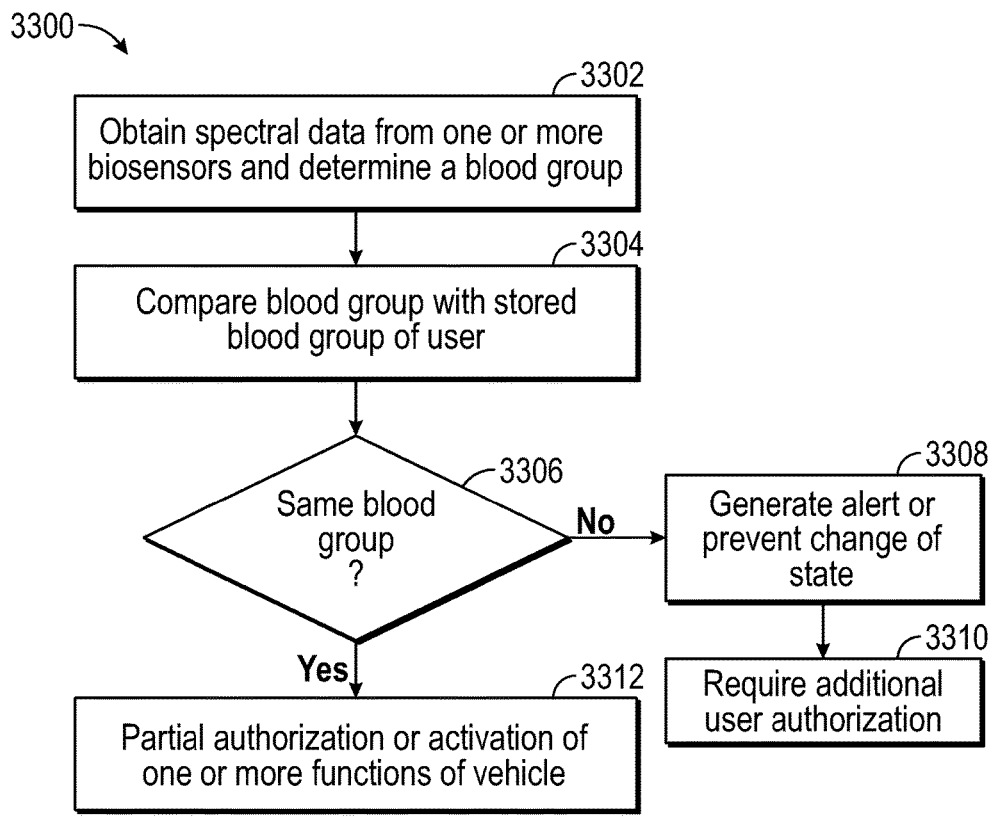
FIG. 33 illustrates a logical flow diagram of a method for authentication using a blood group of a user as a biometric measurement.

FIG. 33 illustrates a logical flow diagram of a method 3300 for authentication using a blood group of a user as a biometric measurement. Spectral data is obtained over one or more cardiac cycles from one or more biosensors 100 at 3302. The blood group is determined using the spectral data. The determined blood group is then compared to a stored blood group of a user at 3304. It is then determined whether the blood group is the same at 3306.

If not, an alert may be generated to the vehicle control system 2502 at 3308. The vehicle control system 2502 may prevent activation of one or more functions of the vehicle or prevent a change of a state of the vehicle. For example, the vehicle control system 2502 may prevent shifting out of park or start of the ignition or opening of a door for entry. The vehicle control system 2502 may require additional user authorization at 3310 prior to activation of the one or more functions of the vehicle. For example, a unique code may need to entered or fingerprint verification or other type of authorization.

When the obtained biometric measurements are within predetermined thresholds, full or partial authorization may be provided to activate one or more functions of the vehicle or change a state of the vehicle at 3312. Since blood group is not unique to an individual, the blood group may be used as one of a plurality of authorization tools or biometric measurements.

The biosensors 100 may also be configured to obtain a concentration level of an indicator in blood flow of alcohol levels using the plurality of spectral responses. For example, the indicator may include a P450 enzyme or an ADH related enzyme or ethanol. The biosensor 100 may determine the blood alcohol level using the indicator and a calibration table.

Figure 34:
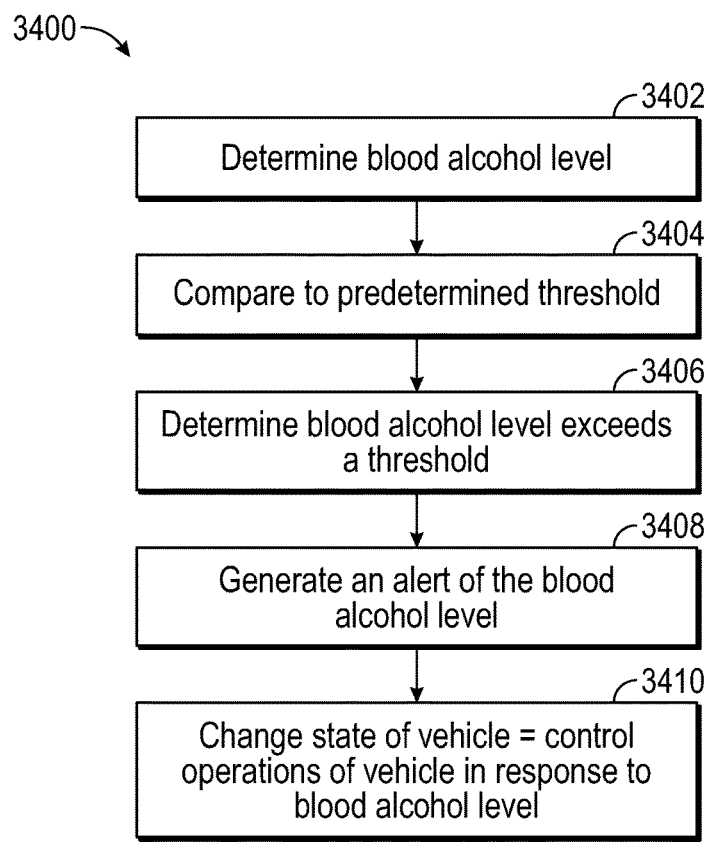
FIG. 34 illustrates a logic flow diagram of an embodiment of a method for controlling operation of the vehicle in response to a blood alcohol level.

FIG. 34 illustrates a logic flow diagram of an embodiment of a method 3400 for controlling operation of the vehicle in response to a blood alcohol level. One or more of the biosensors 100 provides spectral data to obtain a blood alcohol level at 3402. For example, a user may place a finger on one of the touch points 1908 of a control button 1900. The PPG circuit 110 then obtains a plurality of spectral responses, and the biosensor 100 or biosensor central control module 2210 uses the plurality of spectral responses to determine one or more indicators of blood alcohol levels, e.g. any combination of P450 or ethanol or NADH or other enzyme alcohol dehydrogenase (ADH) derivative. A health message may be transmitted to the vehicle control system 2502 indicating the blood alcohol level of the user.

The vehicle control system 2502 then compares the blood alcohol level to a predetermined threshold at 3404. The vehicle control system 2502 may then determine the blood alcohol level exceeds the predetermined threshold at 3406. The vehicle control system 2502 may then generate an alert or notification of the blood alcohol level at 3408. For example, the notification may indicate that the blood alcohol level exceeds the predetermined threshold.

The notification may be displayed on a vehicle display or transmitted to a user device over a short range wireless network or to a third party service provider over a wide area wireless network. The vehicle control system 2502 may also generate a command to prevent one or more operations of the vehicle 2500 in response to the blood alcohol level at 3410. For example, a command may be generated to an ignition system or engine to prevent the vehicle 2500 from starting or shifting out of park. Though the vehicle control system 2502 is described as performing various operations herein, one or more of the operations described herein may alternatively be performed by one or more of the biosensors 100a-n or the biosensor central control module 2210.

Figure 35:
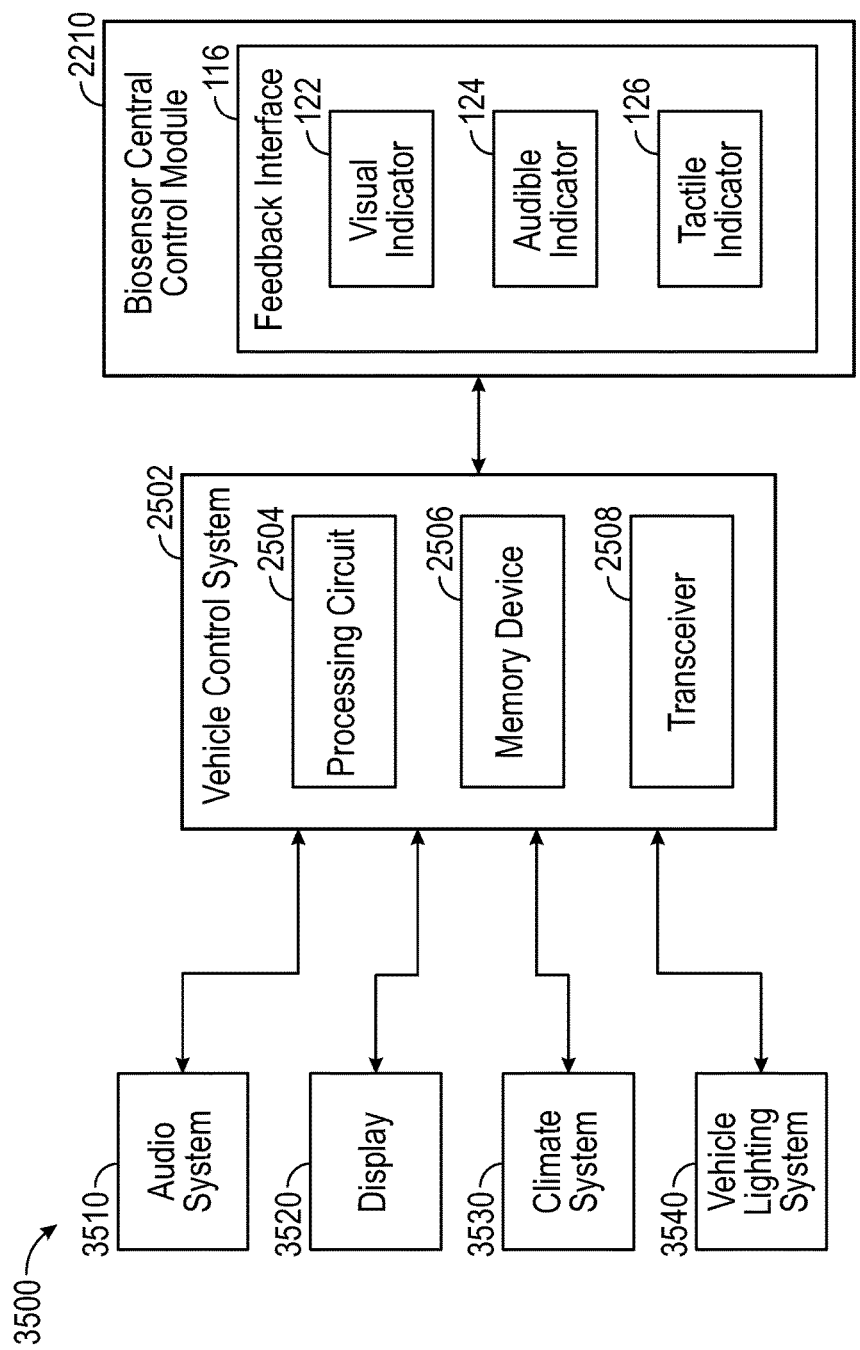
FIG. 35 illustrates a schematic block diagram of a vehicular health monitoring system with feedback interfaces.

FIG. 35 illustrates a schematic block diagram of a vehicular health monitoring system 3500 with feedback interfaces. The biosensor central control module 2210 includes a feedback interface 115 for a plurality of types of indicators, visual 122, audible 124, tactile 126, and haptic 128. The various indicators may be generated in response to health information by the biosensor central control module 2210 and transmitted to the vehicle control system 2502. In another embodiment, the various indicators may be generated in response to health information by the vehicle control system 2502. For example, the audio system 3510 may be controlled to generate audible indicators 124, e.g. of health information or health alerts. The display 3520 may be controlled to display visual indicators 122, e.g. display of health information or health alerts. The climate system 3530 may be controlled to generate tactile indicators 126, e.g. cold air in case of drowsiness of a driver or fresh air in case of high gas content in the atmosphere, etc. The vehicle lighting system 3520 may be controlled to generate visual indicators 122, e.g. of health alerts. For example, interior lights or headlights may be flashed in response to driver drowsiness or other health alert. A plurality of the systems may be employed to provide audible, visual and tactile/haptic indicators of health information or health alerts.

The control button 1900 may further initiate a tactile, audible or visual indicator. For example, the light ring 1902 may flash to indicate pressure on the touch point 1908 may need to increase or decrease. The multiple LED emitters 1904 may flash to indicate detected cardiac cycles when measurement is in progress.

Figure 36:
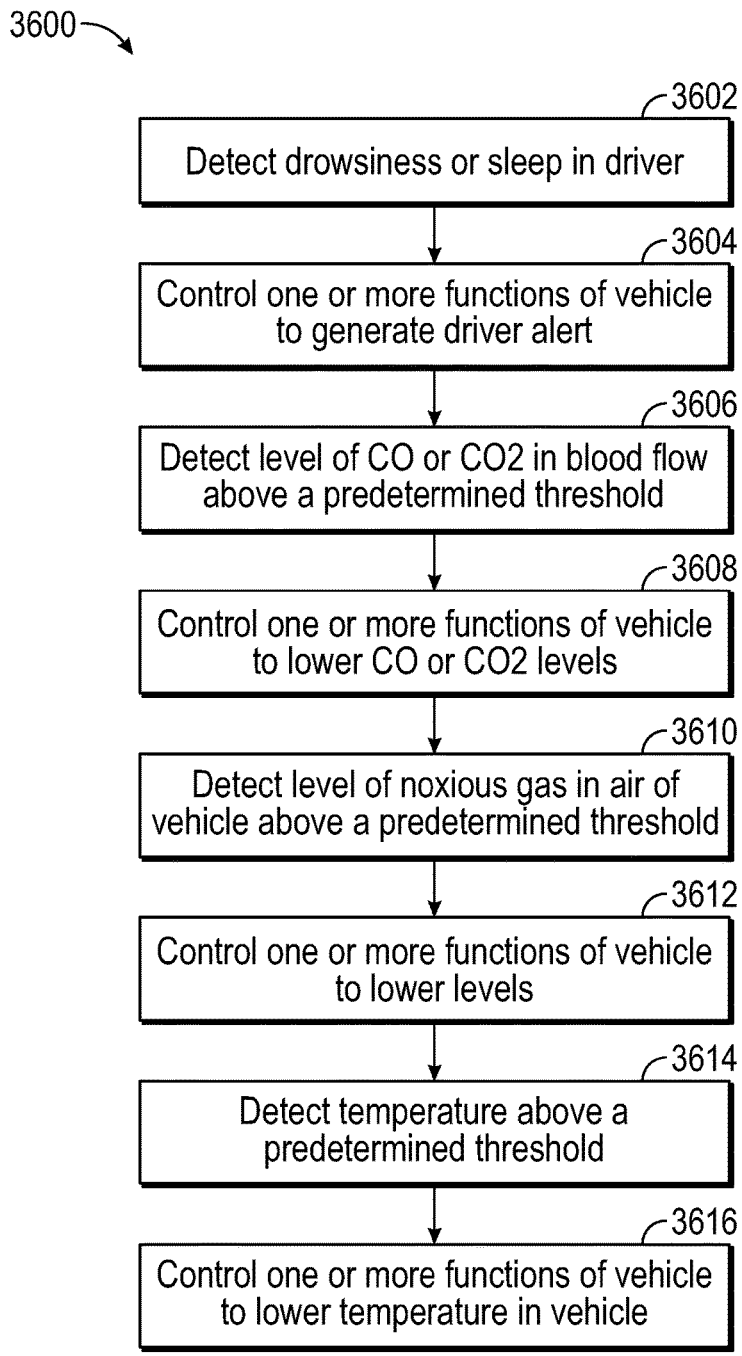
FIG. 36 illustrates a logical flow diagram of a method for controlling one or more functions of a vehicle in response to health information.

FIG. 36 illustrates a logical flow diagram of a method 3600 for controlling one or more functions of a vehicle 2500 in response to health information. The biosensor central control module 2210 may detect drowsiness of a driver at 3602. For example, a heart rate that drops below a predetermined threshold (such as 20% below a normal rate) may indicate a drowsy or sleeping driver. Other factors such as facial images or slow driver reaction time may also be considered. In response to an alert of a drowsy or sleeping driver, the vehicle control system 2502 may control one or more functions of the vehicle to generate a driver alert at 3604, such as flashing interior lights, providing an audible or visual alarm, setting a high fan speed for air, etc.

In another embodiment, the biosensor central control module 2210 may detect a level of carbon monoxide and/or carbon dioxide in the blood flow of an occupant or driver above a predetermined threshold at 3606. In response to an alert of the health information, the vehicle control system 2502 may control one or more functions of the vehicle to lower CO or CO2 levels in the interior of the vehicle at 3608. For example, the windows may be lowered, the climate system set to fresh air on a high fan speed, etc. The vehicle control system 2502 may also control one or more functions of the vehicle to generate a driver alert.

In another embodiment, the biosensor central control module 2210 may detect a level of noxious gas above a predetermined threshold in the interior air of a vehicle at 3610. In response to an alert, the vehicle control system 2502 may control one or more functions of the vehicle to lower gas levels in the interior of the vehicle at 3612. For example, the windows may be lowered, the climate system set to fresh air on a high fan speed, etc. The vehicle control system 2502 may also control one or more functions of the vehicle to generate a driver alert.

In another embodiment, the biosensor central control module 2210 may detect a temperature level of an interior of the vehicle or an occupant above a predetermined threshold at 3614. In response to an alert, the vehicle control system 2502 may control one or more functions of the vehicle to lower temperature levels in the interior of the vehicle at 3616. For example, the windows may be lowered, the climate system set to colder temperature air on a high fan speed, etc. The vehicle control system 2502 may also control one or more functions of the vehicle to generate a driver alert.

In another embodiment, the biosensor central control module 2210 may detect a serious health condition or unconscious or unresponsive driver. In response to an alert, the vehicle control system 2502 may control one or more functions of the vehicle to initiate a self-driving mode and stop the vehicle at the nearest hospital or safe location. The vehicle control system 2502 may also control one or more functions of the vehicle to generate a driver alert or transmit health information to a third party, such as a 911 service. The health information may include patient vitals, such as respiration rate, heart rate, SpO2 levels. The health information may also include NO concentration levels in blood flow or concentration levels of one or more other substances in blood flow. The health information may also include a blood group of the user.

Figure 37:
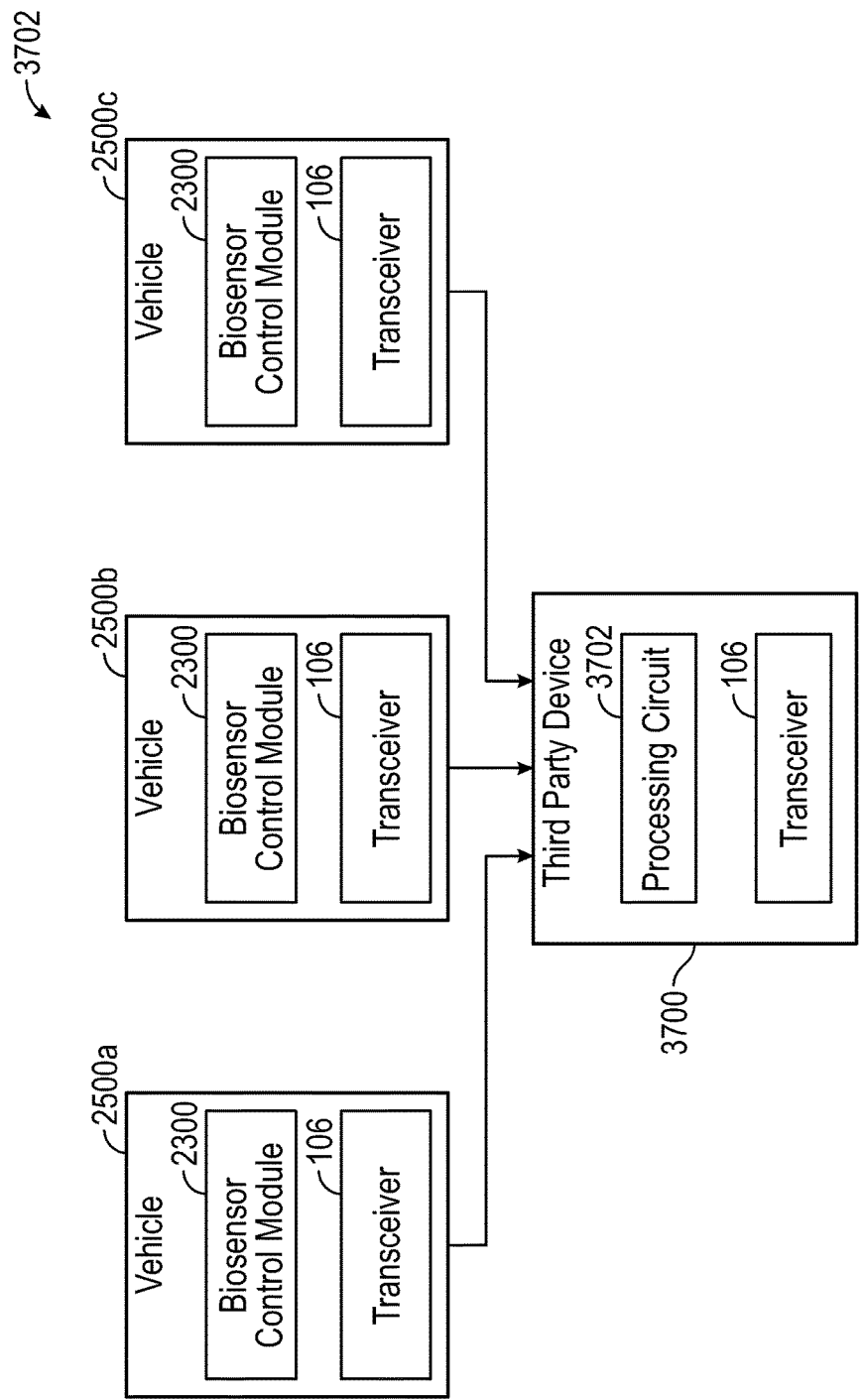
FIG. 37 illustrates a schematic block diagram of an embodiment of a network for health monitoring.

FIG. 37 illustrates a schematic block diagram of an embodiment of a network 3702 for health monitoring. The vehicles 2500*a-c* may communicate health information over a wireless wide area network, such as a cellular network, WiMAX or other WAN, to a third party device 3700. The third party device 3700 may be implemented in a 911 service, OnStar® type service or health care provider network. In another embodiment, the third party device 3700 may be implemented in a fleet manager network. For example, a fleet manager network, such as a delivery service or trucking service, may monitor health information of drivers in the vehicles 2500*a-c*.

Figure 38:
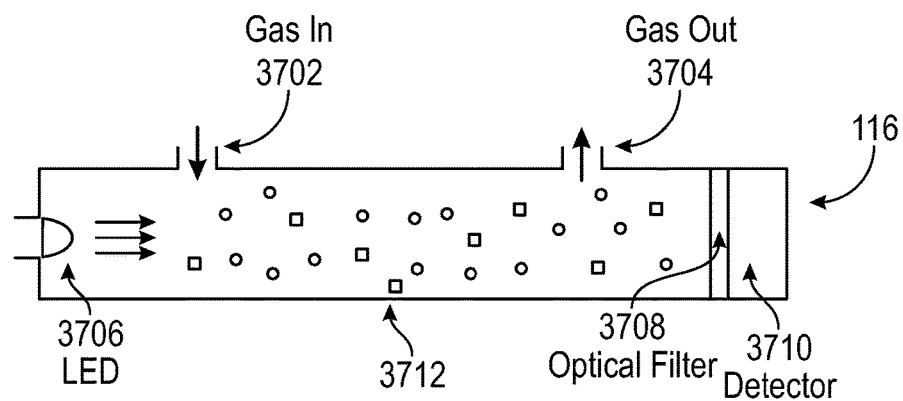
FIG. 38 illustrates a schematic block diagram of an embodiment of one type of atmospheric gas sensor.

FIG. 38 illustrates a schematic block diagram of an embodiment of one type of atmospheric gas sensor 116. The atmospheric gas sensor 116 may be implemented in a control button 1900 with a biosensor 100. The gas sensor 116 includes an intake valve 3802 and outtake valve 3804. Air surrounding the control button 1900 may thus flow through a gas enclosure 3812. An LED 3806 emits light having a wavelength in an IR range or other spectrum through the gas enclosure 3812. The light interacts with the gas in the gas enclosure 3812 and passes through an optical filter 3808 to a detector 3810. As the light passes through the gas enclosure 3812, particular gas molecules absorb certain wavelengths of the IR light while letting other wavelengths of light pass through. The optical filter may filter ambient light or other light except the wavelength absorbed by $CO_2$ or other gas being detected. The detector 3810 may then measure the received intensity of light to determine a concentration level of $CO_2$ or other gas being detected.

In an embodiment, LEDs and photodetectors of the biosensor 100 may be used for the atmospheric gas sensor 116 as well. In another embodiment, to reduce ambient light in the gas enclosure, a finger positioned on the touch point 1908 may block the outtake 3804 and/or gas intake valve 3802.

Figure 39:
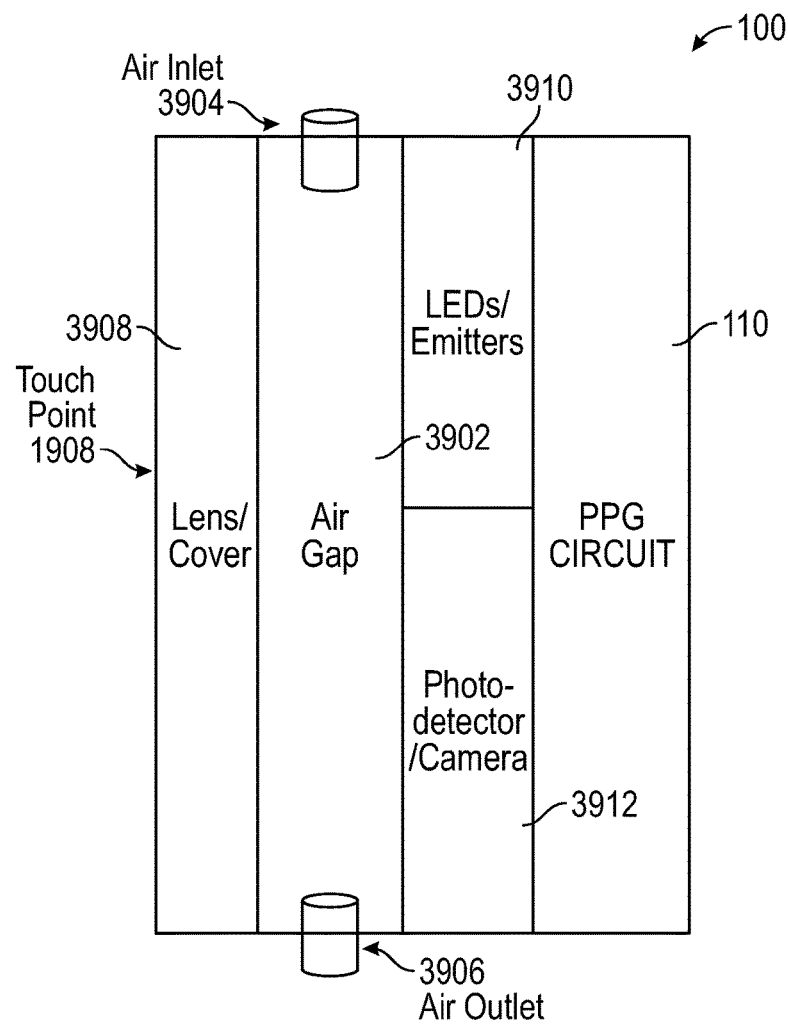
FIG. 39 illustrates a schematic block diagram of an embodiment of a PPG circuit for measuring atmospheric gas.

FIG. 39 illustrates a schematic block diagram of an embodiment of a PPG circuit 110 for measuring atmospheric gas. In an embodiment, the PPG circuit 110 may be configured to detect atmospheric gas. An air gap 3902 is formed between a lens/cover 3908 and the LEDs/emitters 3910 and photodetector/camera 3912 of a PPG circuit 110. An air inlet 3904 and air outlet 3906 provide for air flow through the air gap 3902. The lens/cover 3908 forms a pressure sensitive touch point 1908 for placement of a fingertip or other body part. The PPG circuit 110 may then obtain spectral data from the fingertip.

In addition, when the fingertip is positioned over the touchpoint 1908, the fingertip blocks ambient light in the air gap 3902. The fingertip positioned on the touch point 1908 may also block ambient light from entering the air inlet 3904 or air outlet 3906. The PPG circuit 110 may then detect a gas in the air gap 3902.

For example, the PPG circuit 110 emits a first wavelength of light configured for detecting a particular gas, such as $CO_2$, and obtains a spectral response at the first wavelength. For example, the first wavelength of light has a high absorption coefficient for $CO_2$ or other gas being detected. The LEDs/emitters 3910 are pulsed at a high frequency over a short interval to limit inclusion of the volumetric blood flow in the finger tissue in the spectral response. The PPG circuit 110 also emits a second wavelength of light with a low absorption coefficient for $CO_2$ or other gas being detected and obtains a second spectral response at the second wavelength.

The biosensor 100 may then obtain an R value from the first spectral response and the second spectral response. The biosensor 100 may then determine a level of $CO_2$ or other gas being detected using the R value. For example, the biosensor 100 may determine that the CO2 is in a normal range or above a predetermined threshold or in a high range. Based on the R value, the biosensor 100 may provide a level of the $CO_2$ or other gas being detected to the vehicle for display. The biosensor 100 may generate an alert to the vehicle when a detected gas exceeds a threshold such that the vehicle provides an audible or visible feedback.

Figure 40:
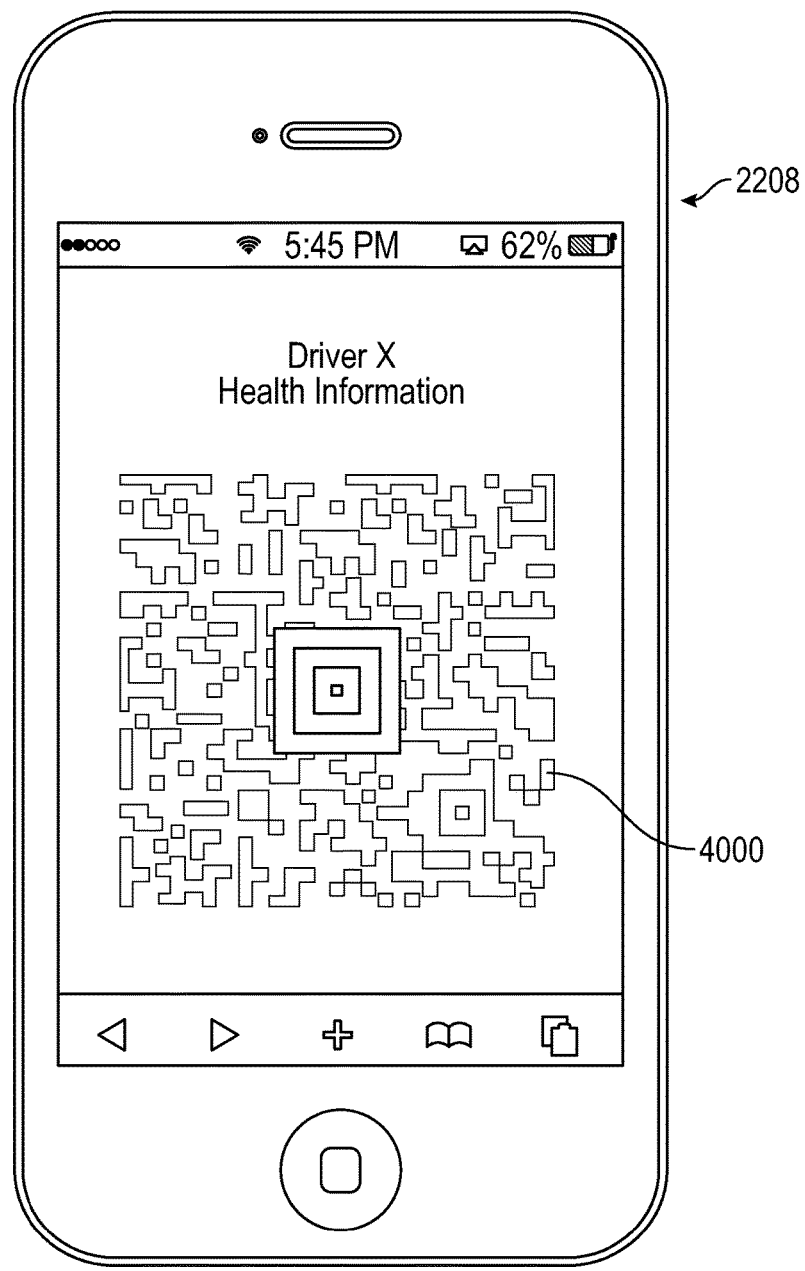
FIG. 40 illustrates a schematic block diagram of an embodiment of a barcode for encoding health information.

FIG. 40 illustrates a schematic block diagram of an embodiment of a barcode 4000 for encoding health information. In an embodiment, a vehicle control system 2502 or user device 2208 or biosensor 100 may encode health information in a barcode 4000. The barcode 4000 may be displayed on the user device 2208. The barcode 4000 allows for quick exchange of health information between user devices.

Figure 41:
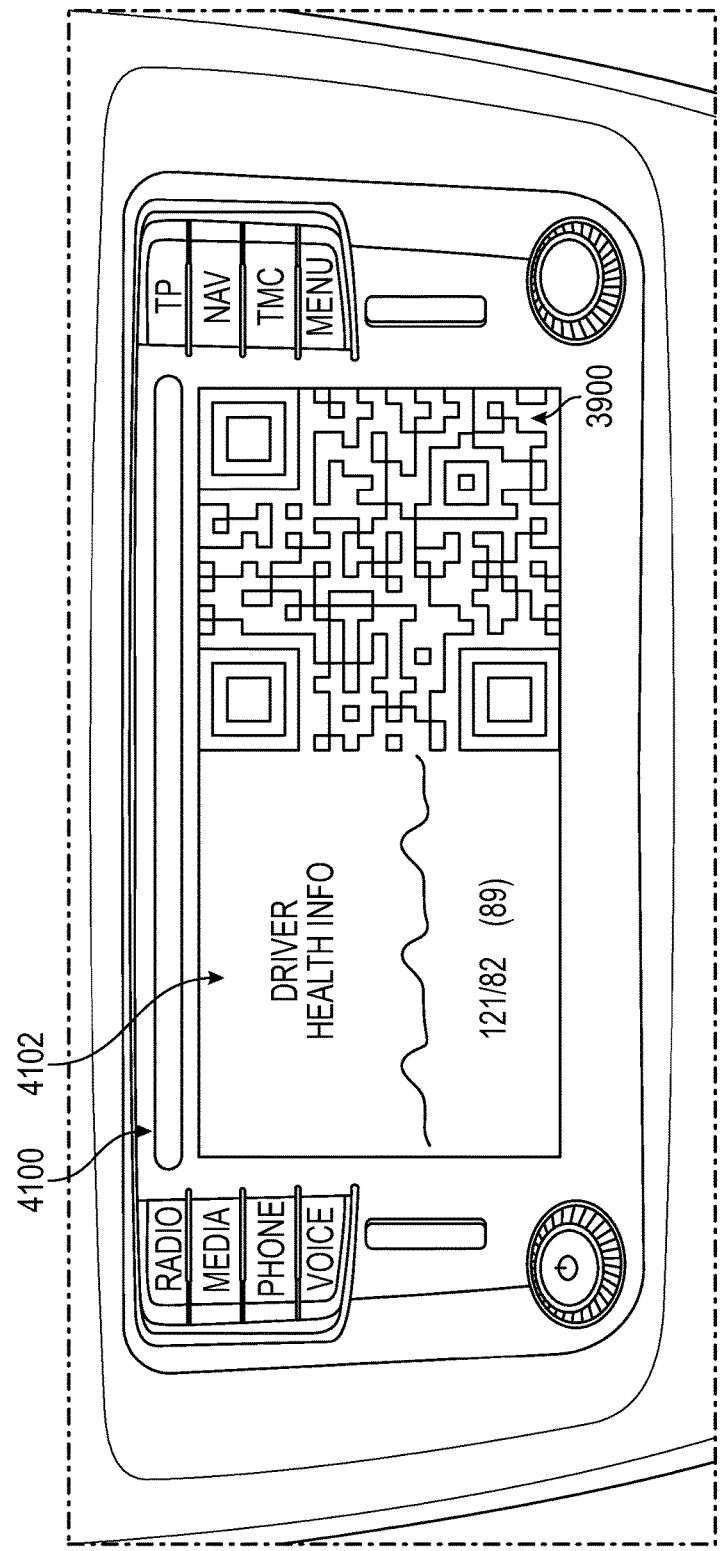
FIG. 41 illustrates a schematic block diagram of an embodiment of a display in a vehicle including a barcode with encoded health information.

FIG. 41 illustrates a schematic block diagram of an embodiment of a display 4100 in a vehicle including a barcode 4000 with encoded health information. The barcode 4000 provides for a quick exchange of health information between user devices or to an emergency service provider, such as a police or health care provider. The health information 4102 may also be displayed on the vehicle display 4100.

In an embodiment, a first barcode may be generated at periodic intervals to provide health information at different intervals. For example, health information may be obtained at a first time period at a start of a trip and encoded in a first barcode with a first time stamp. The health information may then be obtained at a second time period after a health incident or accident. The health information is encoded in a second barcode with a second time stamp. The bar codes may be displayed and/or recorded in a patient's medical record or transmitted over a wide area network to a third party service provider. The bar codes provide a quick and secure exchange of health information between user devices or to an emergency service provider.

Figure 42:
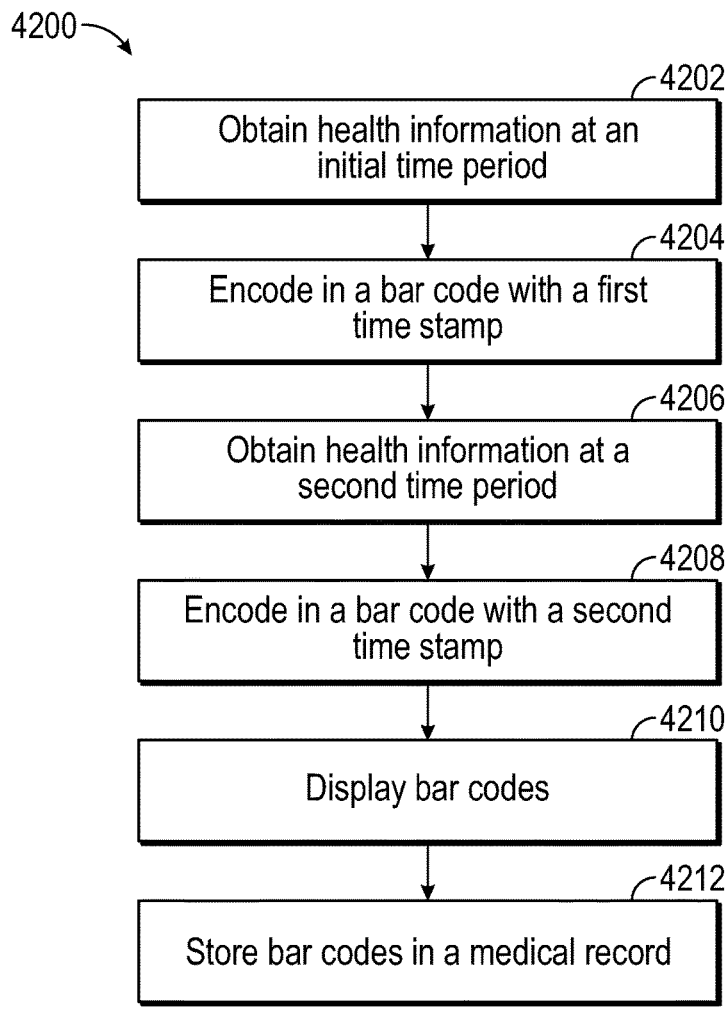
FIG. 42 illustrates a logical flow diagram of an embodiment of a method for providing encoded health information in a barcode.

FIG. 42 illustrates a logical flow diagram of an embodiment of a method 4200 for providing encoded health information in a barcode. Health information for a user is obtained at an initial time period at 4204. The health information may include vital signs or concentrations of one or more substances in blood flow or PPG waveforms of a user. A bar code is generated with a first time stamp at 4204, wherein the bar code encodes the health information. The barcode may include an encryption key to decode the health information, such as a vehicle VIN, social security number of a user or other authentication code. In another embodiment, a biometric measurement of the user is implemented as an encryption key to decode the health information in the barcode.

Health information for the user is then obtained at a second time period at 4206. The health information may be obtained at a predetermined periodic interval. Alternatively, the health information may be obtained in response to a health alert or in response to an accident. A bar code is generated with a second time stamp at 4208, wherein the bar code encodes the health information from the second time period.

The plurality of bar codes may be displayed on a user device or vehicle display. An emergency responder may quickly read the barcodes with a user device and obtain the health information. The bar codes thus provide a quick and secure exchange of the health information. The bar codes may also be transmitted over a wide area network to an emergency service provider or health care provider. The bar codes may also be stored in a medical record for the user at 4212.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A biosensor integrated in a vehicle, comprising:
 a transceiver in the vehicle configured to communicate with a plurality of biosensors; and
 a processing circuit in the vehicle configured to:
  receive first spectral data including photoplethysmography (PPG) waveforms at a first wavelength from a first biosensor at a first location, wherein the first spectral data is less than a predetermined duration;
  receive second spectral data including PPG waveforms at the first wavelength from a second biosensor at a second location, wherein the second spectral data is less than the predetermined duration;
  combine the first spectral data and the second spectral data to generate a combined spectral response at the first wavelength, wherein the combined spectral response is at least the predetermined duration;
  process the combined spectral response of the first spectral data and the second spectral data to obtain health information of a user, wherein the health information includes one or more of: a heart rate, a respiration rate or blood oxygen level.

2. The biosensor of claim 1, wherein the processing circuit is further configured to:
 combine the first spectral data and the second spectral data to obtain a set of PPG waveforms having a sufficient number of waveforms to obtain a heart rate of the user.

3. The biosensor of claim 1, wherein the predetermined duration includes at least five cardiac cycles of the user.

4. The biosensor of claim 1, wherein the processing circuit is further configured to:
 generate an alert to the vehicle in response to the health information for controlling one or more operations of the vehicle.

5. The biosensor of claim 1, wherein the processing circuit is further configured to:
 process the first spectral data and the second spectral data to obtain a biometric measurement of a user.

6. The biosensor of claim 5, wherein the processing circuit is further configured to:
 compare the biometric measurement of the user with one or more stored biometric measurements;
 determine the biometric measurement is within a predetermined threshold; and
 generate an authentication message to the vehicle.

7. The biosensor of claim 6, wherein the biometric measurement of the user includes a blood group.

8. The biosensor of claim 6, wherein the processing circuit is further configured to:
 receive the first spectral data from the first biosensor at the first location, wherein the first location is outside the vehicle;
 receive the second spectral data from the second biosensor at the second location, wherein the second location is outside the vehicle; and
 generate an authentication message to the vehicle from the first biosensor or the second biosensor outside the vehicle.

9. The biosensor of claim 8, wherein the processing circuit is further configured to:
 receive third spectral data from a third biosensor at a third location, wherein the third location is inside the vehicle; and
 generate another authentication message to the vehicle in response to the third spectral data.

10. The biosensor of claim 1, wherein the processing circuit is further configured to:
 receive the first spectral data from the first biosensor at the first location, wherein the first location is outside the vehicle; and receive the second spectral data from the second biosensor at the second location, wherein the second location is within the vehicle.

11. The biosensor of claim 10, wherein the first location includes a key fob associated with the vehicle.

12. The biosensor of claim 11, wherein the second location includes at least one of: a control button within the vehicle or a steering wheel within the vehicle.

13. A biosensor control module, comprising:
a transceiver configured to communicate with a plurality of PPG circuits; and
a processing circuit configured to:
receive first spectral data from a first PPG circuit at a first location having a duration less than a predetermined duration;
receive second spectral data from a second PPG circuit at a second location having another duration less than the predetermined duration;
combine the first spectral data and the second spectral data to obtain a combined spectral response having at least the predetermined duration sufficient to obtain health information of a user; and
process the combined first spectral data and second spectral data to obtain the health information, wherein the health information includes one or more of: a heart rate, a respiration rate or blood oxygen level.

14. The biosensor control module of claim 13, wherein the first spectral data includes a first set of PPG waveforms measured over a first number of cardiac cycles and wherein the second spectral data includes a second set of PPG waveforms measured over a second number of cardiac cycles; and
wherein the combined first number of cardiac cycles and the second number of cardiac cycle includes at least 5 cardiac cycles.

15. The biosensor control module of claim 14, wherein the processing circuit is configured to:
combine the first set of PPG waveforms with the second set of PPG waveforms; and
process the combined first set of PPG waveforms and the second set of PPG waveforms to obtain a biometric measurement of the user.

16. The biosensor control module of claim 13, wherein the processing circuit is further configured to:
process the first spectral data and the second spectral data to obtain a biometric measurement of a user.

17. The biosensor control module of claim 16, wherein the processing circuit is further configured to:
compare the biometric measurement of the user with one or more stored biometric measurements;
determine the biometric measurement is within a predetermined threshold; and
generate an authentication message to a vehicle.

18. The biosensor control module of claim 17, wherein the biometric measurement of the user includes a blood group.

19. The biosensor control module of claim 13, wherein the processing circuit is further configured to:
generate a visual, auditory or tactile feedback in response to the health information.

20. A biosensor, comprising:
a transceiver configured to communicate with a vehicle;
a PPG circuit configured to obtain spectral data including PPG waveforms by:
receiving first spectral data including PPG waveforms at a first wavelength from a first biosensor at a first location, wherein the first spectral data is less than a predetermined duration;
receiving second spectral data including PPG waveforms at the first wavelength from a second biosensor at a second location, wherein the second spectral data is less than the predetermined duration;
a processing circuit configured to:
combine the first spectral data and the second spectral data to generate a combined spectral response at the first wavelength, wherein the combined spectral response is at least the predetermined duration;
process the combined first spectral data and second spectral data to obtain health information of a user, wherein the health information includes one or more of: a heart rate, a respiration rate or blood oxygen level;
generate an indicator of a measurement proceeding; and
generate a health message to the vehicle, wherein the health message includes a request for feedback from the vehicle in response to the health information.

21. The biosensor of claim 20, wherein the health message includes a request for the vehicle to provide one or more of: visible feedback, audible feedback or tactile feedback.

22. The biosensor of claim 20, wherein the processing circuit is further configured to:
process the combined first spectral data and second spectral data to obtain a biometric measurement of a user.

23. The biosensor of claim 22, wherein the processing circuit is further configured to:
compare the biometric measurement of the user with one or more stored biometric measurements;
determine the biometric measurement is within a predetermined threshold; and
generate an authentication message to the vehicle.

24. The biosensor of claim 23, wherein the biometric measurement of the user includes a blood group.

25. The biosensor of claim 22, wherein the processing circuit is further configured to:
generate an indicator of detected heart beats.

26. The biosensor of claim 20, wherein the biosensor is implemented within at least one of: a user device, a key fob, a control button of the vehicle or a steering wheel of the vehicle.

27. The biosensor of claim 26, wherein the user device includes a smart phone.

28. The biosensor of claim 20, wherein the processing circuit is further configured to transmit the health information to a user device.

* * * * *